US007981415B2

(12) United States Patent
Staunton et al.

(10) Patent No.: US 7,981,415 B2
(45) Date of Patent: Jul. 19, 2011

(54) HUMANIZED PAI-1 ANTIBODIES

(75) Inventors: Donald E. Staunton, Kirkland, WA (US); Maximiliano Vasquez, Palo Alto, CA (US)

(73) Assignee: Cisthera, Inc., Kirkland, WA (US)

( * ) Notice: Subject to any disclaimer, the term of this patent is extended or adjusted under 35 U.S.C. 154(b) by 0 days.

(21) Appl. No.: 12/274,793

(22) Filed: Nov. 20, 2008

(65) Prior Publication Data

US 2009/0136500 A1 May 28, 2009

Related U.S. Application Data

(63) Continuation-in-part of application No. 12/205,760, filed on Sep. 5, 2008, now Pat. No. 7,771,720.

(60) Provisional application No. 60/970,871, filed on Sep. 7, 2007.

(51) Int. Cl.
*A61K 39/395* (2006.01)

(52) U.S. Cl. ............... 424/133.1; 424/139.1; 424/158.1; 424/141.1

(58) Field of Classification Search ........................ None
See application file for complete search history.

(56) References Cited

U.S. PATENT DOCUMENTS

| 5,422,245 | A | 6/1995 | Nielsen et al. | |
|---|---|---|---|---|
| 6,767,540 | B2 | 7/2004 | Oh et al. | |
| 7,592,429 | B2 * | 9/2009 | Paszty et al. ............. | 530/388.24 |
| 2001/0034327 | A1 | 10/2001 | Brunner et al. | |
| 2003/0096733 | A1 | 5/2003 | Ny et al. | |
| 2003/0217371 | A1 | 11/2003 | Vaughan et al. | |
| 2005/0037956 | A1 | 2/2005 | Hanashiro et al. | |
| 2006/0058369 | A1 | 3/2006 | Vaughan et al. | |
| 2007/0048315 | A1 | 3/2007 | Presta | |

FOREIGN PATENT DOCUMENTS

| WO | WO 00/45771 | 8/2000 |
|---|---|---|
| WO | WO-2006-113909 A2 | 10/2006 |

OTHER PUBLICATIONS

Agren, A. et al., "Evaluation of low PAI-1 activity as a risk factor for hemorrhagic diathesis," J. Thrombosis Haemostasis 4:201-208 (2005).
Al-Batran, S. et al., "Three-Dimensional In Vitro Cocultivation of Lung Carcinoma Cells with Human Bronchial Organ Culture as a Model for Bronchial Carcinoma," Am. J. Resp. Cell Mol. Biol. 21:200-208 (1999).
Alessi, Marie-Christine, et al., "PAI-1 and the Metabolic Syndrome: Links, Causes and Consequences," Am Heart Assoc: Arterioscler. Thromb. Vasc. Biol. 26:2200-2207 (2006).
Berry, C.N. et al., "Antithrombotic Activity of a Monoclonal Antibody Inducing the Substrate form of Plasminogen Activator Inhibitor Type 1 in Rat Models of Venous and Arterial Thrombosis," British J of Pharmacology 125:29-34 (1998).
Britton, R. C. et al., "Intrahepatic Veno-Occlusive Disease in Cirrhosis with Chronic Ascites: Diagnosis by Hepatic Phlebography and Results of Surgical Treatment," Anals of Surgery 158(3):370-382 (1963).
Correia, Marcello L.G. et al., "A Role for Plasminogen Activator Inhibitor-1 Obesity: From Pie to PAI?" Am Heart Assoc: Arterioscler. Thromb. Vasc. Biol. 26:2183-2185 (2006).
"Correspondence to the Editor," Blood Journal 102:7: 2695-2696 (2003).
Dai, Erbin, et al., "Serp-1, a Viral Anti-Inflammatory Serpin Regulates Cellular Serine Proteinase and Serpin Responses to Vascular Injury," J Bio Chem 278:20:18563-18572 (2003).
DeBrock, S. and Declerck, P.J., "Neutralization of plasminogen activator inhibitor-1 inhibitory properties: identification of two different mechanisms," Biochimica Biophysica Acta 1337:257-266 (1997).
Declerck, P.J. et al., "Measurement of Plasminogen Activator Inhibitor 1 in Biologic Fluids with a Murine Monoclonal Antibody-Based Enzyme-Linked Immunosorbent Assay," Blood Journal 71:1:220-225 (1988).
Downer, G. et al., "Analysis of Renal Fibrosis in a Rabbit Model of Crescentic Nephritis," J. Clin. Invest. 82:998-1006 (1988).
Eddy, Allison A. et al., "Plasminogen Activator Inhibitor-1 in Chronic Kidney Disease: Evidence and Mechanisms of Action," J Am Soc Nephrol 17:2999-3012 (2006).
Fried, M.W. et al., "Post-Transplant Complications Serum Hyaluronic Acid in Patients with Veno-Occlusive Disease Following Bone Marrow Transplant" Bone Marrow Transp. 27:635-639 (2001).
Hemingway, Harry et al. "Prevalence of Angina in Women Versus Men: a Systematic Review and Meta-Analysis of International Variations Across 31 Countries," J Am Heart Assoc, Circulation 117:1526-1536 (2008).
Hicks, K.O. et al., "Use of Three-Dimensional Tissue Cultures to Model Extravascular Transport and Predict In Vivo Activity of Hypoxia-Targeted Anticancer Drugs," J. National Cancer Institute 98(16):1118-1128 (2006).
Holdsworth, S.R. et al., "Abrogation of Macrophage-dependent Injury in Experimental Glomerulonephritis in the Rabbit," J. Clin. Invest. 68:686-698 (1981).
Iredale, J.P., "Models of liver fibrosis: exploring the dynamic nature of inflammation and repair in a solid organ," J. Clin. Investig. 117(3):539-548 (2007).
Kalady, M.F. et al., "Decreased Fibrinolytic Activity in Porcine-to-Primate Cardiac Xenotransplantation," Mol. Med. 4:629-637 (1998).
Kim, J.B. et al., "Three-dimensional in vitro tissue culture models of breast cancer—a review," Breast Cancer Res. Treat. 85(3):281-291 (2004).
King, D.J. et al., "Expression, purification and characterization of a mouse-human chimeric antibody and chimeric Fab' fragment," Biochem. J. 281:317-323 (1992).

(Continued)

*Primary Examiner* — Elizabeth C. Kemmerer
*Assistant Examiner* — Kimberly A. Ballard
(74) *Attorney, Agent, or Firm* — Wilson Sonsini Goodrich & Rosati

(57) ABSTRACT

The present application relates to compositions of humanized anti-PAI-1 antibodies and antigen-binding fragments thereof which convert PAI-1 to its latent form. One aspect relates to antibodies having one or more modifications in at least one amino acid residue of at least one of the framework regions of the variable heavy chain, the variable light chain or both. Another aspect relates to antibodies which bind and neutralize PAI-1 by converting PAI-1 to its latent form or increasing proteolytic cleavage. Another aspect relates to the use of humanized antibodies which inhibit or neutralize PAI-1 for the detection, diagnosis or treatment of a disease or condition associated with PAI-1 or a combination thereof.

6 Claims, 25 Drawing Sheets

OTHER PUBLICATIONS

Lee, J-H, et al. "Veno-Occlusive Disease of the Liver After Allogenic Bone Marrow Transplantation for Severe Aplastic Anemia" Bone Marrow Transp. 26:657-662 (2000).

Liang, X. et al., "Plasminogen activator inhibitor-1 modules adipocyte differentiation," Am. J. Physiol. Endocrinol. Metab. 290(1):E103-E-113 (2006).

Sugimoto, H. et al., "Renal Fibrosis and Glomerulosclerosis in a New Mouse Model of Diabetic Nephropathy and Its Regression by Bone Morphogenic Protein-7 and Advanced Glycation End Product Inhibitors," Diabetes 56:1825-1833 (2007).

Tucker, H.M. et al., "Tissue Plasminogen Activator Requires Plasminogen to Modulate Amyloid-β Neurotoxicity and Deposition," J. Neurochem. 2172-2177 (2000).

Tucker, H.M. et al., "The Plasmin System Is Induced by and Degrades Amyloid-β Aggregates," J. Neuroscience 20(11):3937-3946 (2000).

Vincan, E. et al., "A Human Three-Dimensional Cell Line Model Allows the Study of Dynamic and Reversible Epithelial-Mesenchymal and Mesenchymal-Epithelial Transition That Underpins Colorectal Carcinogenesis," Cells Tissues Organs 185:20-28 (2007).

Wang, D. et al., "β-Amyloid Degradation and Alzheimer's Disease," J. Biomedicine Biotech. vol. 2006, Article ID 58406, pp. 1-12, (2006).

PCT/US08/75489 Search Report dated Feb. 12, 2009.

* cited by examiner

Figure 1

Human B3-Vκ4 V$_L$ with MA-33B8 grafted CDRs underlined

Human VH1-2 V$_H$ with MA-33B8 grafted CDRs underlined

| 2 | | | | | | | | | | | | | | | | | | | | | | | | |
|---|---|---|---|---|---|---|---|---|---|---|---|---|---|---|---|---|---|---|---|---|---|---|---|---|
| Q | V | Q | L | V | Q | S | G | A | E | V | K | K | P | G | A | S | V | K | V | S | C | K | A | S | G | Y | T | F | T | _N_ | _Y_ | _G_ | _M_ | _N_ |

| | | | | | | | | | | | | | 46 | | | | | | | | | | | |
|---|---|---|---|---|---|---|---|---|---|---|---|---|---|---|---|---|---|---|---|---|---|---|---|---|
| 38 | | | | | | | | | | | | | | | | | | | | | | | | |
| W | V | R | Q | A | P | G | Q | G | L | E | W | M | G | _W_ | _I_ | _N_ | _T_ | _Y_ | _T_ | _G_ | _E_ | _P_ | _T_ | _Y_ | _D_ | _D_ | _E_ | _F_ | _K_ | _G_ | R |
| | | K | | | | | | | | | | | V | | | | | | | | | | | | | | | | | | |

| 67 | | 69 | | 71 | | | | | | | | | | | | | | | | | | | | | | 94 |
|---|---|---|---|---|---|---|---|---|---|---|---|---|---|---|---|---|---|---|---|---|---|---|---|---|---|---|
| V | T | M | T | R | D | T | S | I | S | T | A | Y | M | E | L | S | R | L | R | S | D | D | T | A | V | Y | Y | C | A | R |
| | | F | | L | | | | | | | | | | | | | | | | | | | | | | K |
| | | I | | | | | | | | | | | | | | | | | | | | | | | | |

| | | | | | | | | | | | | | | | |
|---|---|---|---|---|---|---|---|---|---|---|---|---|---|---|---|
| D | V | S | G | F | E | _F_ | _D_ | _Y_ | W | G | Q | G | T | L | V | T | V | S | S |

Figure 3

A.  33B8 Humanized V$_L$ (SEQ ID NO: 3)

DIVMTQSPDSLAVSLGERATINCKSSQSLLNIIKQKNCLAWYQQKPGQPPKLLIYWASTRESGVPDRFSGSGSGTDFTLTISSLQAEDVAVY
YCQQYYSYPYTFGQGTKLEIK

B.  33B8 Humanized V$_H$ (SEQ ID NO: 17)

QVQLVQSGAEVKKPGASVKVSCKASGYTFTNYGMNWVRQAPGQGLEWMGWINTYTGEPTYTDDFKGRFTMTLDTSISTAYMELSRLR
SDDTAVYYCAKDVSGFVFDYWGQGTLVTVSS

Figure 4

A.  33B8 Humanized V$_L$ (SEQ ID NO: 3)

DIVMTQSPDSLAVSLGERATINCKSSQSLLNIIKQKNCLAWYQQKPGQPPKLLIYWASTRESGVPDRFSGSGSGTDFTLTISSLQAEDVAVY
YCQQYYSYPYTFGQGTKLEIK

B.  33B8 Humanized V$_H$ (SEQ ID NO: 18)

QVQLVQSGAEVKKPGASVKVSCKASGYTFTNYGMNWVRQAPGQGLKWMGWINTYTGEPTYTDDFKGRFTFTLDTSISTAYMELSRLRS
DDTAVYYCAKDVSGFVFDYWGQGTLVTVSS

Figure 8

Humanized 33B8

A. CT110 Variable Heavy Chain (IgG1) (SEQ ID NO: 99)

MDWTWRILFLVAAATGAHSQVQLVQSGAEVKKPGASVKVSCKASGYTFTNYGMNWVRQAPGQGLEWMGWINTYTGEPTYTDDF
KGRFTMTLDTSISTAYMELSRLRSDDTAVYYCAKDVSGFVFDYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGK

B. CT140 Variable Heavy Chain (IgG4) (SEQ ID NO: 100)

MDWTWRILFLVAAATGAHSQVQLVQSGAEVKKPGASVKVSCKASGYTFTNYGMNWVRQAPGQGLEWMGWINTYTGEPTYTDDF
KGRFTMTLDTSISTAYMELSRLRSDDTAVYYCAKDVSGFVFDYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKRVEPKSCDKTHTCPPCPAPELLGGPS
VFLFPPKPKDTLMISRTPEVTCVVVDVSQEDPEVQFNWYVDGVEVHNAKTKPREEQFNSTYRVVSVLTVLHQDWLNGKEYKCKVSN
KGLPSSIEKTISKAKGQPREPQVYTLPPSPEEMTKNQVSLTCLVKGFYPSDIAVEWESNGQPENNYKTTPPVLDSDGSFFLYSRLTVDK
SRWQEGNVFSCSVMHEALHNHYTQKSLSLSLGK

C. Variable Light Chain of CT110 and CT140 (SEQ ID NO: 101)

MRLPAQLLGLLMLWVSGSSGDIVMTQSPDSLAVSLGERATINCKSSQSLLNHKQKNCLAWYQQKPGQPPKLLIYWASTRESGVPDRF
SGSGSGTDFTLTISSLQAEDVAVYYCQQYSYPYTFGQGTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC

Figure 9

Human VH1-f V_H with 55F4C12 grafted CDRs underlined

Positions 27, 28, 29, 30:

| | | | | | | | | | | | | | | | | | | | | | | | | 27 | 28 | 29 | 30 | | | | |
|---|---|---|---|---|---|---|---|---|---|---|---|---|---|---|---|---|---|---|---|---|---|---|---|---|---|---|---|---|---|---|---|
| E | V | Q | L | V | Q | S | G | A | E | V | K | K | P | G | A | T | V | K | I | S | C | K | V | S | G | Y | T | F | T | D | I | Y | M | Y |
| | | | | | | | | | | | | | | | | | | | | | | | | | | F | N | I | K | | | | | |

Positions 38, 48, 66, 67:

| | 38 | | | | | | | | | | 48 | | | | | | | | | | | | | | | | | 66 | 67 | | |
|---|---|---|---|---|---|---|---|---|---|---|---|---|---|---|---|---|---|---|---|---|---|---|---|---|---|---|---|---|---|---|---|
| W | V | Q | Q | A | P | G | K | G | L | E | W | M | G | R | I | D | P | A | N | G | N | T | E | F | D | P | K | F | Q | D | R | V | T |
| | K | | | | | | | | | | | I | | | | | | | | | | | | | | | | | | | K | A |

Positions 93, 94:

| | | | | | | | | | | | | | | | | 93 | 94 | | | | | |
|---|---|---|---|---|---|---|---|---|---|---|---|---|---|---|---|---|---|---|---|---|---|---|---|
| T | A | D | T | S | T | D | T | A | Y | M | E | L | S | S | L | R | S | E | D | T | A | V | Y | Y | C | A | T |
| | | | | | | | | | | | | | | | | | | | | | | | | | | T | R |

| W | Y | F | D | V | W | G | Q | G | T | L | V | T | V | S |
|---|---|---|---|---|---|---|---|---|---|---|---|---|---|---|

Figure 10

Human O8-Vκ1-Jκ4 V_L with 55F4C12 grafted CDRs underlined

Row 1 (positions 1–23):
| D | I | Q | M | T | Q | S | P | S | S | L | S | A | S | V | G | D | R | V | T | I | T | C | R | A | S | Q | D | I | S | N | Y | L | H | W |

Row 2 (positions ~24–55, with 43, 44 marked):
| Y | Q | Q | K | P | G | K | A | P | K | L | L | I | Y | Y | T | S | R | L | H | S | G | V | P | S | R | F | S | G | S | G | S | G | T | D |
| | | | | | | | 43 | 44 | | | | | | | | | | | | | | | | | | | | | | | | | | |
| | | | | | | | T | V | | | | | | | | | | | | | | | | | | | | | | | | | | |

Row 3 (positions 71–, with 87 marked):
| F | T | F | T | I | S | S | L | Q | P | E | D | I | A | T | Y | Y | C | Q | Q | G | D | T | L | P | P | P | T | F | G | G | G | T | K | V |
| | | | | | | | | | | | | | | | | 87 | | | | | | | | | | | | | | | | | | |
| | | | | | | | | | | | | | | | | F | | | | | | | | | | | | | | | | | | |

Row 4:
| E | I | K |

Figure 16

A.  55F4 Variable light chain engineering

```
55F_VK    DIQMTQSPSSLSASLGDRVTISCRASQDISNYLHWYQQKPDGTVKLLIYYTSRLHS
          |||||||||||||||*|||||*||||||||||||||**||||**||||*||**
O8-VK1    DIQMTQSPSSLSASVGDRVTITCQASQDISNYLNWYQQKPGKAPKLLIYDASNLET
Hum0      ..............................RASQDISNYLH............YTSRLHS
Hum1      ..............................RASQDISNYLH............YTSRLHS

55F_VK    GVPSRFSGSGSGTDYSLTISNLKQEDFATYFCQQGDTLPPTFGGGTKLEIK
          |||||||||||||||***|||*|||*|*||*||||||||||||*|||
O8-VK1    GVPSRFSGSGSGTDFTFTISSLQPEDIATYYCQQYDNLPLTFGGGTKVEIK    (JK4)
Hum0      ..............................QQGDTLPPT...........
Hum1      ..............Y...............QQGDTLPPT...........
```

B.  55F4 Variable heavy chain engineering

```
55F_VH    QVQLQQSGAELVKPGASVKLSCTASGFNIKDIYMYWVKQRPEQGLEWIGRIDPANGNTEF
          *|*|||||||*|||||||*|*|*|||||||||||*||||*||*||||*||*|*||||||
VH1-f     EVQLVQSGAEVKKPGATVKISCKVSGYTFTDYYMHWVQQAPGKGLEWMGLVDPEDGETIY
Hum1      ...................................FNIKDIYMY...........RIDPANGNTEF
Hum2      ...................................FNIKDIYMY...........RIDPANGNTEF
Hum3      ...................................FNIKDIYMY..........I..RIDPANGNTEF

55F_VH    DPKFQDKATITADTSSNTAYLQLSSLTSEDTAVYYCTRSLYGSSPWYFDVWGQGTTVTVS
          ***||*||*|||||||*|*|||||*|||*||||||||||||||||||||||*|||*|||
VH1-f     AEKFQGRVTITADTSTDTAYMELSSLRSEDTAVYYCAT------YFDYWGQGTLVTVS
Hum1      DPKFQD.A.................................RSLYGSSPWYFDV........
Hum2      DPKFQD.A.................................TRSLYGSSPWYFDV.......
Hum3      DPKFQDKA.................................RSLYGSSPWYFDV........
```

(SEQ ID NO: 58)

(SEQ ID NO: 60)
(SEQ ID NO: 62)
(SEQ ID NO: 63)

(SEQ ID NO: 59)

(SEQ ID NO: 61)
(SEQ ID NO: 65)
(SEQ ID NO: 66)
(SEQ ID NO: 67)

Figure 17

A. 33B8 Variable heavy chain engineering

```
33B8    QIQLVQSGPELKKPGKTVTISCKASGYTFTNYGMNWVKQAPGKGLKWMGWINTYTGEPTY
        |*|||||||*||||||||*|||*|||||||||||||*|*|||*||*|||||||||||||
VH1-2   QVQLVQSGAEVKKPGASVKVSCKASGYTFTGYYMHWVRQAPGQGLEWMGWINPNSGGTNY
Hum1    ..........................NYGMN............WINTYTGEPTY
Hum2    ..........................NYGMN........K...WINTYTGEPTY

33B8    TDDFKGRFAFSLDTSASTAYLQISNLKNEDTATYFCAKDVSGFVFDYWGQGTTVTVSS           (SEQ ID NO: 15)
        *|||||*|*|||*||||||*|||*|||||||||*||*|||||||||||||||||||
VH1-2   AQKFQGRVTMTRDTSISTAYMELSRLRSDDTAVYYCAR----YFDYWGQGTLVTVSS   (JH4)    (SEQ ID NO: 14)
Hum1    TDDFKG.F..L.....................KDVSGFVFDY.............                (SEQ ID NO: 17)
Hum2    TDDFKG.F..L.....................KDVSGFVFDY.............                (SEQ ID NO: 18)
```

B. 33B8 Variable light chain engineering

```
33B8    DIVMTQSPSSLAVSVGEKVTMSCKSSQSLLNIIKQKNCLAWYQQKPGQSPKLLIYWASTRES
        ||||||||*|||||||||*|**|||||||||||*|*|||||||||||**|||||||||||
B3-VK4  DIVMTQSPDSLAVSLGERATINCKSSQSVLYSSNNKNYLAWYQQKPGQPPKLLIYWASTRES
Hum1    ............................KSSQSLLNIIKQKNCLA..........WASTRES

33B8    GVPDRFTGSGSGTDFTLTISSVKAEDLAVYYCQQYYSYPYTFGGGTKLEIK              (SEQ ID NO: 1)
        ||||||*|||||||||||||*|*|||*|||||||||*|||||||*||||||
B3-VK4  GVPDRFSGSGSGTDFTLTISSLQAEDVAVYYCQQYYSTPYTFGQGTKLEIK    (Jk2)    (SEQ ID NO: 2)
Hum1    .......................QQYYSYPYT.................                (SEQ ID NO: 3)
```

US 7,981,415 B2

HUMANIZED PAI-1 ANTIBODIES

CROSS-REFERENCE

This application is a continuation-in-part of U.S. patent application Ser. No. 12/205,760, filed Sep. 5, 2008 now U.S. Pat. No. 7,771,720, which claims the benefit of U.S. Provisional Application Ser. No. 60/970,871, filed Sep. 7, 2007, which are incorporated herein in their entireties by reference.

BACKGROUND OF THE INVENTION

A defective fibrinolytic system participates in the persistence of venous and arterial thrombi. The two principal inhibitors of fibrinolysis are plasminogen activator inhibitor-1 (PAI-1), an inhibitor of tissue-type plasminogen activator (tPA) and urokinase-type plasminogen activator (uPA), and α2-antiplasmin, a specific plasmin inhibitor. Regulation of the plasmin system by PAI-1 regulates both fibrinolysis in the vasculature as well as extracellular matrix (ECM) degradation in the tissues. PAI-1, a 50-kDa glycoprotein, belongs to the serine proteinase inhibitor (serpin) superfamily. In its active form, PAI-1 controls tPA and uPA activity through the rapid formation of an inactive complex. The active form is unstable and converts spontaneously into a non-inhibitory latent form. In plasma, PAI-1 is stabilized through binding with vitronectin. A third conformation, the non-inhibitory substrate form, interacts with tPA and uPA resulting in the cleavage and irreversible inactivation of PAI-1 and the regeneration of the proteinase activity.

Abnormal variations in PAI-1 plasma levels have been correlated with a disturbed balance in the fibrinolytic process. Patients having increased plasma PAI-1 concentrations are positively correlated with several cardiovascular diseases, including venous thromboembolism, sepsis and coronary artery disease. Elevated PAI-1 plasma concentrations are correlated with the insulin-resistance syndrome and increased local expression of PAI-1 is observed in atherosclerotic plaques.

SUMMARY OF THE INVENTION

Provided herein are humanized antibodies or antigen-binding fragments thereof that bind to PAI-1 and induce a conformational change of PAI-1 to its latent form. Such antibodies have in vitro and in vivo purification, detection, diagnostic and therapeutic uses. Also provided herein are humanized antibodies or antigen-binding fragments thereof that bind to one or more species of PAI-1. In one aspect, humanized antibodies or antigen-binding fragments thereof described herein bind one or more of mouse, rat, rabbit and human PAI-1.

Provided herein are antibodies, or antigen-binding fragments thereof, comprising a heavy chain variable region having an amino acid sequence set forth as SEQ ID NO: 16 and a light chain variable region having an amino acid sequence set forth as SEQ ID NO: 3. In one embodiment, the antibody, or antigen-binding fragment thereof, has a heavy chain variable region further including one or more modifications such as, for example, a substitution of valine (V) by isoleucine (I) or leucine (L) at position 2; a substitution of arginine (R) by lysine (K) at position 38; a substitution of glutamic acid (E) by lysine (K) or valine (V) at position 46; a substitution of valine (V) by phenylalanine (F) position 67; a substitution of methionine (M) by phenylalanine (F) or isoleucine (I) at position 69; a substitution of arginine (R) by leucine (L) at position 71; and a substitution of arginine (R) by lysine (K) at position 94 utilizing the Kabat numbering system.

Provided herein are antibodies, or antigen-binding fragments thereof, comprising a heavy chain variable region having an amino acid sequence set forth as SEQ ID NO: 17 and a light chain variable region having an amino acid sequence set forth as SEQ ID NO: 3. In one embodiment, the antibody, or antigen-binding fragment thereof, has a heavy chain variable region further including one or more modifications such as, for example, a substitution of valine (V) by isoleucine (I) or leucine (L) at position 2; a substitution of arginine (R) by lysine (K) at position 38; a substitution of glutamic acid (E) by lysine (K) or valine (V) at position 46; and a substitution of methionine (M) by phenylalanine (F) or isoleucine (I) at position 69, utilizing the Kabat numbering system.

Provided herein are antibodies, or antigen-binding fragments thereof, having a heavy chain variable region having an amino acid sequence set forth as SEQ ID NO: 18 and a light chain variable region having an amino acid sequence set forth as SEQ ID NO: 3. A heavy chain variable region in such an antibody or antigen-binding fragment thereof, can further include one or more modifications such as, for example, a substitution of valine (V) by isoleucine (I) or leucine (L) at position 2; and a substitution of arginine (R) by lysine (K) at position 38, utilizing the Kabat numbering system.

Provided herein are antibodies, or antigen-binding fragments thereof which binds PAI-1 having a heavy chain variable region having an amino acid sequence set forth as SEQ ID NO: 16 and a light chain variable region having an amino acid sequence set forth as SEQ ID NO: 3, wherein said heavy chain variable region comprises one or more modifications including, but not limited to, a substitution of valine (V) by isoleucine (I) at position 2, a substitution of valine (V) by leucine (L) or isoleucine (I) at position 2, a substitution of arginine (R) by lysine (K) at position 38; a substitution of glutamic acid (E) by lysine (K) or valine (V) at position 46; a substitution of phenylalanine (F) by valine (V) at position 67; a substitution of methionine (M) by phenylalanine (F) or isoleucine (I) at position 69; a substitution of leucine (L) by arginine (R) at position 71; and a substitution of lysine (K) by arginine (R) at position 94 utilizing the Kabat numbering system.

In any of such antibodies, or antigen-binding fragments thereof, the light chain variable region can further include one or more modifications such as, for example, in framework 1 of the light chain variable region, where said modification is, for example, a substitution of asparagine (N) by serine (S) or threonine (T) at position 22 utilizing the Kabat numbering system.

Provided herein are antibodies and antigen-binding fragments that bind PAI-1, comprising a heavy chain variable region and a light chain variable region, wherein said heavy chain variable region comprises:
  (i) a CDR1 of SEQ ID NO: 52, a CDR2 of SEQ ID NO: 53, and a CDR3 of SEQ ID NO: 54;
  (ii) a heavy chain FR1 having the amino acid sequence of SEQ ID NO: 19 or the amino acid sequence of SEQ ID NO: 19 except for a substitution of valine (V) by isoleucine (I) or leucine (L) at position 2 utilizing the Kabat numbering system;
  (iii) a heavy chain FR2 having the amino acid sequence of SEQ ID NO: 21 or the amino acid sequence of SEQ ID NO: 21 except for one or more substitutions selected from the group consisting of:
    (a) a substitution of arginine (R) by lysine (K) at position 38, and (b) a substitution of glutamic acid (E) by lysine (K) or valine (V) at position 46 utilizing the Kabat numbering system;

(iv) a heavy chain FR3 having the amino acid sequence of SEQ ID NO: 27 or the amino acid sequence of SEQ ID NO: 27 except for one or more substitutions selected from the group consisting of:

(a) a substitution of valine (V) by phenylalanine (F) at position 67;
(b) a substitution of methionine (M) by phenylalanine (F) or isoleucine (I) at position 69;
(c) a substitution of arginine (R) by leucine (L) at position 71; and
(d) a substitution of arginine (R) by lysine (K) at position 94 utilizing the Kabat numbering system; and (v) a heavy chain FR4 having the amino acid sequence of SEQ ID NO: 51 or the amino acid sequence of SEQ ID NO: 51 except for one or more conservative substitutions, and wherein said light chain variable region comprises:

(i) a CDR1 of SEQ ID NO: 10 or 11, a CDR2 of SEQ ID NO: 12, and a CDR3 of SEQ ID NO: 13;
(ii) a light chain FR1 having the amino acid sequence of SEQ ID NO: 5 or the amino acid sequence of SEQ ID NO: 5 except for a substitution of asparagine (N) by serine (S) or threonine (T) at position 22 utilizing the Kabat numbering system;
(iii) a light chain FR2 having the amino acid sequence of SEQ ID NO: 7 or the amino acid sequence of SEQ ID NO: 7 except for one or more conservative substitutions;
(iv) a light chain FR3 having the amino acid sequence of SEQ ID NO: 8 or the amino acid sequence of SEQ ID NO: 8 except for one or more conservative substitutions; and
(v) a light chain FR4 having the amino acid sequence of SEQ ID NO: 9 or the amino acid sequence of SEQ ID NO: 9 except for one or more conservative substitutions.

In one non-limiting embodiment, the antibody, or antigen-binding fragment thereof, comprises a heavy chain FR1 having an amino acid sequence as set forth in SEQ ID NO: 19; a heavy chain FR2 having an amino acid sequence as set forth in SEQ ID NO: 21; a heavy chain FR3 having an amino acid sequence as set forth in SEQ ID NO: 35; a heavy chain FR4 having an amino acid sequence as set forth in SEQ ID NO: 51; a light chain FR1 having an amino acid sequence as set forth in SEQ ID NO: 5; a light chain FR2 having an amino acid sequence as set forth in SEQ ID NO: 7; a light chain FR3 having an amino acid sequence as set forth in SEQ ID NO: 8; and a light chain FR4 having an amino acid sequence as set forth in SEQ ID NO: 9.

In another non-limiting embodiment, the antibody, or antigen-binding fragment thereof, comprises a heavy chain FR1 having an amino acid sequence as set forth in SEQ ID NO: 19; a heavy chain FR2 having an amino acid sequence as set forth in SEQ ID NO: 23; a heavy chain FR3 having an amino acid sequence as set forth in SEQ ID NO: 33; a heavy chain FR4 having an amino acid sequence as set forth in SEQ ID NO: 51; a light chain FR1 having an amino acid sequence as set forth in SEQ ID NO: 5; a light chain FR2 having an amino acid sequence as set forth in SEQ ID NO: 7; a light chain FR3 having an amino acid sequence as set forth in SEQ ID NO: 8; and a light chain FR4 having an amino acid sequence as set forth in SEQ ID NO: 9.

In one aspect, the antibodies and antigen-binding fragments described herein can further comprise a substitution of cysteine (C) by leucine (L) at position 32 of the light chain variable region utilizing the Kabat numbering system.

In one aspect, the humanized antibody, or antigen-binding fragment thereof, comprises a variable light chain having an amino acid sequence set forth as SEQ ID NO: 101 and a variable heavy chain fused to an IgG1 Fc construct, wherein said heavy chain fusion protein has an amino acid sequence set forth as SEQ ID NO: 99.

In another aspect, the humanized antibody, or antigen-binding fragment thereof, comprises a variable light chain having an amino acid sequence set forth as SEQ ID NO: 101 and a variable heavy chain fused to an IgG4 Fc construct, wherein said heavy chain fusion protein has an amino acid sequence set forth as SEQ ID NO: 100.

In addition to humanized antibodies or antigen-binding fragments thereof that bind to PAI-1 and induce a conformational change of PAI-1 to its latent form, provided herein are humanized antibodies or antigen-binding fragments thereof that bind to PAI-1, decrease complex formation between PAI-1 and its target proteinases, and increase cleavable PAI-1. Further provided herein are humanized antibodies or antigen-binding fragments thereof that bind to PAI-1 and induce transition of PAI-1 to its substrate form. Such antibodies have in vitro and in vivo purification, detection, diagnostic and therapeutic uses. Also provided herein are humanized antibodies or antigen-binding fragments thereof that bind to one or more species of PAI-1. In one aspect, humanized antibodies or antigen-binding fragments thereof described herein bind one or more of mouse, rat, rabbit and human PAI-1.

Provided herein is an antibody, or antigen-binding fragment thereof, comprising a light chain variable region having an amino acid sequence set forth as SEQ ID NO: 62 and a heavy chain variable region having an amino acid sequence set forth as SEQ ID NO: 64.

Provided herein is an antibody, or antigen-binding fragment thereof, comprising a light chain variable region having an amino acid sequence set forth as SEQ ID NO: 62 and a heavy chain variable region having an amino acid sequence set forth as SEQ ID NO: 64, wherein: the heavy chain variable region further comprises one or more modifications selected from the group consisting of a substitution of tyrosine (Y) by phenylalanine (F) at position 27; a substitution of threonine (T) by asparagine (N) at position 28; a substitution of phenylalanine (F) by isoleucine (I) at position 29; a substitution of threonine (T) by lysine (K) position 30; a substitution of glutamine (Q) by lysine (K) at position 38; a substitution of methionine (M) by isoleucine (I) at position 48; a substitution of arginine (R) by lysine (K) at position 66; a substitution of valine (V) by alanine (A) at position 67; a substitution of alanine (A) by threonine (T) at position 93; and a substitution of threonine (T) by arginine (R) at position 94 utilizing the Kabat numbering system; and the light chain variable region further comprises one or more modifications selected from the group consisting of a substitution of alanine (A) by threonine (T) at position 43; a substitution of proline (P) by valine (V) at position 44; a substitution of phenylalanine (F) by tyrosine (Y) at position 71; and a substitution of tyrosine (Y) by phenylalanine (F) at position 87 utilizing the Kabat numbering system.

Provided herein is an antibody, or antigen-binding fragment thereof, that binds PAI-1 comprising a heavy chain variable region having an amino acid sequence set forth as SEQ ID NO: 64, 65, 66 or 67; and a light chain variable region having an amino acid sequence set forth as SEQ ID NO: 62 or 63. In one embodiment, the antibody, or antigen-binding fragment thereof, comprises a heavy chain variable region having an amino acid sequence set forth as SEQ ID NO: 64 and a light chain variable region having an amino acid sequence set forth as SEQ ID NO: 62. In another embodiment, the antibody, or antigen-binding fragment thereof, that binds PAI-1 comprises a heavy chain variable region having an amino acid sequence set forth as SEQ ID NO: 64 and a light chain variable region having an amino acid sequence set forth as SEQ ID NO: 63. In another embodiment, the antibody, or antigen-binding fragment thereof, that binds PAI-1 comprises a heavy chain variable region having an amino acid sequence set forth as SEQ ID NO: 65 and a light chain variable region having an amino acid sequence set forth as SEQ ID NO: 62. In another embodiment, the antibody, or antigen-binding fragment thereof, that binds PAI-1 comprises a heavy chain variable region having an amino acid sequence set forth as SEQ ID NO: 65 and a light chain variable region having an amino acid sequence set forth as SEQ ID NO: 63. In another embodiment, the antibody, or antigen-binding fragment thereof, that binds PAI-1 comprises a heavy chain variable region having an amino acid sequence set forth as SEQ ID NO: 66 and a light chain variable region having an amino acid sequence set forth as SEQ ID NO: 62. In another embodiment, the antibody, or antigen-binding fragment thereof, that binds PAI-1 comprises a heavy chain variable region having an amino acid sequence set forth as SEQ ID NO: 66 and a light chain variable region having an amino acid sequence set forth as SEQ ID NO: 63. In another embodiment, the antibody, or antigen-binding fragment thereof, that binds PAI-1 comprises a heavy chain variable region having an amino acid sequence set forth as SEQ ID NO: 67 and a light chain variable region having an amino acid sequence set forth as SEQ ID NO: 62. In yet another embodiment, the antibody, or antigen-binding fragment thereof, that binds PAI-1 comprises a heavy chain variable region having an amino acid sequence set forth as SEQ ID NO: 67; and a light chain variable region having an amino acid sequence set forth as SEQ ID NO: 63. In any of such embodiments, the heavy chain variable region can further comprise a substitution of glutamine (Q) by lysine (K); and the light chain variable region further comprise one or more modifications selected from the group consisting of: a substitution of alanine (A) by threonine (T) at position 43, a substitution of proline (P) by valine (V) at position 44, and a substitution of tyrosine (Y) by phenylalanine (F) at position 87 utilizing the Kabat numbering system.

Provided herein is an antibody, or antigen-binding fragment thereof that binds PAI-1, comprising a heavy chain variable region and a light chain variable region, wherein said heavy chain variable region comprises:
(i) a CDR1 of SEQ ID NO: 93, a CDR2 of SEQ ID NO: 94, and a CDR3 of SEQ ID NO: 95;
(ii) a heavy chain FR1 having the amino acid sequence of SEQ ID NO: 78 or the amino acid sequence of SEQ ID NO: 78 except for one or more substitutions selected from the group consisting of:
  (a) a substitution of tyrosine (Y) by phenylalanine (F) at position 27;
  (b) a substitution of threonine (T) by asparagine (N) at position 28;
  (c) a substitution of phenylalanine (F) by isoleucine (I) at position 29; and
  (d) a substitution of threonine (T) by lysine (K) at position 30 utilizing the Kabat numbering system;
(iii) a heavy chain FR2 having the amino acid sequence of SEQ ID NO: 84 or the amino acid sequence of SEQ ID NO: 84 except for one or more substitutions selected from the group consisting of:
  (a) a substitution of glutamine (Q) by lysine (K) at position 38, and
  (b) a substitution of methionine (M) by isoleucine (I) at position 48 utilizing the Kabat numbering system;
(iv) a heavy chain FR3 having the amino acid sequence of SEQ ID NO: 88 or the amino acid sequence of SEQ ID NO: 88 except for one or more substitutions selected from the group consisting of:
  (a) a substitution of arginine (R) by lysine (K) at position 66;
  (b) a substitution of valine (V) by alanine (A) at position 67;
  (c) a substitution of alanine (A) by threonine (T) at position 93; and
  (d) a substitution of threonine (T) by arginine (R) at position 94 utilizing the Kabat numbering system; and
(v) a heavy chain FR4 having the amino acid sequence of SEQ ID NO: 92 or the amino acid sequence of SEQ ID NO: 92 except for one or more conservative substitutions;
and said light chain variable region comprises:
(i) a CDR1 of SEQ ID NO: 96, a CDR2 of SEQ ID NO: 97, and a CDR3 of SEQ ID NO: 98;
(ii) a light chain FR1 having the amino acid sequence of SEQ ID NO: 68 or the amino acid sequence of SEQ ID NO: 68 except for one or more conservative substitutions;
(iii) a light chain FR2 having the amino acid sequence of SEQ ID NO: 69 or the amino acid sequence of SEQ ID NO: 69 except for one or more substitutions selected from the group consisting of:
  (a) a substitution of alanine (A) by threonine (T) at position 43; and
  (b) a substitution of proline (P) by valine (V) at position 44 utilizing the Kabat numbering system;
(iv) a light chain FR3 having the amino acid sequence of SEQ ID NO: 73 or the amino acid sequence of SEQ ID NO: 73 except for one or more substitutions selected from the group consisting of:
  (a) a substitution of phenylalanine (F) by tyrosine (Y) at position 71; and
  (b) a substitution of tyrosine (Y) by phenylalanine (F) utilizing the Kabat numbering system; and
(v) a light chain FR4 having the amino acid sequence of SEQ ID NO: 77 or the amino acid sequence of SEQ ID NO: 77 except for one or more conservative substitutions.

An antibody, or antigen-binding fragment thereof, provided herein can comprise a heavy chain variable region CDR1 having an amino acid sequence as set forth in SEQ ID NO: 93, a heavy chain variable region CDR2 having an amino acid sequence as set forth in SEQ ID NO: 94, a heavy chain variable region CDR3 having an amino acid sequence as set forth in SEQ ID NO: 95, a light chain variable region CDR1 having an amino acid sequence as set forth in SEQ ID NO: 96, a light chain variable region CDR2 having an amino acid sequence as set forth in SEQ ID NO: 97, and a light chain variable region CDR3 having an amino acid sequence as set forth in SEQ ID NO: 98.

In one embodiment, the antibody, or antigen-binding fragment thereof, comprises a heavy chain variable region FR1 having an amino acid sequence as set forth in SEQ ID NO: 78; a heavy chain variable region FR2 having an amino acid sequence as set forth in SEQ ID NO: 84; a heavy chain variable region FR3 having an amino acid sequence as set forth in SEQ ID NO: 88; a heavy chain variable region FR4 having an amino acid sequence as set forth in SEQ ID NO: 92.

In another embodiment, the antibody, or antigen-binding fragment thereof, comprises a heavy chain variable region FR1 having an amino acid sequence as set forth in SEQ ID NO: 79; a heavy chain variable region FR2 having an amino acid sequence as set forth in SEQ ID NO: 84; a heavy chain variable region FR3 having an amino acid sequence as set forth in SEQ ID NO: 91; a heavy chain variable region FR4 having an amino acid sequence as set forth in SEQ ID NO: 92.

In another embodiment, the antibody, or antigen-binding fragment thereof, comprises a heavy chain variable region FR1 having an amino acid sequence as set forth in SEQ ID NO: 79; a heavy chain variable region FR2 having an amino acid sequence as set forth in SEQ ID NO: 84; a heavy chain variable region FR3 having an amino acid sequence as set forth in SEQ ID NO: 90; a heavy chain variable region FR4 having an amino acid sequence as set forth in SEQ ID NO: 92.

In another embodiment, the antibody, or antigen-binding fragment thereof, comprises a heavy chain variable region FR1 having an amino acid sequence as set forth in SEQ ID NO: 79; a heavy chain variable region FR2 having an amino acid sequence as set forth in SEQ ID NO: 85; a heavy chain variable region FR3 having an amino acid sequence as set forth in SEQ ID NO: 91; a heavy chain variable region FR4 having an amino acid sequence as set forth in SEQ ID NO: 92.

In another embodiment, the antibody, or antigen-binding fragment thereof, comprises a light chain variable region FR1 having an amino acid sequence as set forth in SEQ ID NO: 68; a light chain variable region FR2 having an amino acid sequence as set forth in SEQ ID NO: 69; a light chain variable region FR3 having an amino acid sequence as set forth in SEQ ID NO: 73; and a light chain variable region FR4 having an amino acid sequence as set forth in SEQ ID NO: 77.

In another embodiment, the antibody, or antigen-binding fragment thereof, comprises a light chain variable region FR1 having an amino acid sequence as set forth in SEQ ID NO: 68; a light chain variable region FR2 having an amino acid sequence as set forth in SEQ ID NO: 69; a light chain variable region FR3 having an amino acid sequence as set forth in SEQ ID NO: 74; and a light chain variable region FR4 having an amino acid sequence as set forth in SEQ ID NO: 77.

In one aspect, the antibodies and antigen-binding fragments described herein are humanized and can be any isotype including, but not limited to, an IgG1, IgG2, or IgG4.

An antigen-binding fragment can be any of those described herein including, but not limited to, a Fab fragment, a Fab', a F(ab')$_2$ fragment, an Fv fragment, an scFv fragment, a single chain binding polypeptide, a Fd fragment, a Fv fragment, a variable heavy chain, a variable light chain, a one-half antibody or a dAb fragment. In one non-limiting embodiment, the antigen-binding fragment is a scFv which can, optionally, be further fused to a human Fc.

In one aspect, the antibodies and antigen-binding fragments described herein can be modified. For example, in one embodiment, the compound can be modified to alter a pharmacokinetic property of the compound such as, for example, in vivo stability, solubility, bioavailability or half-life. Such modifications include, but are not limited to, PEGylation and/or glycosylation.

The antibodies and antigen-binding fragments described herein can be formulated for rapid or extended delivery using conventional means. In one non-limiting embodiment, rapid delivery is, for example, by intravenous injection. In another non-limiting embodiment, extended delivery is, for example, by subcutaneous deposition. In another non-limiting embodiment, delivery is achieved via administration by aerosol.

The antibodies and antigen-binding fragments described herein bind PAI-1 and/or induce a conformational change of PAI-1 to its latent form. Additionally, the antibodies and antigen-binding fragments described herein bind PAI-1 and induce transition to its substrate form. For diagnostic or therapeutic applications, the antibodies and antigen-binding fragments described herein can further comprise a detectable moiety, a therapeutic moiety or both.

Antibodies or antigen-binding fragments described herein are useful in detection or diagnostic applications as described in more detail below. Antibodies or antigen-binding fragments described herein are also useful for converting PAI-1 to its latent form or inducing a transition to its substrate form which, in turn, can accomplish one or more of the following: decrease persistence of venous and arterial thrombi, decrease atherosclerotic plaque formation, decrease or preventing renal extracellular matrix accumulation, or decrease formation or persistence of glomerular sclerosis.

Provided herein are compositions of the antibodies and antigen-binding fragments described herein and an acceptable carrier or excipient.

Provided herein are polynucleotides (nucleic acids) comprising a nucleotide sequence encoding antibodies or antigen-binding fragments described herein.

Modulation of PAI-1 represents a mechanism for the treatment, prevention or amelioration of the aforementioned conditions. Thus, there is a need for compositions and therapies which can neutralize or inhibit PAI-1. There is also a need for compositions, therapies, and methods of treatment which address diseases and conditions related to the inhibition of thrombolysis, the inhibition of tissue plasminogen activator (tPA) and urokinase plasminogen activator (uPA), and the effector pathways associated with thrombolysis and/or tPA or uPA.

The antibodies and antigen-binding fragments described herein can be used in the formulation of a medicament for the treatment prophylaxis, treatment, or diagnosis of fibrosis or thrombosis including, but not limited to, kidney fibrosis, liver fibrosis, a cancer (e.g., a primary or metastatic cancer), angiogenesis, a cardiac fibrosis, respiratory fibrosis or post-transplantation fibrosis. One or more additional anti-fibrotic or anti-thrombosis treatment regimens can be administered to a patient in combination with one or more of the antibodies or antigen-binding fragments described herein. In one embodiment, a combination of a humanized 33B8 and a humanized 55F4 antibody or antigen-binding fragment described herein.

Provided herein are methods of treating conditions or disorders in which it is beneficial to prevent interaction of PAI-1 with tPA and/or uPA by administering antibodies or antigen binding fragments that bind to PAI-1 and convert PAI-1 to its latent form.

Provided herein are methods of treating conditions or disorders in which it is beneficial to prevent interaction of PAI-1 with tPA and/or uPA by administering antibodies or antigen binding fragments that bind to PAI-1 and (1) decrease complex formation of PAI-1 with tPA and/or uPA and/or (2) increase cleavage of PAI-1.

In one aspect is a method of decreasing the inhibitory activity of PAI-1 in a subject by administering a composition of an antibody or antigen-binding fragment described herein. In another aspect is a method of neutralizing PAI-1 in a subject by administering a composition of an antibody or antigen-binding fragment described herein.

Provided herein are methods of treatment prophylaxis, or diagnosis of fibrosis or thrombosis including, but not limited to, kidney fibrosis, liver fibrosis, a cancer (e.g., a primary or metastatic cancer), angiogenesis, a cardiac fibrosis, respiratory fibrosis or post-transplantation fibrosis, multiple sclerosis, Alzheimer's disease. One or more additional anti-fibrotic or anti-thrombosis treatment regimens can be administered to a patient in combination with one or more of the antibodies or antigen-binding fragments described herein. In one embodiment, a combination of a humanized 33B8 and a humanized 55F4 antibody or antigen-binding fragments described herein is administered to a patient concurrently. Alternatively, a combination of a humanized 33B8 and a humanized 55F4 antibody or antigen-binding fragments described herein is administered to a patient sequentially.

Provided herein are methods of treatment prophylaxis, or diagnosis of liver fibrosis, by administering one or more of the antibodies or antigen-binding fragments described herein. Fibrotic conditions of the liver include, but are not limited to, cirrhosis (e.g., primary biliary cirrhosis), hepatitis C viral (HCV) infection, hepatitis B viral (HBV) infection, non-alcoholic steatohepatitis (NASH), etc.), Alcoholic liver disease (ALD), Primary sclerosing cholangitis, Autoimmune hepatitis, Hereditary hemochromatosis, and Wilson's disease. One or more additional anti-fibrotic or anti-thrombosis treatment regimens can be administered to a patient in combination with one or more of the antibodies or antigen-binding fragments described herein. In one embodiment, a combination of a humanized 33B8 and a humanized 55F4 antibody or antigen-binding fragments described herein is administered to a patient concurrently. Alternatively, a combination of a humanized 33B8 and a humanized 55F4 antibody or antigen-binding fragments described herein is administered to a patient sequentially.

In one aspect is a method of treating diabetic nephropathy in a subject by administering a composition of an antibody or antigen-binding fragment described herein. In another aspect is a method of treating insulin-resistance syndrome in a subject by administering a composition of an antibody or antigen-binding fragment described herein.

In another aspect is a method of treating glomerular sclerosis in a subject by administering a composition of an antibody or antigen-binding fragment described herein. In another aspect is a method of inhibiting the accumulation of extracellular matrix (ECM) in a kidney of a subject by administering a composition of an antibody or antigen binding fragment described herein.

In another aspect is a method of treating obesity by administering a composition of an antibody or antigen binding fragment described herein.

In another aspect is a method of treating thrombosis in a subject by administering a composition of an antibody or antigen-binding fragment described herein.

In another aspect is a method of treating a cardiovascular disease in a subject by administering a composition of an antibody or antigen-binding fragment described herein. In one non-limiting embodiment, the cardiovascular disease is selected from among ischemic heart disease, arteriosclerosis, atherosclerosis, hypertension, angina, heart attack, stroke, deep vein thrombosis, disseminated intravascular coagulation, premature myocardial infarction and coronary artery disease.

In yet another aspect, provided herein is a method for treating Alzheimer's disease by administering a composition of an antibody or antigen-binding fragment described herein.

In yet another aspect, provided herein is a method for treating multiple sclerosis (MS) by administering a composition of an antibody or antigen-binding fragment described herein.

In yet another aspect is a method of treating cancer by administering a composition of an antibody or antigen-binding fragment described herein. In one non-limiting example, the cancer treated is a tumor.

In another aspect is a method of treating idiopathic pulmonary fibrosis (IPF) in a subject comprising administering a composition of an antibody or antigen-binding fragment described herein.

In another aspect is a method of treating acute respiratory distress syndrome (ARDS) in a subject comprising administering a composition of an antibody or antigen-binding fragment described herein.

Provided herein is a method of detecting levels of PAI-1 in a sample or a subject by i) contacting an antibody or antigen binding fragment described herein with said sample or subject, and ii) detecting a complex comprising said antibody or antigen-binding fragment thereof and PAI-1. In one aspect, the antibody or antigen-binding fragment further comprises a detectable moiety. Methods of detection can occur in vitro or in vivo.

INCORPORATION BY REFERENCE

All publications and patent applications mentioned in this specification are herein incorporated by reference to the same extent as if each individual publication or patent application was specifically and individually indicated to be incorporated by reference in its entirety unless otherwise specifically noted. This application contains references to amino acid sequences which have been submitted concurrently herewith as the sequence listing text file "35364701501.txt", file size 71 KiloBytes (KB), created on Nov. 19, 2008. The aforementioned sequence listing is hereby incorporated by reference in its entirety pursuant to 37 CFR § 1.52(e)(5).

BRIEF DESCRIPTION OF THE DRAWINGS

FIG. 1 provides a humanized B3-Vκ4 variable ($V_L$) light chain having the monoclonal murine MA-33B8 $V_L$ CDRs (underlined) grafted between the framework regions (FRs) 1-3 of the human sequence B3-$V_κ$4 and a framework region 4 from the human Jκ2 sequence (SEQ ID NO: 3). Variations that can be made to the human FR1 are indicated at position 22 of the sequence utilizing the Kabat numbering system (SEQ ID NOS 4 and 56, respectively in order of appearance).

FIG. 2 provides a humanized VH1-2 variable ($V_H$) heavy chain having the monoclonal murine MA-33B8 $V_H$ CDRs (underlined) grafted between the framework regions (FRs) 1-3 of the human sequence VH1-2 and a framework region 4 from the human JH4 sequence (SEQ ID NO: 16). One or more variations that can be made to the human FRs are indicated at positions 2, 38, 46, 67, 69, 71 and 94 of the sequence utilizing the Kabat numbering system (SEQ ID NOS 116-117, respectively in order of appearance).

FIG. 3 provides an exemplary humanized version of an anti-PAI-1 antibody illustrating a humanized $V_L$ (FIG. 3A; SEQ ID NO: 3) and a humanized $V_H$ (FIG. 3B; SEQ ID NO: 17).

FIG. 4 provides an exemplary humanized version of an anti-PAI-1 antibody illustrating a humanized $V_L$ (FIG. 4A; SEQ ID NO: 3) and a humanized $V_H$ (FIG. 4B; SEQ ID NO: 18).

The 5' HindIII site and 3' XhoI site were ligated into the corresponding sites in pcDNA3.1 (+).

Figure 7:
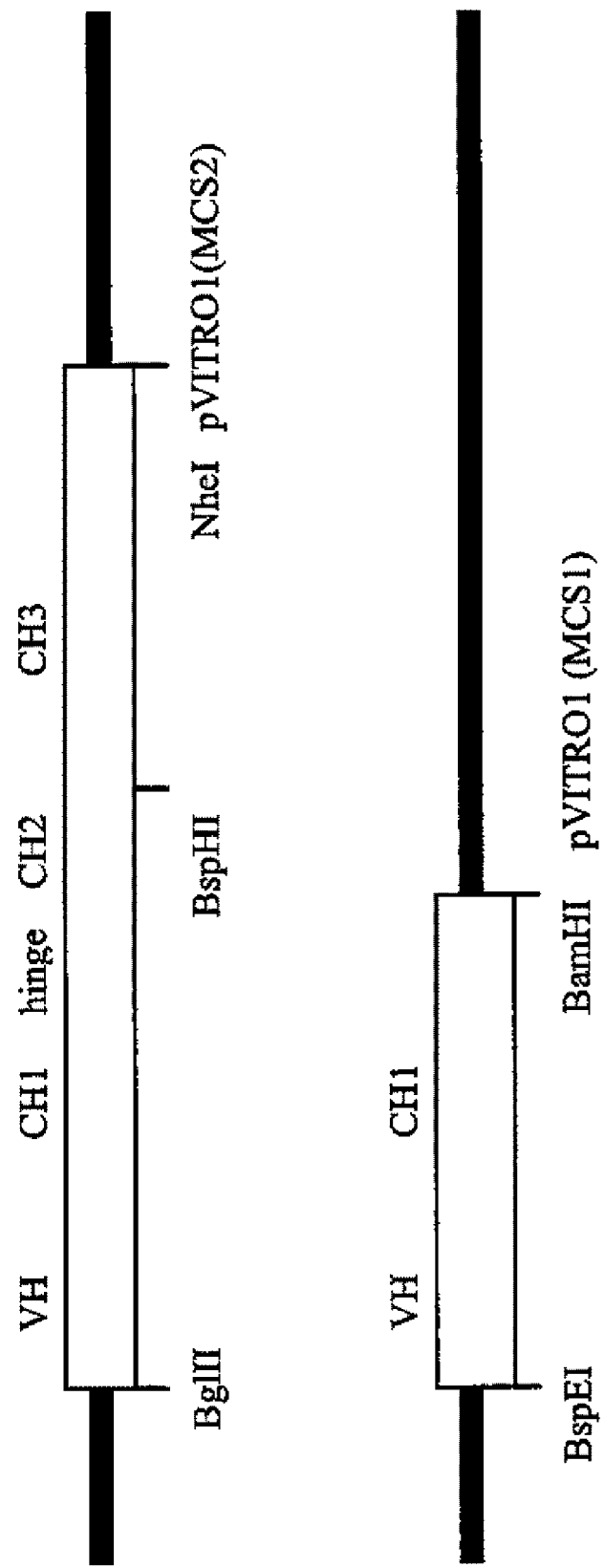

FIG. 7 Illustrates stabilization of IgG4: its hinge region was replaced with that of IgG1. Thus in a 3-way ligation (into pVITRO MCS2), a BglII to BspHI fragment of IgG1 containing the VH, CH1 and hinge region was ligated to a BspHI to NheI fragment of IgG4 containing the IgG4 Fc region.

FIG. 8 Provides the amino acid sequences of the heavy chain of CT110 which is a humanized version of murine monoclonal antibody 33B8 variable heavy chain fused to an IgG1 Fc construct (SEQ ID NO: 99; FIG. 8A); the amino acid sequences of heavy chain of CT140 which is a humanized version of murine monoclonal antibody 33B8 variable heavy chain fused to an IgG4 Fc construct (SEQ ID NO: 100; FIG. 8B); and the variable light chain (SEQ ID NO: 101; FIG. 8C) used in association with the heavy chain of CT110 or CT140.

FIG. 9 Provides a humanized 55F4C12 variable heavy (VH) chain having the murine monoclonal MA-55F4 VH CDRs (underlined) grafted between the FRs of VH1-f (SEQ ID NO: 64). Variations that can be made to the human FRs are indicated at one or more of positions 27, 28, 29, 30, 38, 48, 66, 67, 93 and 94 of the sequence utilizing the Kabat numbering system (SEQ ID NO: 118).

FIG. 10 Provides a humanized 55F4C12 variable light (VL) chain having the murine monoclonal MA-55F4 VL CDRs (underlined) grafted between the FRs of O8-Vκ1-Jκ4 (SEQ ID NO: 62). Variations that can be made to the human FRs are indicated at one or more of positions 43, 44, 71 and 87 of the sequence utilizing the Kabat numbering system (SEQ ID NO: 119).

Figure 11:
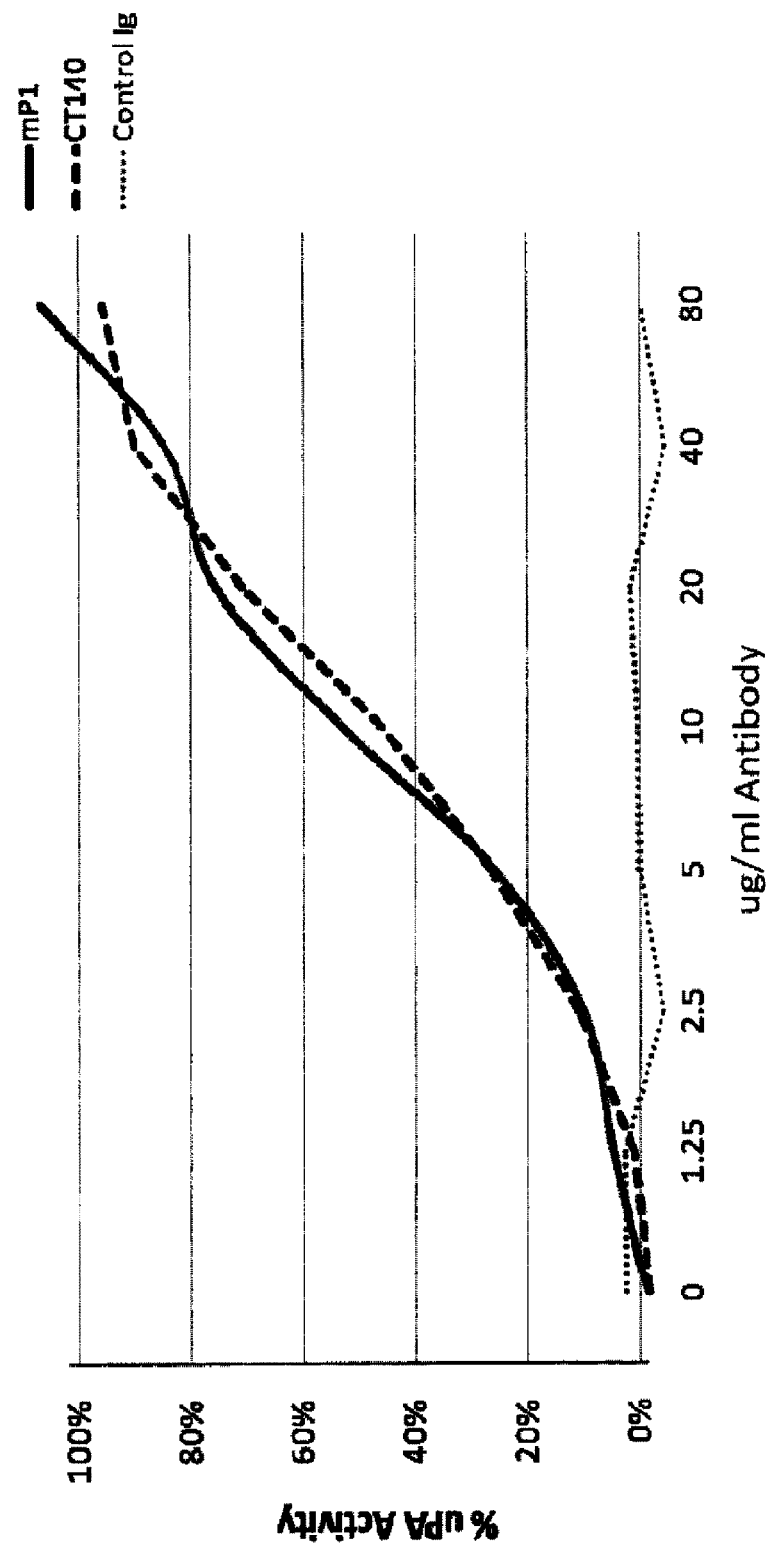

FIG. 11 Demonstrates that anti-PAI-1 antibody CT140 was found to neutralize uPA to an extent similar the murine monoclonal antibody 33B8.

Figure 12:
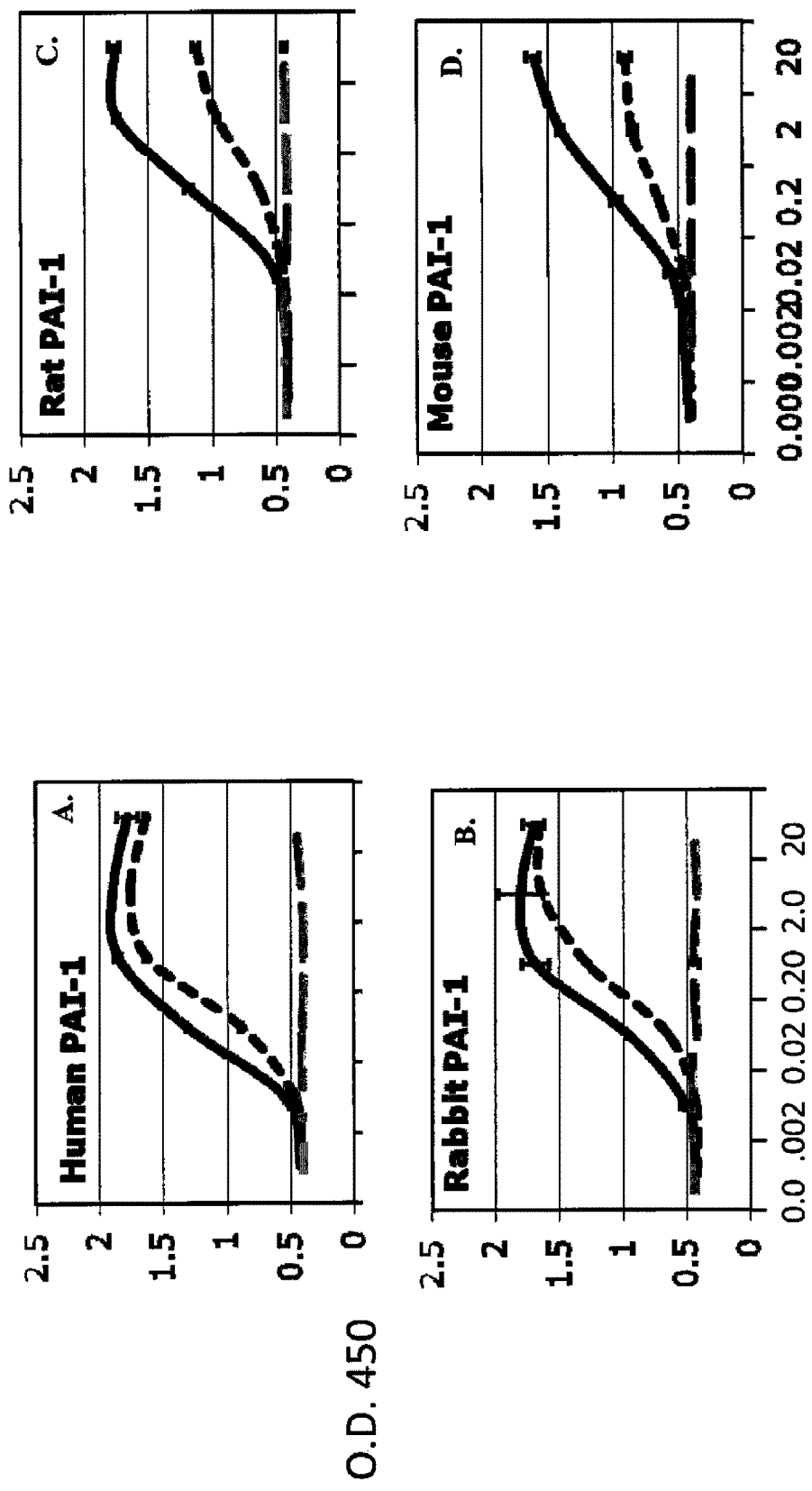

FIG. 12 Demonstrates that binding of CT140 to rat, mouse, rabbit and human PAI-1 was determined by P-ELISA. The relative affinity of CT140 is human=rabbit>mouse>rat (FIG. 12A, FIG. 12B, FIG. 12C and FIG. 12D, respectively). In the graphs, CT140 is represented by the solid lines; mP1 is represented by the short dashed lines and control IgG4 is represented by the long dashed lines.

Figure 13:
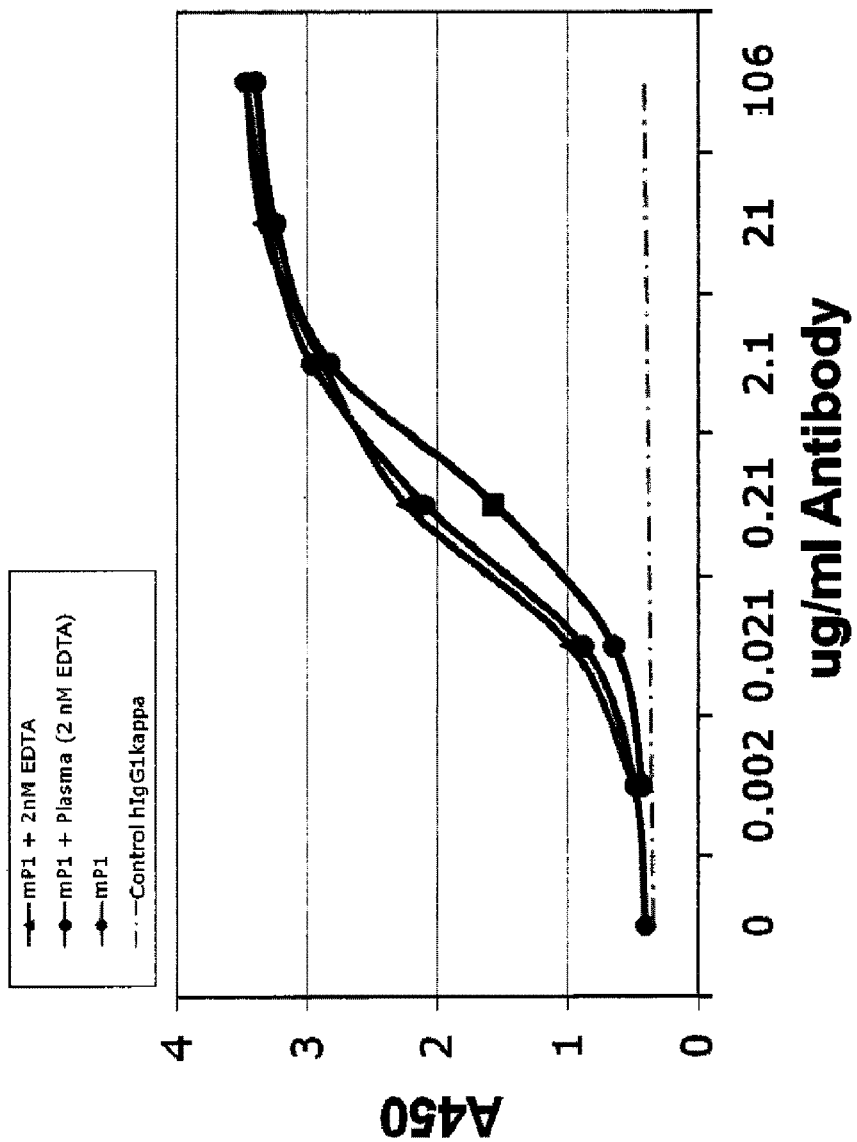

FIG. 13 Demonstrates that a PAI-1 antibody can be detected in plasma. The P-ELISA was able to detect PAI-1 antibody in spiked plasma samples (black, closed circle "●"). A P-ELISA therefore may be used to monitor plasma levels of PAI-1 antibodies in PK and efficacy studies.

Figure 14:
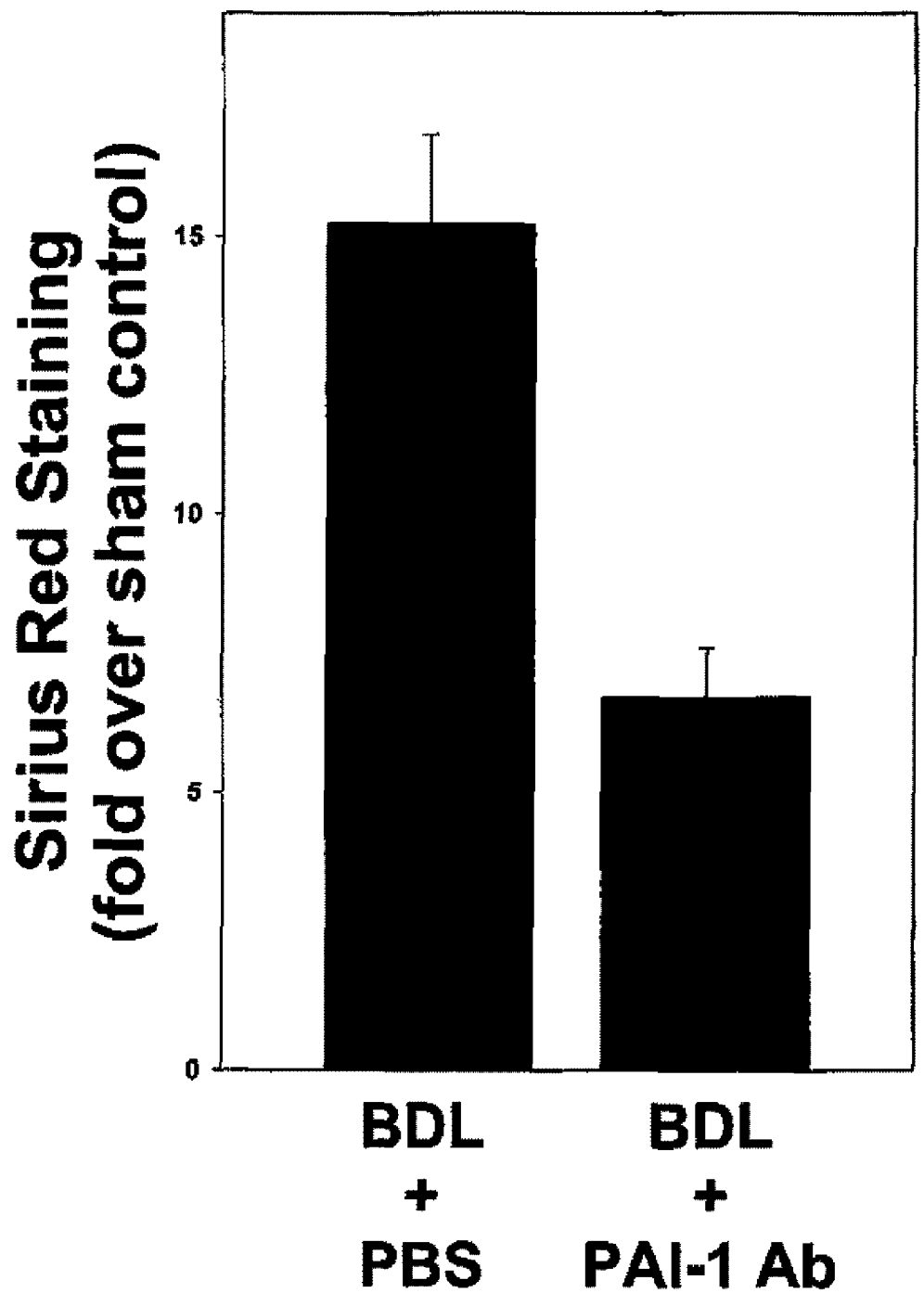

FIG. 14 Illustrates the effect of a PAI-1 neutralizing antibody, CT140, on extracellular matrix accumulation, determined by Sirius red staining, following bile duct ligation-induced liver fibrosis in mice.

Figure 15:
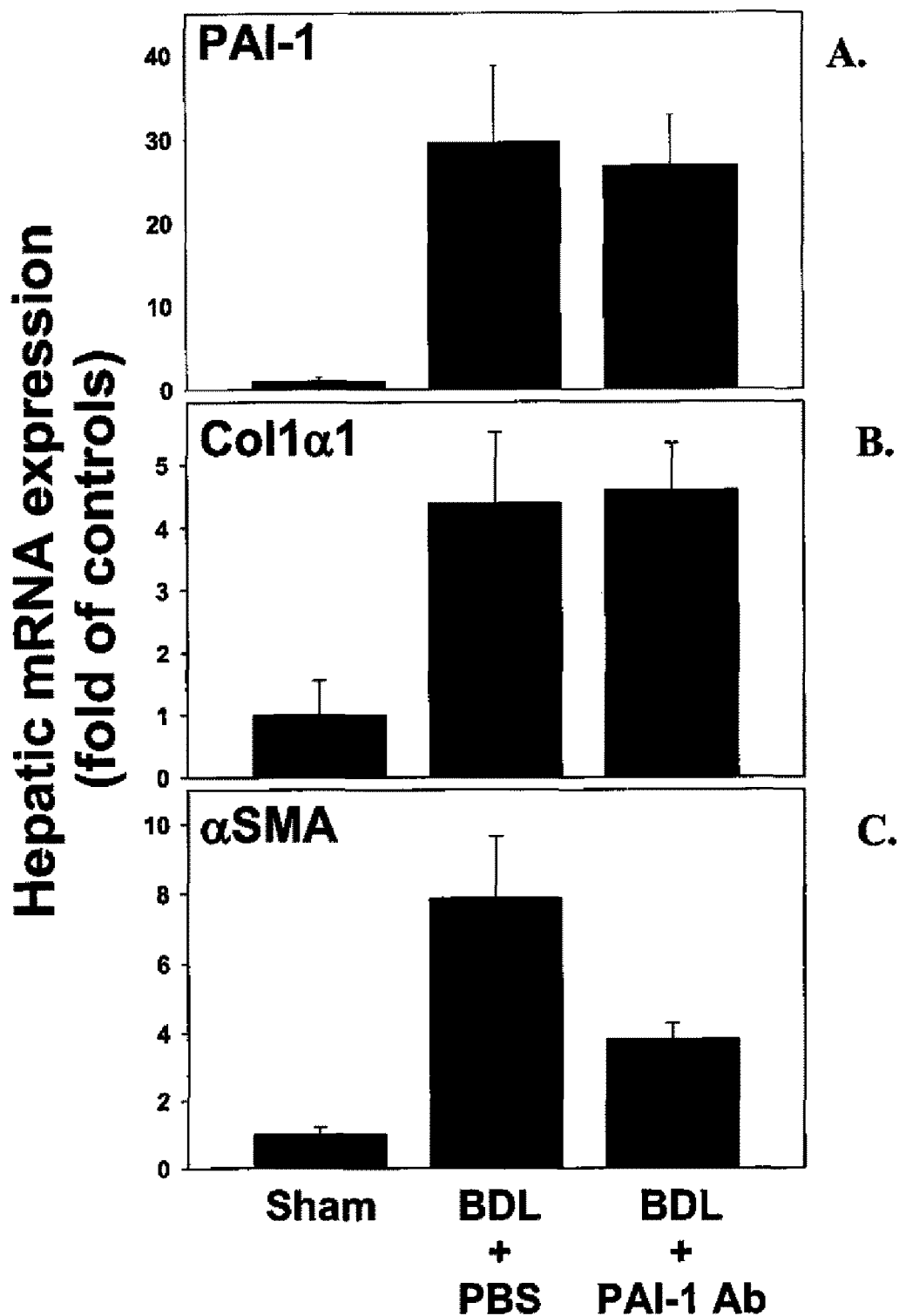

FIG. 15 Illustrates hepatic mRNA expression of PAI-1 (FIG. 15A), Col1α1 (FIG. 15B) and αSMA (FIG. 15C) identified by RT-PCR in a bile duct ligation-induced liver fibrosis mouse model.

FIG. 16 Provides an illustration of exemplary humanized antibody sequences of the variable light chain (FIG. 16A) and the variable heavy chain (FIG. 16B) of 55F4.

FIG. 17 Provides an illustration of exemplary humanized antibody sequences of the variable heavy chain (FIG. 17A) and the variable light chain (FIG. 17B) of 33B8.

Figure 18:
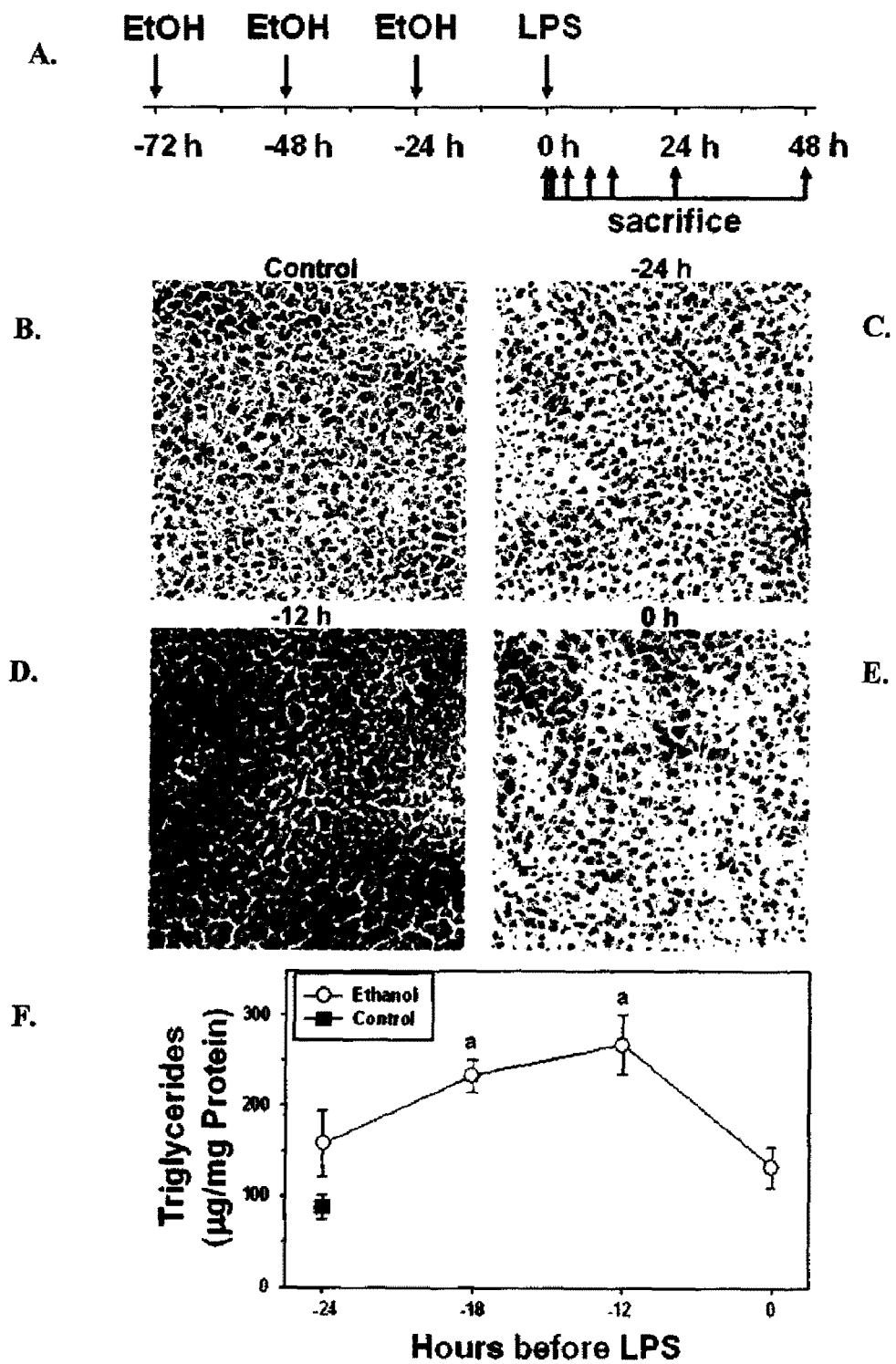

FIG. 18 demonstrates that ethanol induces steatosis in the liver. FIG. 18A describes the protocol for inducing liver injury. FIGS. 18B-E demonstrate morphology of liver sections from control animals (FIG. 18B), and from test animals at −24 hours (FIG. 18C), −12 hours (FIG. 18D) and 0 hours (FIG. 18E). FIG. 18F provides a time course of triglyceride levels, which were determined in liver samples.

Figure 19:
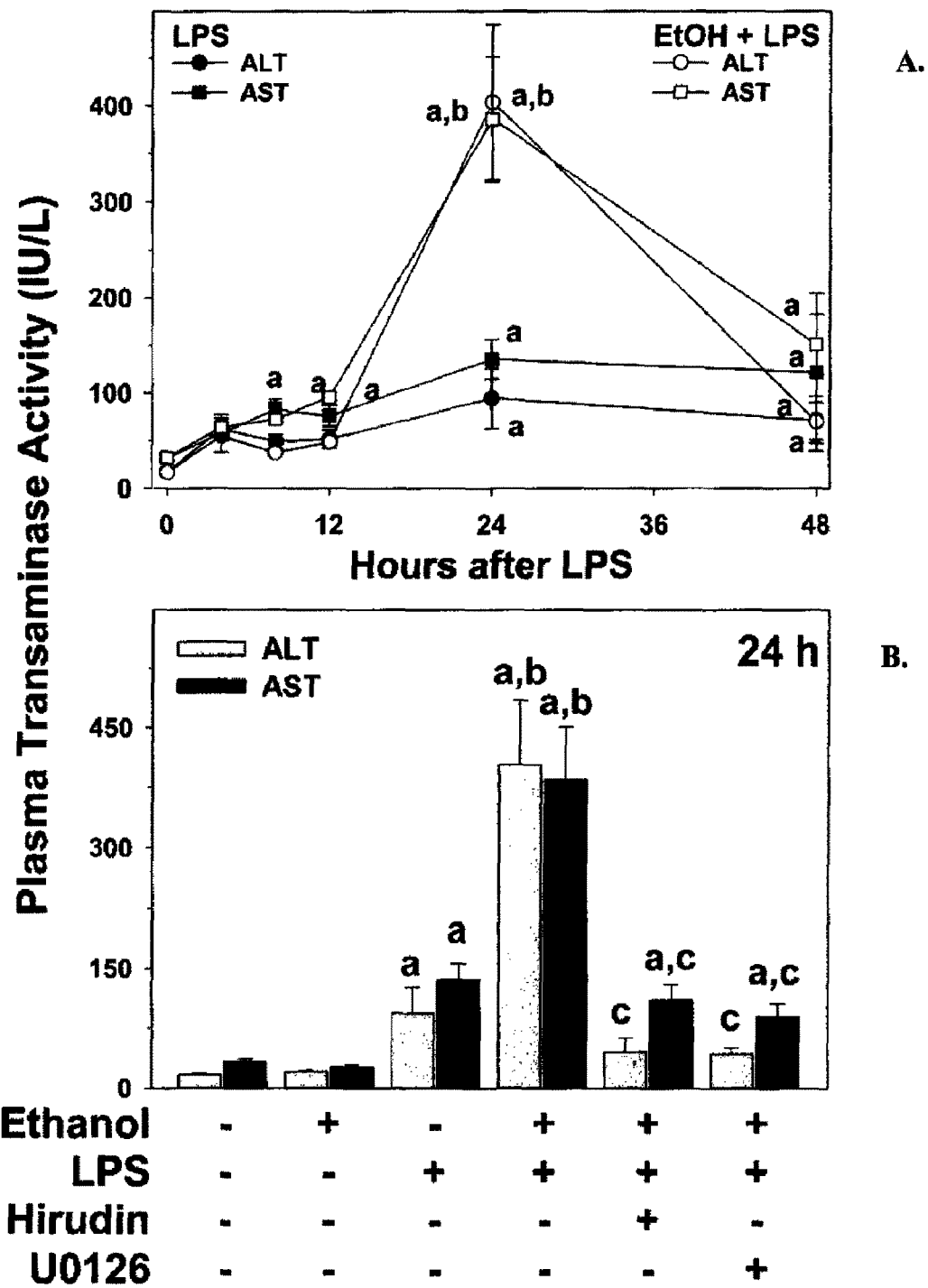

FIG. 19 demonstrates that Hirudin reduces ethanol-enhanced liver damage owing to LPS. Amino transferase levels (ALT and AST) were determined in plasma samples of different time points. The top panel (FIG. 19A) shows a time course of transaminase release of the LPS and ethanol+LPS group. The histogram in the bottom panel (FIG. 19B) compares the different groups at the peak time point (24 hours). In 19A and 19B, (a) represents an effect compared to samples lacking LPS, (b) represents an effect compared to LPS alone and (c) represents an effect compared to ethanol/LPS.

Figure 20:
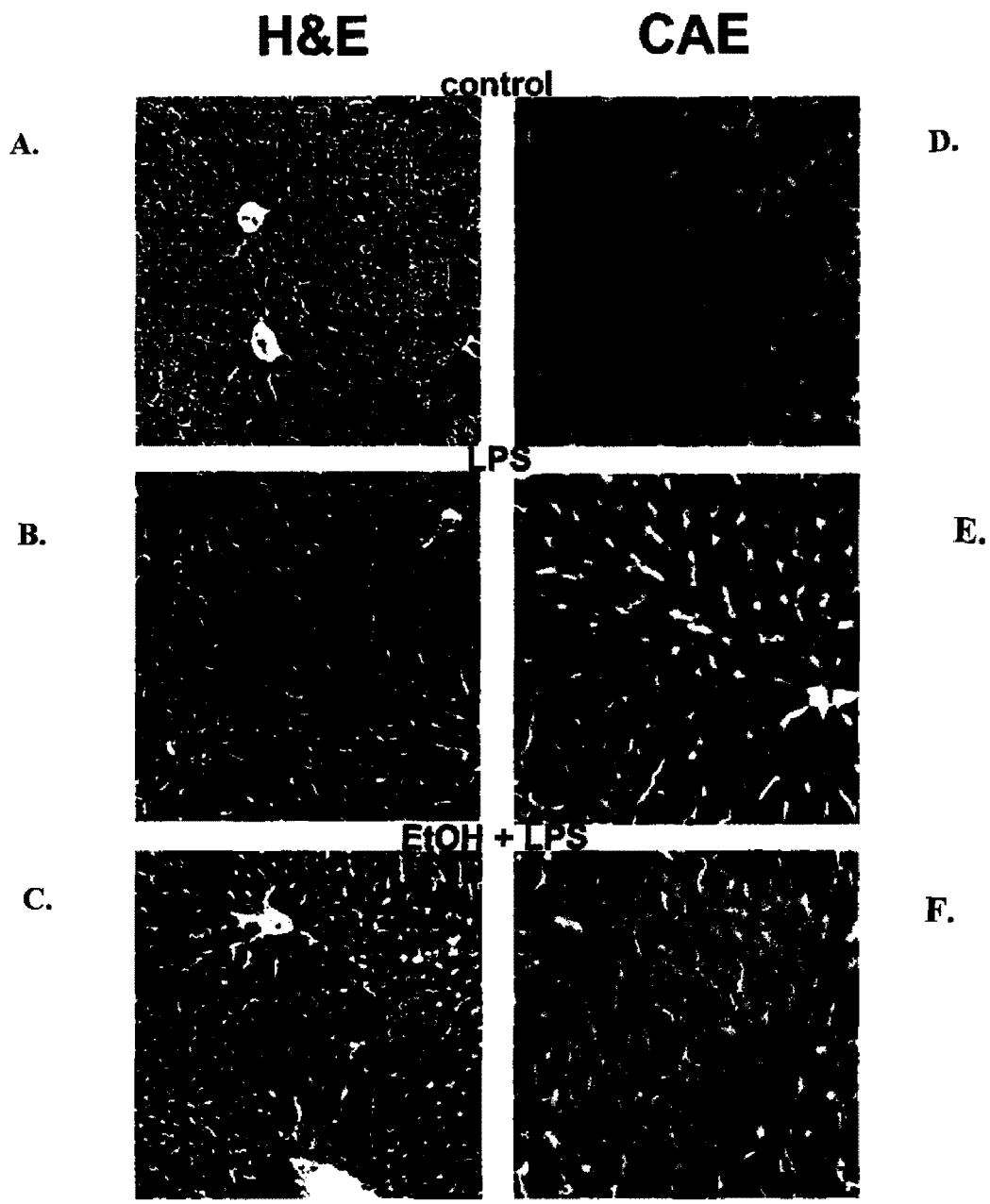

FIG. 20 provides photomicrographs of livers 24 hours after LPS and/or ethanol. Representative photomicrographs of hematoxylin and eosin (100×, H&E, left) are shown for control (FIG. 20A), LPS (FIG. 20B), and ethanol plus LPS (FIG. 20C); representative photomicrographs of chloroacetate esterase (400×, CAE, right) stains are shown for control (FIG. 20D), LPS (FIG. 20E), and ethanol plus LPS (FIG. 20F).

Figure 21:
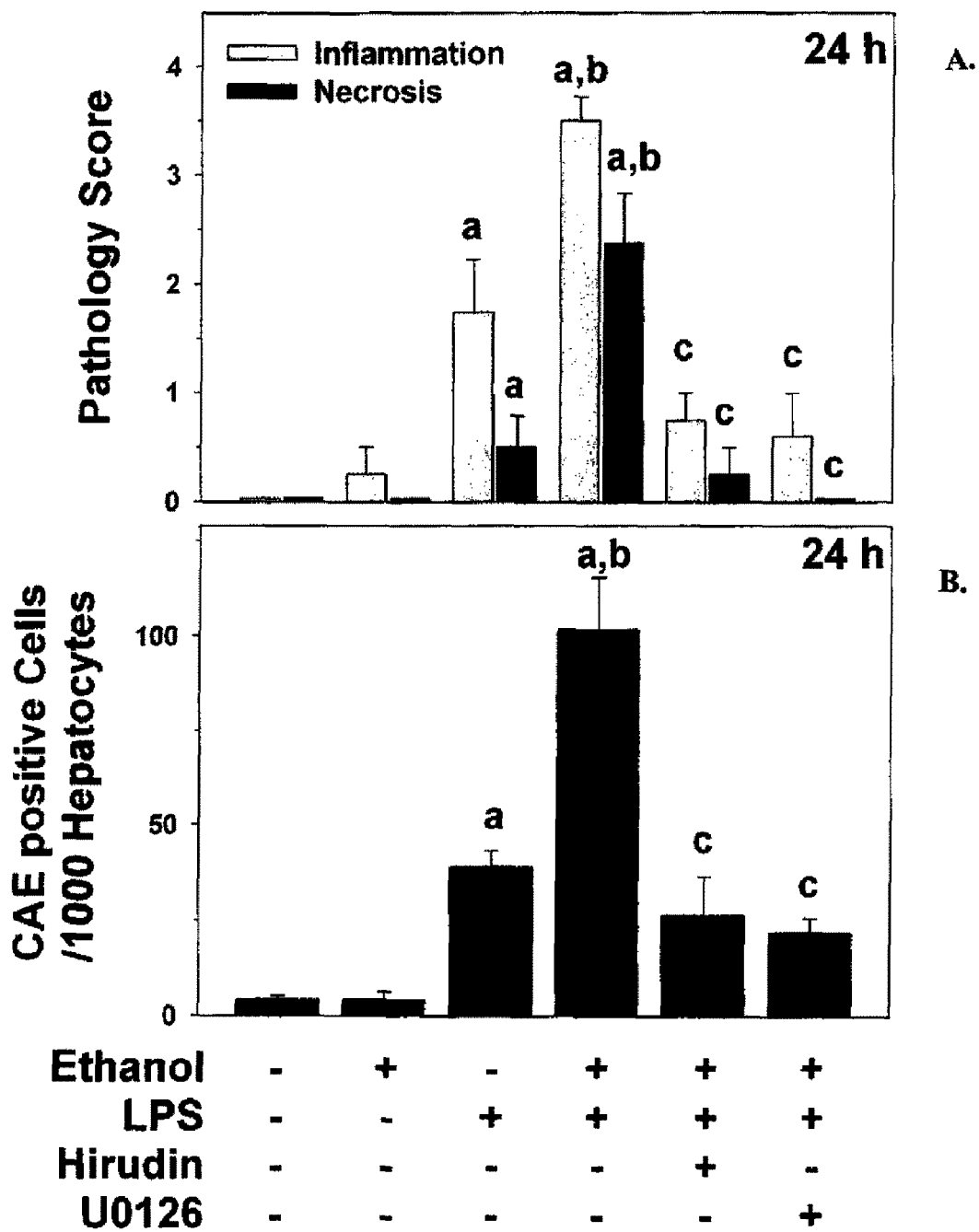
Figure 22A:
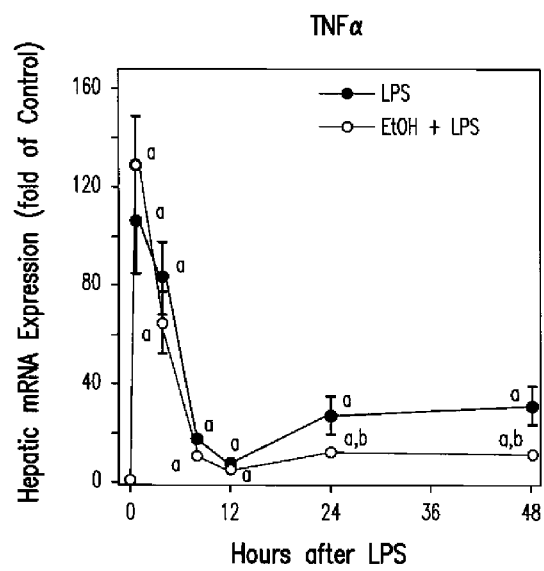
Figure 22B:
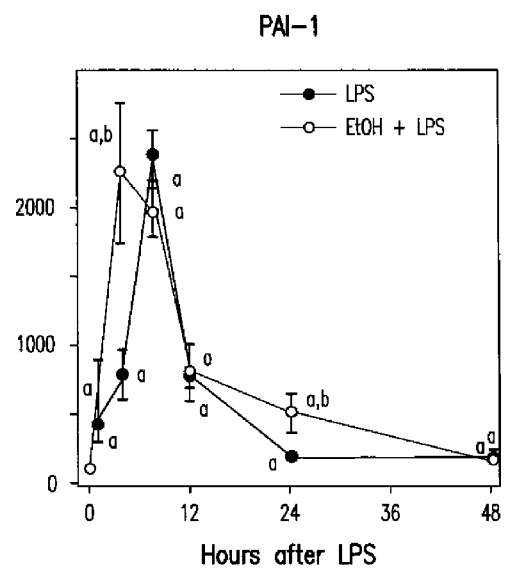
Figure 22C:
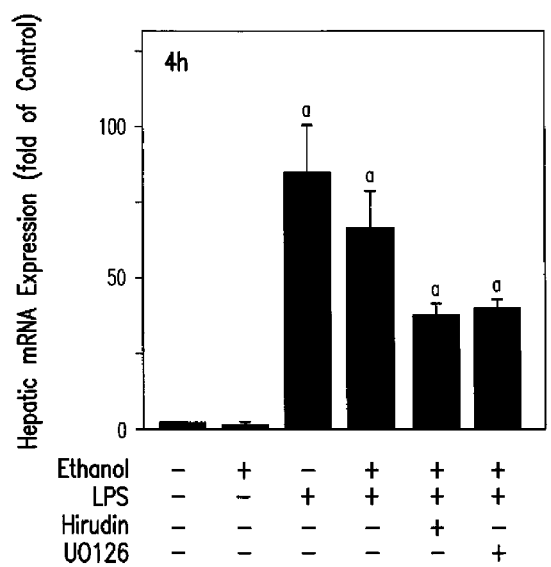
Figure 22D:
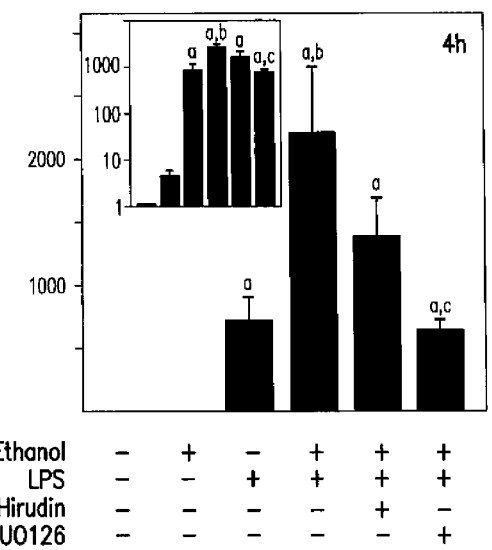

FIG. 21 illustrates the effect of ethanol and LPS on inflammation and necrosis. Pathology was scored (FIG. 21A) and CAE-positive cells were counted (FIG. 21B) at 24 hours. In 21A and 21B, (a) represents an effect compared to samples lacking LPS, (b) represents an effect compared to LPS alone and (c) represents an effect compared to ethanol/LPS.

FIG. 22 depicts the effect of Hirudin on the ethanol and LPS induced expression of pro-inflammatory genes in mouse liver. Gene expression was determined by real-time RT-PCR. The top panels depict a time course of gene expression of TNFα (FIG. 22A) and PAI-1 (FIG. 22B) for the LPS and ethanol+LPS group. The bottom panels compare the different groups (FIGS. 22C and 22D, respectively) at the peak time point of PAI-1 expression (4 hours). In each of the panels (where designated), (a) represents an effect compared to samples lacking LPS, (b) represents an effect compared to LPS alone and (c) represents an effect compared to ethanol/LPS.

Figure 23:
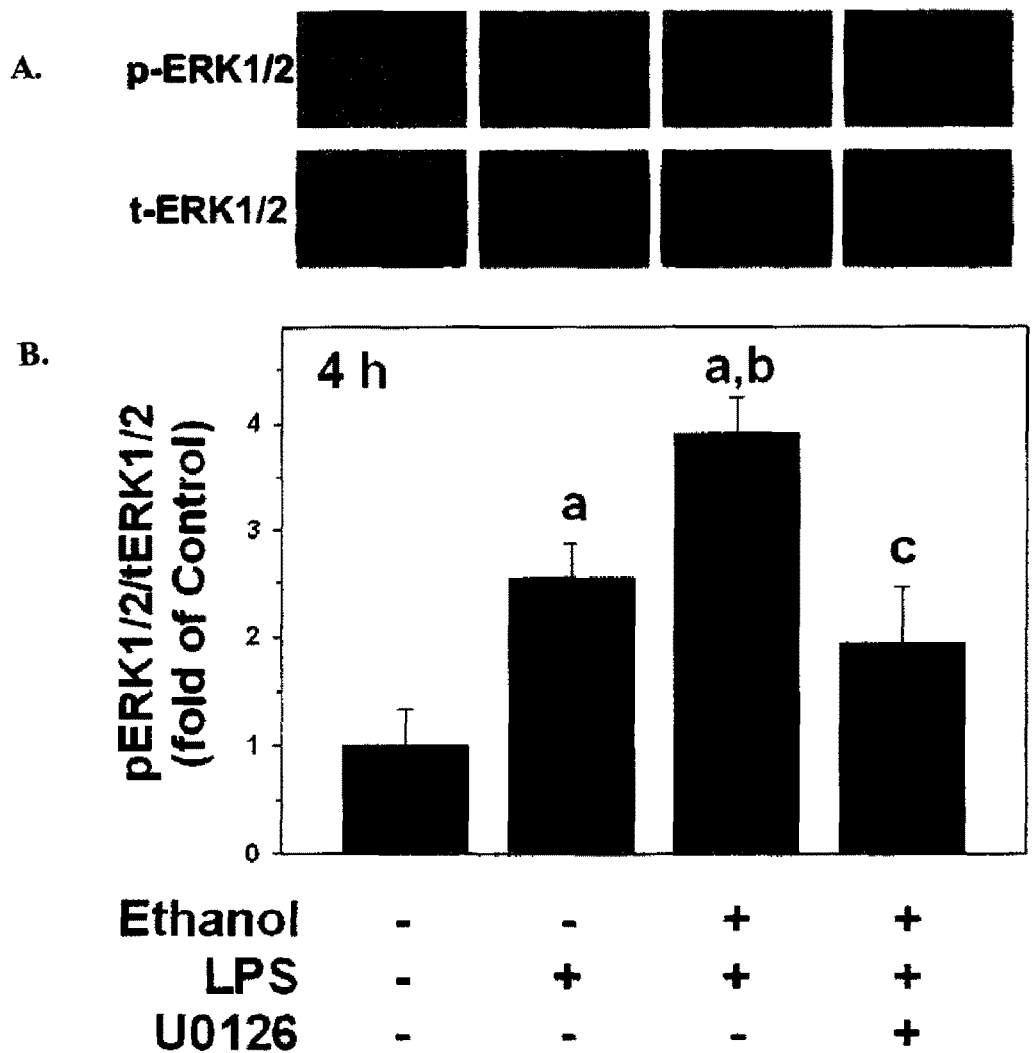

FIG. 23 demonstrates the effect of ethanol and LPS on ERK1/2 phosphorylation in mouse liver. Total and phosphor-ERK were determined by Western blot. Representative blots at the 4 h time point are shown in the top panel (FIG. 23A). Densitometric analysis is summarized in the bottom panel (FIG. 23B). In 23B, (a) represents an effect compared to samples lacking LPS, (b) represents an effect compared to LPS alone and (c) represents an effect compared to ethanol/LPS.

Figure 24:
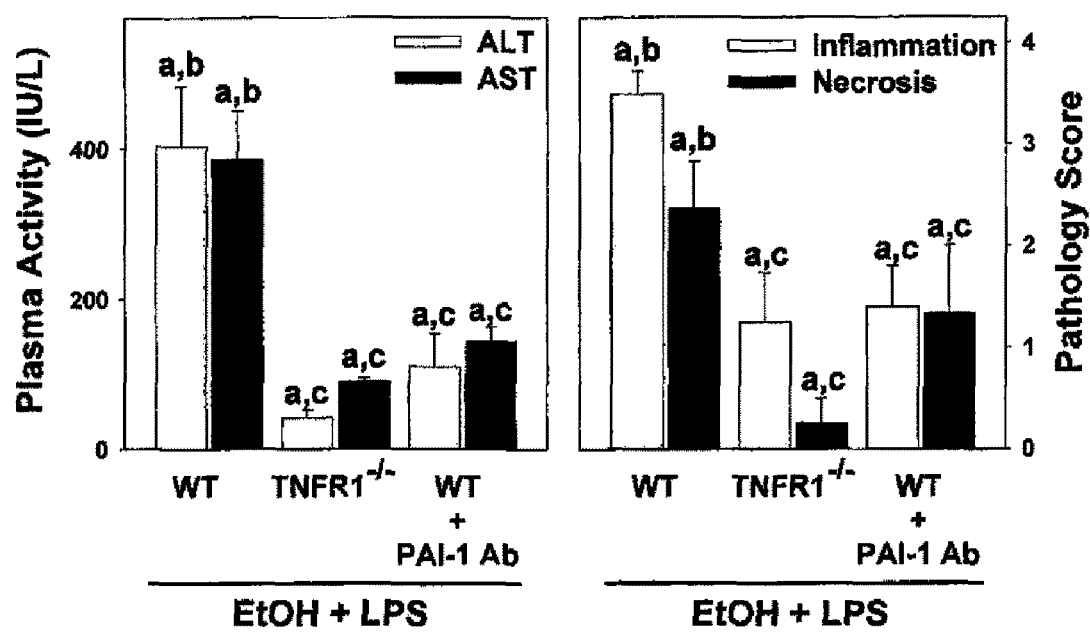

FIG. 24 illustrates the effect of ethanol and LPS on livers of control mice versus mice treated with anti-PAI-1 antibody. Plasma transaminase activity (FIG. 24A) and pathology scores (FIG. 24B) are provided. In 24A and 24B, (a) represents an effect compared to samples lacking LPS, (b) represents an effect compared to LPS alone and (c) represents an effect compared to ethanol/LPS.

DETAILED DESCRIPTION OF THE INVENTION

It is to be understood that this application is not limited to particular formulations or process parameters, as these may, of course, vary. It is also to be understood that the terminology used herein is for the purpose of describing particular embodiments only, and is not intended to be limiting. Further, it is understood that a number of methods and materials similar or equivalent to those described herein can be used in the practice of the present inventions.

In accordance with the present application, there may be employed conventional molecular biology, microbiology, and recombinant DNA techniques within the skill of the art. Such techniques are explained fully in the literature. See, e.g., Sambrook et al, "Molecular Cloning: A Laboratory Manual"

(1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984), each of which is specifically incorporated herein by reference in its entirety.

Murine monoclonal antibodies (mAbs) have been raised against PAI-1 which inhibit PAI-1 activity, [Verbeke K, Gils A, Declerck P J. Inhibition of plasminogen activator inhibitor-1: antibody fragments and their unique sequences as a tool for the development of profibrinolytic drugs. *J Thromb Haemost* 2004; 2: 298-305]. Monoclonal antibodies can inhibit PAI-1 activity through one of at least three different mechanisms: (i) prevention of the formation of the PAI-1/tPA or PAI-1/uPA complex; (ii) acceleration of the PAI-1 latency conversion; Or (iii) inducing a substrate behavior of PAI-1. In the past, the ex vivo and in vivo efficiency of a number of these antibodies has been demonstrated; these monoclonal antibodies that bind PAI-1 are of interest as PAI-1 modulating compounds. Therapeutic use of these murine antibodies is not feasible, however, as their administration has a number of limitations, including immunogenicity in, for example, the form of human anti-mouse antibodies (HAMA).

To address problems associated with murine antibodies, humanized antibodies that bind PAI-1 and increase the conversion of PAI-1 from its active form to its latent form were created that exhibit reduced immunogenicity while maintaining and/or improving their specificity. Additionally, to address problems associated with murine antibodies, humanized antibodies that bind PAI-1 and decrease complex formation between PAI-1 and its target proteinases and increase cleavable PAI-1 were created that exhibit reduced immunogenicity while maintaining and/or improving their specificity. These humanized PAI-1 antibodies are useful for the diagnosis and treatment of various conditions and diseases as well as for purification and detection of PAI-1.

I. Anti-PAI-1 Antibodies

Provided herein are humanized antibodies, and antigen-binding fragments thereof that bind PAI-1. These antibodies and antigen-binding fragments can inhibit and/or neutralize PAI-1 by increasing the conversion of active PAI-1 to latent PAI-1. These antibodies can also inhibit and/or neutralize PAI-1 by decreasing complex formation between PAI-1 and its target proteinases and by increasing cleavable PAI-1. Hereinafter, a reference to the terms "antibody" or "antibodies" are to be considered inclusive of any of the antigen-binding fragments described herein and the terms are to be interchangeable where applicable. In addition to their use for purification of PAI-1, these antibodies are useful for purification, detection and diagnostic purposes as well as therapeutic purposes. The antibodies provided herein can be used for the formulation of medicaments for the treatment a variety of conditions and diseases, methods to treat said conditions and diseases and methods of detection or diagnosis. Non-limiting examples of conditions and diseases include cardiovascular diseases (e.g., artherosclerotic plaques, restonotic lesions and venous thromboembolism) and diabetes-associated complications (e.g., diabetic nephropathy, obesity and insulin-resistance syndrome).

A. Antibody Terminology

As used herein, the term "antibody" refers to an immunoglobulin (Ig) whether natural or partly or wholly synthetically produced. The term also covers any polypeptide or protein having a binding domain which is, or is homologous to, an antigen-binding domain. The term further includes "antigen-binding fragments" and other interchangeable terms for similar binding fragments such as described below. Complementarity determining region (CDR) grafted antibodies and other humanized antibodies (including CDR modifications and framework region modifications) are also contemplated by this term.

Native antibodies and native immunoglobulins are usually heterotetrameric glycoproteins of about 150,000 Daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("$V_H$") followed by a number of constant domains ("$C_H$"). Each light chain has a variable domain at one end ("$V_L$") and a constant domain ("$C_L$") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The terms "synthetic polynucleotide," "synthetic gene" or "synthetic polypeptide," as used herein, mean that the corresponding polynucleotide sequence or portion thereof, or amino acid sequence or portion thereof, is derived, from a sequence that has been designed, or synthesized de novo, or modified, compared to an equivalent naturally-occurring sequence. Synthetic polynucleotides (antibodies or antigen binding fragments) or synthetic genes can be prepared by methods known in the art, including but not limited to, the chemical synthesis of nucleic acid or amino acid sequences. Synthetic genes are typically different from naturally-occurring genes, either at the amino acid, or polynucleotide level, (or both) and are typically located within the context of synthetic expression control sequences. For example, synthetic gene sequences can include amino acid, or polynucleotide, sequences that have been changed, for example, by the replacement, deletion, or addition, of one or more, amino acids, or nucleotides, thereby providing an antibody amino acid sequence, or a polynucleotide coding sequence that is different from the source sequence. Synthetic gene polynucleotide sequences, may not necessarily encode proteins with different amino acids, compared to the natural gene; for example, they can also encompass synthetic polynucleotide sequences that incorporate different codons but which encode the same amino acid (i.e., the nucleotide changes represent silent mutations at the amino acid level).

With respect to antibodies, the term "variable domain" refers to the variable domains of antibodies that are used in the binding and specificity of each particular antibody for its particular antigen. However, the variability is not evenly distributed throughout the variable domains of antibodies. Rather, it is concentrated in three segments called hypervariable regions (also known as CDRs) in both the light chain and the heavy chain variable domains. More highly conserved portions of variable domains are called the "framework regions" or "FRs." The variable domains of unmodified heavy and light chains each contain four FRs (FR1, FR2, FR3 and FR4), largely adopting a β-sheet configuration interspersed with three CDRs which form loops connecting and, in some cases, part of the β-sheet structure. The CDRs in each chain are held together in close proximity by the FRs and, with the CDRs from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669).

The terms "hypervariable region" and "CDR" when used herein, refer to the amino acid residues of an antibody which are responsible for antigen-binding. The CDRs comprise amino acid residues from three sequence regions which bind in a complementary manner to an antigen and are known as CDR1, CDR2, and CDR3 for each of the $V_H$ and $V_L$ chains. In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3) according to Kabat et al., Sequences of Proteins of Immunological Interest, 5th Ed. Public Health Service, National Institutes of Health, Bethesda, Md. (1991)). It is understood that the CDRs of different antibodies may contain insertions, thus the amino acid numbering may differ. The Kabat numbering system accounts for such insertions with a numbering scheme that utilizes letters attached to specific residues (e.g., 27A, 27B, 27C, 27D, 27E, and 27F of CDRL1 in the light chain) to reflect any insertions in the numberings between different antibodies. Alternatively, in the light chain variable domain, the CDRs typically correspond to approximately residues 26-32 (CDRL1), 50-52 (CDRL2) and 91-96 (CDRL3), and in the heavy chain variable domain, the CDRs typically correspond to approximately residues 26-32 (CDRH1), 53-55 (CDRH2) and 96-101 (CDRH3) according to Chothia and Lesk, J. Mol. Biol., 196: 901-917 (1987)).

As used herein, "framework region" or "FR" refers to framework amino acid residues that form a part of the antigen binding pocket or groove. In some embodiments, the framework residues form a loop that is a part of the antigen binding pocket or groove and the amino acids residues in the loop may or may not contact the antigen. Framework regions generally comprise the regions between the CDRs. In the light chain variable domain, the FRs typically correspond to approximately residues 0-23 (FRL1), 35-49 (FRL2), 57-88 (FRL3), and 98-109 and in the heavy chain variable domain the FRs typically correspond to approximately residues 0-30 (FRH1), 36-49 (FRH2), 66-94 (FRH3), and 103-133 according to Kabat et al., Sequences of Proteins of Immunological Interest, 5th Ed. Public Health Service, National Institutes of Health, Bethesda, Md. (1991)). As discussed above with the Kabat numbering for the light chain, the heavy chain too accounts for insertions in a similar manner (e.g., 35A, 35B of CDRH1 in the heavy chain). Alternatively, in the light chain variable domain, the FRs typically correspond to approximately residues 0-25 (FRL1), 33-49 (FRL2) 53-90 (FRL3), and 97-109 (FRL4), and in the heavy chain variable domain, the FRs typically correspond to approximately residues 0-25 (FRH1), 33-52 (FRH2), 56-95 (FRH3), and 102-113 (FRH4) according to Chothia and Lesk, J. Mol. Biol., 196: 901-917 (1987)).

The loop amino acids of a FR can be assessed and determined by inspection of the three-dimensional structure of an antibody heavy chain and/or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g., structural positions) are, generally, less diversified. The three dimensional structure of the antibody variable domain can be derived from a crystal structure or protein modeling.

Constant domains (Fc) of antibodies are not involved directly in binding an antibody to an antigen but, rather, exhibit various effector functions, such as participation of the antibody in antibody-dependent cellular toxicity via interactions with, for example, Fc receptors (FcR). Fc domains can also increase bioavailability of an antibody in circulation following administration to a patient.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains (Fc) that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("κ") and lambda or ("λ"), based on the amino acid sequences of their constant domains.

The terms "antigen-binding portion of an antibody," "antigen-binding fragment," "antigen-binding domain," "antibody fragment" or a "functional fragment of an antibody" are used interchangeably herein to refer to one or more fragments of an antibody that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment containing two Fab fragments linked by a disulfide bridge at the hinge region; (iii) a Fd fragment consisting of the $V_H$ and $C_{H1}$ domains; (iv) a Fv fragment containing the $V_L$ and $V_H$ domains of a single arm of an antibody, (v) a dAb fragment (Ward et al., (1989) Nature 341:544 546), which containing a $V_H$ domain; and (vi) an isolated CDR. Additionally included in this definition are "one-half" antibodies comprising a single heavy chain and a single light chain. Other forms of single chain antibodies, such as diabodies are also encompassed herein.

"F(ab')$_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which an light chain composed of $V_L$ and $C_L$ (light chain constant region), and a heavy chain fragment composed of $V_H$ and $C_{H\gamma1}$ (γ1 region in the constant region of the heavy chain) are connected at their C terminal regions through a disulfide bond. Each of these two homologous antibody fragments is called Fab'. Pepsin also cleaves IgG downstream of the disulfide bonds existing between the hinge regions in each of the two heavy chains to generate an antibody fragment slightly larger than the fragment in which the two above-mentioned Fab' are connected at the hinge region. This antibody fragment is called F(ab')$_2$.

The Fab fragment also contains the constant domain of the light chain and the first constant domain ($C_H1$) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" refers to an antibody fragment which contains a complete antigen-recognition and antigen-binding site. This region consists of a dimer of one heavy chain and one light chain variable domain in tight, non-covalent association. It is in this configuration that the three CDRs of each variable domain interact to define an antigen-binding site on the surface of the $V_H$-$V_L$ dimer. Collectively, a combination of one or more of the CDRs from each of the $V_H$ and $V_L$ chains confer antigen-binding specificity to the antibody. For example, it would be understood that, for example, the CDRH3 and CDRL3 could be sufficient to confer antigen-binding specificity to an antibody when transferred to $V_H$ and $V_L$ chains of a recipient antibody or antigen-binding fragment thereof and this combination of CDRs can be tested for binding, affinity, etc. using any of the techniques described herein. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment ($V_L$ and $V_H$), are coded for by separate genes, they can be joined using recombinant methods by a synthetic linker that enables them to be made as a single protein chain in which the $V_L$ and $V_H$ regions pair to form monovalent molecules (known as single chain Fv (scFv); Bird et al. (1988) Science 242:423-426; Huston et al. (1988) Proc. Natl. Acad. Sci. USA 85:5879-5883; and Osbourn et al. (1998) Nat. Biotechnol. 16:778). Such scFvs are also intended to be encompassed within the term "antigen-binding portion" of an antibody. Any $V_H$ and $V_L$ sequences of specific scFv can be linked to an Fc region cDNA or genomic sequences, in order to generate expression vectors encoding complete Ig (e.g., IgG) molecules or other isotypes. $V_H$ and $V_L$ can also be used in the generation of Fab, Fv or other fragments of Igs using either protein chemistry or recombinant DNA technology.

"Single-chain Fv" or "sFv" antibody fragments comprise the $V_H$ and $V_L$ domains of an antibody, wherein these domains are present in a single polypeptide chain. In some embodiments, the Fv polypeptide further comprises a polypeptide linker between the $V_H$ and $V_L$ domains which enables the sFv to form the desired structure for antigen binding. For a review of sFvs see, e.g., Pluckthun in The Pharmacology of Monoclonal Antibodies, Vol. 113, Rosenburg and Moore eds. Springer-Verlag, New York, pp. 269-315 (1994).

The term "Avimer™" refers to a class of therapeutic proteins of human origin, which are unrelated to antibodies and antibody fragments, and are composed of several modular and reusable binding domains, referred to as A-domains (also referred to as class A module, complement type repeat, or LDL-receptor class A domain). They were developed from human extracellular receptor domains by in vitro exon shuffling and phage display (Silverman et al., 2005, Nat. Biotechnol. 23:1493-1494; Silverman et al., 2006, Nat. Biotechnol. 24:220). The resulting proteins can contain multiple independent binding domains that can exhibit improved affinity (in some cases, sub-nanomolar) and specificity compared with single-epitope binding proteins. See, for example, U.S. Patent Application Publ. Nos. 2005/0221384, 2005/0164301, 2005/0053973 and 2005/0089932, 2005/0048512, and 2004/0175756, each of which is hereby incorporated by reference herein in its entirety.

Each of the known 217 human A-domains comprises ~35 amino acids (~4 kDa); and domains are separated by linkers that average five amino acids in length. Native A-domains fold quickly and efficiently to a uniform, stable structure mediated primarily by calcium binding and disulfide formation. A conserved scaffold motif of only 12 amino acids is required for this common structure. The end result is a single protein chain containing multiple domains, each of which represents a separate function. Each domain of the proteins binds independently and the energetic contributions of each domain are additive. These proteins were called "Avimers™" from avidity multimers.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/111161; and Hollinger et al., Proc. Natl. Acad. Sci. USA 90:6444 6448 (1993).

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the $V_H$ or $V_{HH}$ regions. The CDR3 in the camel $V_{HH}$ region is characterized by its relatively long length, averaging 16 amino acids (Muyldermans et al., 1994, Protein Engineering 7(9): 1129). This is in contrast to CDR3 regions of antibodies of many other species. For example, the CDR3 of mouse $V_H$ has an average of 9 amino acids. Libraries of camelid-derived antibody variable regions, which maintain the in vivo diversity of the variable regions of a camelid, can be made by, for example, the methods disclosed in U.S. Patent Application Ser. No. 20050037421.

"Humanized" forms of non-human (e.g., murine) antibodies include chimeric antibodies which contain minimal sequence derived from a non-human Ig. For the most part, humanized antibodies are human Igs (recipient antibody) in which one or more of the CDRs of the recipient are replaced by CDRs from a non-human species antibody (donor antibody) such as mouse, rat, rabbit or non-human primate having the desired specificity, affinity and binding function. In some instances, one or more FR amino acid residues of the human Ig are replaced by corresponding non-human amino acid residues. Furthermore, humanized antibodies can contain residues which are not found in the recipient antibody or in the donor antibody. These modifications can be made to refine antibody performance, if needed. A humanized antibody can comprise substantially all of at least one and, in some cases two, variable domains, in which all or substantially all of the hypervariable regions correspond to those of a non-human immunoglobulin and all, or substantially all, of the FRs are those of a human immunoglobulin sequence. The humanized antibody optionally can also include at least a portion of an immunoglobulin constant region (Fc), typically that of a human immunoglobulin. For details, see Jones et al., Nature 321: 522-525 (1986); Reichmann et al., Nature 332: 323-329 (1988); and Presta, Curr. Op. Struct. Biol. 2: 593-596 (1992).

A humanized antibody also includes antibodies in which part, or all of the CDRs of the heavy and light chain are derived from a non-human monoclonal antibody, substantially all the remaining portions of the variable regions are derived from human variable region (both heavy and light chain), and the constant regions are derived from a human constant region. In one embodiment, the CDR1, CDR2 and CDR3 regions of the heavy and light chains are derived from a non-human antibody. In yet another embodiment, at least one CDR (e.g., a CDR3) of the heavy and light chains is derived from a non-human antibody. Various combinations of CDR1, CDR2, and CDR3 can be derived from a non-human antibody and are contemplated herein. In one non-limiting example, one or more of the CDR1, CDR2 and CDR3 regions of each of the heavy and light chains are derived from a murine monoclonal antibody clone MA-33B8.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which can include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, monoclonal antibodies can be made by the hybridoma method first described by Kohler et al., Nature 256:495 (1975), or can be made by recombinant DNA methods (see, e.g., U.S. Pat. No. 4,816,567). In certain embodiments, the monoclonal antibodies can be isolated from phage antibody libraries using the techniques described in Clackson et al., Nature 352:624-628 (1991) and Marks et al., J. Mol. Biol. 222:581-597 (1991), for example.

Antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), or affinity chromatography using anti-Ig column or a protein A, G or L column such as described in more detail below.

Exemplary antibodies for use in the compositions and methods described herein are intact immunoglobulin molecules, such as, for example, a humanized antibody or those portions of a humanized Ig molecule that contain the antigen binding site (i.e., paratope) or a single heavy chain and a single light chain, including those portions known in the art as Fab, Fab', F(ab)', F(ab')$_2$, Fd, scFv, a variable heavy domain, a variable light domain, a variable NAR domain, bi-specific scFv, a bi-specific Fab$_2$, a tri-specific Fab$_3$ and a single chain binding polypeptides and others also referred to as antigen-binding fragments. When constructing an immunoglobulin molecule or fragments thereof, variable regions or portions thereof may be fused to, connected to, or otherwise joined to one or more constant regions or portions thereof to produce any of the antibodies or fragments thereof described herein. This may be accomplished in a variety of ways known in the art, including but not limited to, molecular cloning techniques or direct synthesis of the nucleic acids encoding the molecules. Exemplary non-limiting methods of constructing these molecules can also be found in the examples described herein.

In one exemplary embodiment, the application contemplates a single chain binding polypeptide having a heavy chain variable region, and/or a light chain variable region which binds PAI-1 and increases conversion of the active form to the latent form and, optionally, an immunoglobulin Fc region. In one exemplary embodiment, the application contemplates a single chain binding polypeptide having a heavy chain variable region, and/or a light chain variable region which binds PAI-1, decreases complex formation between PAI-1 and its target proteinases and increases cleavable PAI-1 and, optionally, an immunoglobulin Fc region. Such a molecule is a single chain variable fragment optionally having effector function or increased half-life through the presence of the immunoglobulin Fc region. Methods of preparing single chain binding polypeptides are known in the art (e.g., U.S. Patent Application No. 2005/0238646).

The terms "germline gene segments" or "germline sequences" refer to the genes from the germline (the haploid gametes and those diploid cells from which they are formed). The germline DNA contains multiple gene segments that encode a single Ig heavy or light chain. These gene segments are carried in the germ cells but cannot be transcribed and translated into heavy and light chains until they are arranged into functional genes. During B-cell differentiation in the bone marrow, these gene segments are randomly shuffled by a dynamic genetic system capable of generating more than $10^8$ specificities. Most of these gene segments are published and collected by the germline database.

As used herein, the term "affinity" refers to the equilibrium constant for the reversible binding of two agents and is expressed as Kd. Affinity of a binding protein to a ligand such as affinity of an antibody for an epitope can be, for example, from about 100 nanomolar (nM) to about 0.1 nM, from about 100 nM to about 1 picomolar (pM), or from about 100 nM to about 1 femtomolar (fM). As used herein, the term "avidity" refers to the resistance of a complex of two or more agents to dissociation after dilution.

"Epitope" refers to that portion of an antigen or other macromolecule capable of forming a binding interaction with the variable region binding pocket of an antibody. Such binding interactions can be manifested as an intermolecular contact with one or more amino acid residues of one or more CDRs. Antigen binding can involve, for example, a CDR3 or a CDR3 pair or, in some cases, interactions of up to all six CDRs of the $V_H$ and $V_L$ chains. An epitope can be a linear peptide sequence (i.e., "continuous") or can be composed of noncontiguous amino acid sequences (i.e., "conformational" or "discontinuous"). An antibody can recognize one or more amino acid sequences; therefore an epitope can define more than one distinct amino acid sequence. Epitopes recognized by antibodies can be determined by peptide mapping and sequence analysis techniques well known to one of skill in the art. Binding interactions are manifested as intermolecular contacts with one or more amino acid residues of a CDR. Epitopes recognized by murine monoclonal antibody MA 33B8 have been identified in two studies. A cluster of eight amino acids of PAI-1 comprising Asparagine$^{87}$, Lysine$^{88}$, Aspartic acid$^{89}$, Glutamine$^{174}$, GlyCine$^{230}$, Threonine$^{232}$, Asparagine$^{329}$ and Serine$^{331}$ were identified as the binding epitope of MA-33B8 (Gorlatova et al., "Mapping of a Conformational Epitope on Plasminogen Activator Inhibitor-1 by Random Mutagenesis," J. Biol. Chem., 278(18):16329-16335 (2003)). Similarly, another study identified the functional epitope of MA-33B8 as comprising Lysine$^{88}$, Asparagine[89], Lysine[176] and Histidine[229] of PAI-1 (Naessens et al., "Elucidation of the epitope of a latency-inducing antibody: identification of a new molecular target for PAI-1 inhibition," Thromb. Haemost., 90:52-58 (2003)).

The term "specific" refers to a situation in which an antibody will not show any significant binding to molecules other than the antigen containing the epitope recognized by the antibody. The term is also applicable where for example, an antigen binding domain is specific for a particular epitope which is carried by a number of antigens, in which case the antibody or antigen-binding fragment thereof carrying the antigen binding domain will be able to bind to the various antigens carrying the epitope. The terms "preferentially binds" or "specifically binds" mean that the antibodies or fragments thereof bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody or fragment thereof for unrelated amino acid sequences. The terms "immunoreactive," "binds," "preferentially binds" and "specifically binds" are used interchangeably herein. The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

B. Methods of Making and Expressing Humanized Anti-PAI-1 Antibodies

A murine monoclonal antibody has been developed that binds PAI-1 and increases the conversion of the active form of PAI-1 to the latent form. This antibody is designated MA-33B8 (see Verbeke et al., *Inhibition of plasminogen activator inhibitor-1: antibody fragments and their unique sequences as a tool for the development of profibrinolytic drugs*, J. Thromb. and Haemostasis, 2:298-305 (2004)). It was observed that the murine monoclonal antibody did not exhibit therapeutic effects due, in part, to immunogenicity of the murine antibody in various animal models.

In one aspect, the antibodies and antigen-binding fragments thereof described herein were created by humanization of the $V_L$ and $V_H$ sequences of the murine monoclonal MA-33B8 antibody (SEQ ID NOS. 1 and 14, respectively).

In another aspect, the antibodies and antigen-binding fragments thereof described herein were created by humanization of the $V_L$ and $V_H$ sequences of the murine monoclonal MA-55F4 antibody (SEQ ID NOS. 58 and 59, respectively).

Humanized immunoglobulins, including humanized antibodies, have been constructed by means of genetic engineering. Most humanized immunoglobulins that have been previously described have comprised a framework that is identical to the framework of a particular human immunoglobulin chain (i.e., an acceptor or recipient), and three CDRs from a non-human (donor) immunoglobulin chain. As described herein, humanization can also include criteria by which a limited number of amino acids in the framework of a humanized immunoglobulin chain are identified and chosen to be the same as the amino acids at those positions in the donor rather than in the acceptor, in order to increase the affinity of an antibody comprising the humanized immunoglobulin chain.

The present invention is based in part on the model that two contributing causes of the loss of affinity in prior means of producing humanized antibodies (using as examples mouse antibodies as the source of CDRs) are: (1) when the mouse CDRs are combined with a human framework, the amino acids in the frameworks close to the CDRs become human instead of mouse. Without intending to be bound by theory, these changed amino acids may slightly distort the CDRs (e.g., they may create different electrostatic or hydrophobic forces than in the donor mouse antibody, and the distorted-CDRs may not make as effective contacts with the antigen as the CDRs did in the donor antibody); (2) also, amino acids in the original mouse antibody that are close to, but not part of, the CDRs (i.e., still part of the framework), may make contacts with the antigen that contribute to affinity. These amino acids are lost when the antibody is humanized because, generally, all framework amino acids are made human. To circumvent these issues, and to produce humanized antibodies that have a very strong affinity for a desired antigen, humanized antibodies and antigen-binding fragments thereof can be constructed using one or more of the following principles.

One principle is that as acceptor, a framework is used from a particular human immunoglobulin that is unusually homologous to the donor immunoglobulin to be humanized, or use a consensus framework from many human antibodies is used as an acceptor. For example, comparison of the sequence of a mouse heavy (or light) chain variable region against human heavy (or light) variable regions in a data bank (for example, the National Biomedical Research Foundation Protein Identification Resource or the protein sequence database of the National Center for Biotechnology Information—NCBI) shows that the extent of homology to different human regions can vary greatly, for example from about 40% to about 60%, about 70%, about 80%, or higher. By choosing as the acceptor immunoglobulin one of the human heavy chain variable regions that is most homologous to the heavy chain variable region of the donor immunoglobulin, fewer amino acids will be changed in going from the donor immunoglobulin to the humanized immunoglobulin. By choosing as the acceptor immunoglobulin one of the human light chain variable regions that is most homologous to the light chain variable region of the donor immunoglobulin, fewer amino acids will be changed in going from the donor immunoglobulin to the humanized immunoglobulin. Generally, using such techniques, there is a reduced chance of changing an amino acid near one or more of the CDRs that distorts their conformation. Moreover, the precise overall shape of a humanized antibody comprising the humanized immunoglobulin chain may more closely resemble the shape of the donor antibody, thereby also reducing the chance of distorting the CDRS.

One can also use light and heavy chains from the same human antibody as acceptor sequences, to improve the likelihood that the humanized light and heavy chains will make favorable contacts with each other. Alternatively, one can also use light and heavy chains from different human antibody germline sequences as acceptor sequences; when such combinations are used, one can readily determine whether the $V_H$ and $V_L$ bind an epitope of interest using conventional assays (e.g., an ELISA). In one example, the human antibody will be chosen in which the light and heavy chain variable regions sequences, taken together, are overall most homologous to the donor light and heavy chain variable region sequences. Sometimes greater weight will be given to the heavy chain sequence. Regardless of how the acceptor immunoglobulin is chosen, higher affinity can, in some cases, be achieved by selecting a small number of amino acids in the framework of the humanized immunoglobulin chain to be the same as the amino acids at those positions in the donor rather than in the acceptor. Methods of affinity maturation are known in the art.

Humanized antibodies generally have at least three potential advantages over mouse or chimeric antibodies for use in human therapy. Because the effector portion of an antibody is human, it is believed to interact better with the other parts of the human immune system (e.g., destroy the target cells more efficiently by complement-dependent cytotoxicity (CDC) or antibody-dependent cellular cytotoxicity (ADCC)). Additionally, the human immune system should not recognize the framework or constant region of the humanized antibody as foreign, and therefore the antibody response against such an injected antibody should be less than against a totally foreign mouse antibody or a partially foreign chimeric antibody. Finally, mouse antibodies are known to have a half-life in the human circulation that is much shorter than the half-life of human antibodies. Humanized antibodies can, presumably, have a half-life more similar to naturally-occurring human antibodies, allowing smaller and less frequent doses to be given.

Humanization of antibodies and antigen-binding fragments thereof, can be accomplished via a variety of methods known in the art and described herein. Similarly, production of humanized antibodies can also be accomplished via methods known in the art and described herein.

Methods for modifications of framework regions are known in the art and are contemplated herein. Selection of one or more relevant framework amino acid positions to altered depends on a variety of criteria. One criterion for selecting relevant framework amino acids to change can be the relative differences in amino acid framework residues between the donor and acceptor molecules. Selection of relevant framework positions to alter using this approach has the advantage of avoiding any subjective bias in residue determination or any bias in CDR binding affinity contribution by the residue.

Another criterion that can be used for determining the relevant amino acid positions to change can be, for example, selection of framework residues that are known to be important or to contribute to CDR conformation. For example, canonical framework residues are important for CDR conformation and/or structure. Targeting of a canonical framework residue as a relevant position to change can be used to identify a more compatible amino acid residue in context with its associated donor CDR sequence.

The frequency of an amino acid residue at a particular framework position is another criterion which can be used for selecting relevant framework amino acid positions to change. For example, comparison of the selected framework with other framework sequences within its subfamily can reveal residues that occur at minor frequencies at a particular position or positions. Positions harboring less abundant residues are similarly applicable for selection as a position to alter in the acceptor variable region framework.

The relevant amino acid positions to change also can be selected, for example, based on proximity to a CDR. In certain contexts, FR residues can participate in CDR conformation and/or antigen binding. Moreover, this criterion can similarly be used to prioritize relevant positions selected by other criteria described herein. Therefore, differentiating between residues proximal and distal to one or more CDRs represents one way to reduce the number of relevant positions to change.

Other criteria for selecting relevant amino acid framework positions to alter include, for example, residues that are known or predicted to reside in a three dimensional space near the antigen-CDR interface or predicted to modulate CDR activity. Similarly, framework residues that are known to, or predicted to, form contacts between the heavy ($V_H$) and light ($V_L$) chain variable region interface can be selected. Such framework positions can affect the conformation and/or affinity of a CDR by modulating the CDR binding pocket, antigen (epitope) interaction or the $V_H$ and $V_L$ interaction. Therefore, selection of these amino acid positions for constructing a diverse population for screening of binding activity can be used to identify framework changes which replace residues having detrimental effects on CDR conformation or compensate for detrimental effects of residues occurring elsewhere in the framework.

Other framework residues that can be selected for alteration include amino acid positions that are inaccessible to solvent. Such residues are generally buried in the variable region and are, therefore, capable of influencing the conformation of the CDR or $V_H$ and $V_L$ interactions. Solvent accessibility can be predicted, for example, from the relative hydrophobicity of the environment created by the amino acid side chains of the polypeptide and/or by known three-dimensional structural data.

Following selection of relevant amino acid positions in the donor CDRs, as well as any relevant amino acid positions in the framework regions desired to be varied, amino acid changes at some or all of the selected positions can be incorporated into encoding nucleic acids for the acceptor variable region framework and donor CDRs. Altered framework or CDR sequences can be individually made and tested, or can be sequentially or simultaneously combined and tested.

The variability at any or all of the altered positions can range from a few to a plurality of different amino acid residues, including all twenty naturally occurring amino acids or functional equivalents and analogues thereof. In some cases, non-naturally occurring amino acids may also be considered and are known in the art.

Selection of the number and location of the amino acid positions to vary is flexible and can depend on the intended use and desired efficiency for identification of the altered variable region having a desirable activity such as substantially the same or greater binding affinity compared to the donor variable region. In this regard, the greater the number of changes that are incorporated into an altered variable region population, the more efficient it is to identify at least one species that exhibits a desirable activity, for example, substantially the same or greater binding affinity as the donor. Alternatively, where the user has empirical or actual data to the affect that certain amino acid residues or positions contribute disproportionally to binding affinity, then it can be desirable to produce a limited population of altered variable regions which focuses on changes within or around those identified residues or positions.

For example, if CDR grafted variable regions are desired, a large, diverse population of altered variable regions can include all the non-identical framework region positions between the donor and acceptor framework and all single CDR amino acid position changes. Alternatively, a population of intermediate diversity can include subsets, for example, of only the proximal non-identical framework positions to be incorporated together with all single CDR amino acid position changes to, for example, increase affinity of the humanized antibodies or antigen binding fragments. The diversity of the above populations can be further increased by, for example, additionally including all pair-wise CDR amino acid position changes. In contrast, populations focusing on predetermined residues or positions which incorporate variant residues at as few as one framework and/or one CDR amino acid position can similarly be constructed for screening and identification of an altered antibody variable region. As with the above populations, the diversity of such focused populations can be further increased by additionally expanding the positions selected for change to include other relevant positions in either or both of the framework and CDR regions. There are numerous other combinations ranging from few changes to many changes in either or both of the framework regions and CDRs that can additionally be employed, all of which will result in a population of altered variable regions that can be screened for the identification of at least one CDR grafted altered variable region having desired activity, for example, binding activity to PAI-1. Those skilled in the art will know, or can determine, which selected residue positions in the framework or donor CDRs, or subsets thereof, can be varied to produce a population for screening and identification of an altered antibody of the invention given the teachings and guidance provided herein. Codons encoding amino acids are known in the art.

Humanized antibodies and antigen-binding fragments can be made using conventional techniques known in the art. In addition, recombinantly prepared antibodies can often be produced in large quantities, particularly when utilizing high level expression vectors.

Antibodies can be sequenced using conventional techniques known in the art and the amino acid sequences of the complementarity determining regions (CDRs) determined. In one aspect, the amino acid sequences of one or more of the CDRs is inserted into a synthetic sequence of, for example, a human antibody (or antigen-binding fragment thereof) framework to create a human antibody that could limit adverse side reactions of treating a human patient with a non-human antibody. The amino acid sequences of one or more of the CDRs can also be inserted into a synthetic sequence of, for example, into a binding protein such as an Avimer™ to create a construct for administration to a human patient. Such techniques can be modified depending on the species of animal to be treated. For example, for veterinary uses, an antibody, antigen-binding fragment or binding protein can be synthesized for administration of a primate, a cow, a horse, etc.

In another aspect, using art-recognized techniques such as those provided and incorporated herein, nucleotides encoding amino acid sequences of one or more of the CDRs can inserted, for example, by recombinant techniques in restriction endonuclease sites of an existing polynucleotide that encodes an antibody, antigen-binding fragment or binding protein.

For high level production, the most widely used mammalian expression system is one which utilizes the gene amplification procedure offered by dehydrofolate reductase deficient ("dhfr-") Chinese hamster ovary cells. The system is well known to the skilled artisan. The system is based upon the dehydrofolate reductase "dhfr" gene, which encodes the DHFR enzyme, which catalyzes conversion of dehydrofolate to tetrahydrofolate. In order to achieve high production, dhfr-CHO cells are transfected with an expression vector containing a functional DHFR gene, together with a gene that encodes a desired protein. In this case, the desired protein is recombinant antibody heavy chain and/or light chain.

By increasing the amount of the competitive DHFR inhibitor methotrexate (MTX), the recombinant cells develop resistance by amplifying the dhfr gene. In standard cases, the amplification unit employed is much larger than the size of the dhfr gene, and as a result the antibody heavy chain is co-amplified.

When large scale production of the protein, such as the antibody chain, is desired, both the expression level and the stability of the cells being employed are taken into account. In long term culture, recombinant CHO cell populations lose homogeneity with respect to their specific antibody productivity during amplification, even though they derive from a single, parental clone.

The present application provides an isolated polynucleotide (nucleic acid) encoding an antibody or antigen-binding fragment as described herein, vectors containing such polynucleotides, and host cells and expression systems for transcribing and translating such polynucleotides into polypeptides.

The present application also provides constructs in the form of plasmids, vectors, transcription or expression cassettes which comprise at least one polynucleotide as above.

The present application also provides a recombinant host cell which comprises one or more constructs as above. A nucleic acid encoding any antibody or antigen-binding fragments thereof described herein as provided itself forms an aspect of the present application, as does a method of production of the antibody or antigen-binding fragments thereof described herein which method comprises expression from encoding nucleic acid therefrom. Expression can conveniently be achieved by culturing under appropriate conditions recombinant host cells containing the nucleic acid. Following production by expression, an antibody or antigen-binding fragment can be isolated and/or purified using any suitable technique, then used as appropriate.

Specific antibodies, antigen-binding fragments, and encoding nucleic acid molecules and vectors described herein can be provided isolated and/or purified, e.g., from their natural environment, in substantially pure or homogeneous form, or, in the case of nucleic acid, free or substantially free of nucleic acid or genes origin other than the sequence encoding a polypeptide with the required function. Nucleic acid can comprise DNA or RNA and can be wholly or partially synthetic.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common bacterial host is $E.\ coli$.

The expression of antibodies and antibody fragments in prokaryotic cells such as $E.\ coli$ is well established in the art. For a review, see for example Plückthun, A. Bio/Technology 9: 545-551 (1991). Expression in eukaryotic cells in culture is also available to those skilled in the art as an option for production of the antibodies and antigen-binding fragments described herein, see for recent reviews, for example Raff, M. E. (1993) Curr. Opinion Biotech. 4: 573-576; Trill J. J. et al. (1995) Curr. Opinion Biotech 6: 553-560, each of which is which is incorporated herein by reference in its entirety.

Suitable vectors can be chosen or constructed, containing appropriate regulatory sequences, including promoter sequences, terminator sequences, polyadenylation sequences, enhancer sequences, marker genes and other sequences as appropriate. Vectors can be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference in their entirety.

Thus, a further aspect provides a host cell containing nucleic acid as disclosed herein. A still further aspect provides a method comprising introducing such nucleic acid into a host cell. The introduction can employ any available technique. For eukaryotic cells, suitable techniques can include, for example, calcium phosphate transfection, DEAE Dextran, electroporation, liposome-mediated transfection and transduction using retrovirus or other virus, e.g., vaccinia or, for insect cells, baculovirus. For bacterial cells, suitable techniques can include, for example, calcium chloride transformation, electroporation and transfection using bacteriophage.

The introduction can be followed by causing or allowing expression from the nucleic acid, e.g. by culturing host cells under conditions for expression of the gene.

In one embodiment, the nucleic acid is integrated into the genome (e.g. chromosome) of the host cell. Integration can be promoted by inclusion of sequences which promote recombination with the genome, in accordance with standard techniques.

The present application also provides a method which comprises using a construct as stated above in an expression system in order to express the antibodies or antigen-binding fragments thereof as above.

The present application also relates to isolated nucleic acids, such as recombinant DNA molecules or cloned genes, or degenerate variants thereof, mutants, analogs, or fragments thereof, which encode an antibody or antigen-binding sequence that binds PAI-1 described herein.

In one aspect, the present application provides a nucleic acid which codes for an antibody or antigen-binding fragment thereof which binds PAI-1 as described herein.

In a further embodiment, the full DNA sequence of the recombinant DNA molecule or cloned gene of an antibody or antigen-binding fragment described herein can be operatively linked to an expression control sequence which can be introduced into an appropriate host. The application accordingly extends to unicellular hosts transformed with the cloned gene or recombinant DNA molecule comprising a DNA sequence encoding the $V_H$ and/or $V_L$, or portions thereof, of the antibody.

Another feature is the expression of the DNA sequences disclosed herein. As is well known in the art, DNA sequences can be expressed by operatively linking them to an expression control sequence in an appropriate expression vector and employing that expression vector to transform an appropriate unicellular host.

Such operative linking of a DNA sequence to an expression control sequence, of course, includes, if not already part of the DNA sequence, the provision of an initiation codon, ATG, in the correct reading frame upstream of the DNA sequence.

Polynucleotides and vectors can be provided in an isolated and/or a purified form (e.g., free or substantially free of polynucleotides of origin other than the polynucleotide encoding a polypeptide with the required function). As used herein, "substantially pure" and "substantially free," refer to a solution or suspension containing less than, for example, 20% or less extraneous material, 10% or less extraneous material, 5% or less extraneous material, 4% or less extraneous material, 3% or less extraneous material, 2% or less extraneous material, or 1% or less extraneous material.

A wide variety of host/expression vector combinations can be employed in expressing the DNA sequences of this invention. Useful expression vectors, for example, can consist of segments of chromosomal, non-chromosomal and synthetic DNA sequences. Suitable vectors include derivatives of SV40 and known bacterial plasmids, e.g., *E. coli* plasmids col E1, Pcr1, Pbr322, Pmb9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Also provided herein is a recombinant host cell which comprises one or more polynucleotide constructs. A polynucleotide encoding an antibody or antigen-binding fragment as provided herein forms an aspect of the present application, as does a method of production of the antibody or antigen-binding fragment which method comprises expression from the polynucleotide. Expression can be achieved, for example, by culturing under appropriate conditions recombinant host cells containing the polynucleotide. An antibody or antigen-binding fragment can then be isolated and/or purified using any suitable technique, and used as appropriate.

Any of a wide variety of expression control sequences—sequences that control the expression of a DNA sequence operatively linked to it—can be used in these vectors to express the DNA sequences. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary (CHO) cells, HeLa cells, baby hamster kidney cells, NSO mouse melanoma cells and many others. A common, bacterial host can be, for example, *E. coli*.

The expression of antibodies or antigen-binding fragments in prokaryotic cells, such as *E. coli*, is well established in the art. For a review, see for example Plückthun, A. Bio/Technology 9: 545-551 (1991). Expression in eukaryotic cells in culture is also available to those skilled in the art (Raff, M. E. (1993) Curr. Opinion Biotech. 4: 573-576; Trill J. J. et al. (1995) Curr. Opinion Biotech 6: 553-560).

A wide variety of unicellular host cells are also useful in expressing the DNA sequences. These hosts include well-known eukaryotic and prokaryotic hosts, such as strains of *E. coli, Pseudomonas, Bacillus, Streptomyces*, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences. Neither will all hosts function equally well with the same expression system. However, one skilled in the art will be able to select the proper vectors, expression control sequences, and hosts without undue experimentation to accomplish the desired expression without departing from the scope of this application. For example, in selecting a vector, the host must be considered because the vector must function in it. The vector's copy number, the ability to control that copy number, and the expression of any other proteins encoded by the vector, such as antibiotic markers, will also be considered. One of ordinary skill in the art can select the proper vectors, expression control sequences, and hosts to accomplish the desired expression without departing from the scope of this application. For example, in selecting a vector, the host is considered because the vector functions in it. The vector's copy number, the ability to control that copy number, and the expression of any other proteins encoded by the vector, such as antibiotic markers, can also be considered.

The present application also provides constructs in the form of plasmids, vectors, transcription or expression cassettes as described elsewhere herein which comprise at least one polynucleotide as above. Suitable vectors can be chosen or constructed, containing appropriate regulatory sequences, including promoter sequences, terminator sequences, polyadenylation sequences, enhancer sequences, selectable markers and other sequences as appropriate. Vectors can be plasmids, viral e.g., phage, phagemid, etc., as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

A further aspect provides a host cell containing one or more polynucleotides as disclosed herein. Yet a further aspect provides a method of introducing such one or more polynucleotides into a host cell, any available technique. For eukaryotic cells, suitable techniques can include, for example, calcium phosphate transfection, DEAEDextran, electroporation, liposome-mediated transfection and transduction using retrovirus or other virus (e.g. vaccinia) or, for insect cells, baculovirus. For bacterial cells, suitable techniques can include, for example calcium chloride transformation, electroporation and transfection using bacteriophages.

The introduction can be followed by causing or allowing expression from the one or more polynucleotides, e.g. by culturing host cells under conditions for expression of one or more polypeptides from one or more polynucleotides. Inducible systems can be used and expression induced by addition of an activator.

In one embodiment, the polynucleotides can be integrated into the genome (e.g., chromosome) of the host cell. Integration can be promoted by inclusion of sequences which promote recombination with the genome, in accordance with standard techniques. In another embodiment, the nucleic acid is maintained on an episomal vector in the host cell.

Methods are provided herein which include using a construct as stated above in an expression system in order to express a specific polypeptide.

Considering these and other factors, a person skilled in the art will be able to construct a variety of vector/expression control sequence/host combinations that will express the DNA sequences on fermentation or in large scale animal culture.

A polynucleotide encoding an antibody, antigen-binding fragment, or a binding protein can be prepared recombinantly/synthetically in addition to, or rather than, cloned. The polynucleotide can be designed with the appropriate codons for the antibody, antigen-binding fragment, or a binding protein. In general, one will select preferred codons for an intended host if the sequence will be used for expression. The complete polynucleotide can be assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

A general method for site-specific incorporation of unnatural amino acids into proteins is described in Christopher J. Noren, Spencer J. Anthony-Cahill, Michael C. Griffith, Peter G. Schultz, Science, 244:182-188 (April 1989). This method can be used to create analogs with unnatural amino acids.

As mentioned above, a DNA sequence encoding an antibody or antigen-binding fragment thereof can be prepared synthetically rather than cloned. The DNA sequence can be designed with the appropriate codons for the antibody or antigen-binding fragment amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984), each of which is which is incorporated herein by reference in its entirety.

C. Anti-PAI-1 Antibodies

Simultaneous incorporation of all of the FR and/or CDR encoding nucleic acids and all of the selected amino acid position changes can be accomplished by a variety of methods known to those skilled in the art, including for example, recombinant and chemical synthesis. For example, simultaneous incorporation can be accomplished by, for example, chemically synthesizing the nucleotide sequence for the acceptor variable region, fused together with the donor CDR encoding nucleic acids, and incorporating at the positions selected for harboring variable amino acid residues a plurality of corresponding amino acid codons.

Provided herein are antibodies and antigen-binding fragments thereof that bind to PAI-1. Antibodies and antigen-binding fragments thereof that bind PAI-1 and inhibit (partially or fully) or manage/treat (partially or fully) symptoms associated with PAI-1 (e.g., inhibition of thrombolysis). Inhibition or neutralization of PAI-1 by the antibodies described herein means increasing the conversion of the active form of PAI-1 to the latent form of PAI-1. Similarly, inhibition of PAI-1 binding to tPA or to uPA is also included within the meaning of inhibiting or neutralizing PAI-1. In yet another embodiment, an antibody or antigen-binding fragment inhibits binding of PAI-1 to tPA and/or uPA by increasing the conversion of the active form of PAI-1 to the latent form. In yet another embodiment, an antibody or antigen-binding fragment inhibits binding of PAI-1 to tPA and/or uPA by decreasing complex formation between PAI-1 and its target proteinases and by increasing cleavable PAI-1. The application also provides cell lines which can be used to produce the antibodies, methods for producing the cell lines, methods for expressing antibodies or antigen-binding fragments and purifying the same.

One can recognize that the antibodies and antigen-binding fragments thereof that specifically bind PAI-1 generated using the methods described herein can be tested using the assays provided herein or known in the art for the ability to bind to PAI-1 using conventional methods including, but not limited to, ELISA. Affinity of antibodies described herein can also be determined using conventional methods including, but not limited to, Biacore.

The antibodies and antigen binding fragments thereof described herein were constructed by humanization of the $V_H$ and $V_L$ sequences of the MA-33B8 antibody. To accomplish this humanization, a 3-dimensional model of the $V_H$ and $V_L$ chains of MA-33B8 was created and analyzed. The $V_H$ and $V_L$ sequences were then compared individually to a database of human germline sequences, from which human $V_H$ and $V_L$ sequences were chosen based on their homology to the $V_H$ and $V_L$ sequences of MA-33B8. The human $V_L$ sequence chosen for humanization was B3 (SEQ ID NO. 2). B3 has a sequence identity with MA-33B8 of 81% and the gene is highly expressed in the human germline repertoire. The human $V_H$ sequence chosen for humanization was VH1-2 (SEQ ID NO. 14). VH1-2 has sequence identity with MA-33B8 of 60% and is expressed with reasonable frequency in the human germline repertoire. The amino acid positions which were different between MA-33B8 and the human sequences were examined in the 3D model of MA-33B8 to determine which substitutions would be considered for modification. Amino acid selection criteria based on the 3D model analysis included, but was not limited to, for example, steric effects related to the amino acid, relative charge of the amino acid, and the location of the amino acid within the variable heavy and/or light chains. The identified and proposed substitutions for the human framework regions are incorporated into the B3 and VH1-2 human framework regions, and the CDRs of MA-33B8 are grafted into the corresponding B3 and VH1-2 human framework regions resulting in a multitude of humanized antibodies or antigen-binding fragments. Additionally, the FR-4 of the light chain is derived from human J germline sequence Jk2. Similarly, the FR-4 of the heavy chain is derived from human J germline sequence JH4.

Described herein are humanized antibodies and antigen-binding fragments that bind PAI-1 and increase the conversion of the active form of PAI-1 to the latent form. The antibodies and antigen-binding fragments described herein were generated as described above.

Antibodies and antigen-binding fragments thereof can have a variable heavy ($V_H$) chain, a variable light ($V_L$) chain, both, or binding portions thereof. In one embodiment, the $V_H$ chain has an amino acid sequence set forth as any of SEQ ID NOS: 15-17, or a binding portion thereof. Such $V_H$ chains can have framework regions sequences set forth as any of SEQ ID NOS: 18-40. In another embodiment, the $V_L$ chain has an amino acid sequence set forth as any of SEQ ID NOS: 3-4, or a binding portion thereof. Such $V_L$ chains can have framework regions sequences set forth as any of SEQ ID NOS: 5-12.

In one aspect, an antibody or antigen-binding fragment thereof that binds PAI-1 comprises a heavy chain variable region of SEQ ID NO: 16 and a light chain variable region of SEQ ID NO: 3. Such an antibody or antigen binding fragment thereof can comprise a heavy chain variable region of SEQ ID NO: 16 having one or more amino acid modifications including, but not limited to, substitution of valine (V) by isoleucine (I) or leucine (L) at position 2; a substitution of arginine (R) by lysine (K) at position 38; a substitution of glutamic acid (E) by lysine (K) or valine (V) at position 46; a substitution of valine (V) by phenylalanine (F) position 67; a substitution of methionine (M) by phenylalanine (F) or isoleucine (I) at position 69; a substitution of arginine (R) by leucine (L) at position 71; and a substitution of arginine (R) by lysine (K) at position 94 utilizing the Kabat numbering system.

In another aspect, an antibody or antigen-binding fragment thereof that binds PAI-1 comprises a heavy chain variable region of SEQ ID NO: 17 and a light chain variable region of SEQ ID NO: 3. Such an antibody or antigen binding fragment thereof can comprise a heavy chain variable region of SEQ ID NO: 17 further having one or more amino acid modifications including, but not limited to, a substitution of valine (V) by isoleucine (I) or leucine (L) at position 2; a substitution of arginine (R) by lysine (K) at position 38; a substitution of glutamic acid (E) by lysine (K) or valine (V) at position 46; and a substitution of methionine (M) by phenylalanine (F) or isoleucine (I) at position 69, utilizing the Kabat numbering system.

In yet another aspect, an antibody or antigen-binding fragment thereof that binds PAI-1 comprises a heavy chain variable region of SEQ ID NO: 18 and a light chain variable region of SEQ ID NO: 3. Such an antibody or antigen binding fragment thereof can comprise a heavy chain variable region of SEQ ID NO: 18 further having one or more amino acid modifications including, but not limited to, a substitution of valine (V) by isoleucine (I) or leucine (L) at position 2; and a substitution of arginine (R) by lysine (K) at position 38, utilizing the Kabat numbering system.

One can readily ascertain that antibodies or antigen-binding fragments thereof as described above or below can include one or more additional framework modifications. Additional modifications to one or more framework residues could be made, for example, to increase binding specificity, affinity or avidity, etc. In one non-limiting example, the light chain variable region contains a substitution of asparagine (N; SEQ ID NO: 3) by serine (S; SEQ ID NO: 6) or threonine (T; SEQ ID NO: 7) at position 22 of framework region 1 of the variable light chain utilizing the Kabat numbering system.

Provided herein are antibodies, or antigen-binding fragments thereof comprising one or more CDRs of the heavy and light chain variable regions of MA 33-B8 which bind PAI-1 and increase the conversion from the active form of PAI-1 to the latent form. Exemplary heavy and light chain CDRs include, for example, $V_H$ CDR1 (SEQ ID NO: 52), $V_H$ CDR2 (SEQ ID NO: 53), $V_H$ CDR3 (SEQ ID NO: 54), $V_L$ CDR1 (SEQ ID NO: 10), $V_L$ CDR1 (SEQ ID NO: 11), $V_L$ CDR2 (SEQ ID NO: 12), and $V_L$ CDR3 (SEQ ID NO: 13). In additional embodiments, one or more of these CDRS, in any combination, can further be utilized with any of the $V_H$ and $V_L$ framework embodiments described herein. In one non-limiting example, the humanized antibodies contain a $V_H$ CDR3 having an amino acid sequence set forth as SEQ ID NO: 54 and a $V_L$ CDR3 having an amino acid sequence set forth as SEQ ID NO: 13.

Provided herein are antibodies or antigen-binding fragments thereof which bind PAI-1 comprising a heavy chain variable region (SEQ ID NO. 16) and a light chain variable region (SEQ ID NO. 3) wherein said heavy chain variable region comprises one or more amino acid modifications including, but not limited to, a substitution of valine (V) by isoleucine (I) or isoleucine (I) at position 2, a substitution of arginine (R) by lysine (K) at position 38; a substitution of glutamic acid (E) by lysine (K) or valine (V) at position 46; a substitution of phenylalanine (F) by valine (V) at position 67; a substitution of methionine (M) by phenylalanine (F) or isoleucine (I) at position 69; a substitution of leucine (L) by arginine (R) at position 71; and a substitution of lysine (K) by arginine (R) at position 94 utilizing the Kabat numbering system, or any conservative substitution thereof. In a further embodiment, the light chain variable region can include a modification of a substitution of asparagine (N) by serine (S) or threonine (T) at position 22 utilizing the Kabat numbering system.

Further provided herein are antibodies, or antigen-binding fragments thereof, that bind PAI-1 comprising having a heavy chain variable region and a light chain variable region, wherein said heavy chain variable region comprises:
  (i) a CDR1 of SEQ ID NO: 52, a CDR2 of SEQ ID NO: 53, and a CDR3 of SEQ ID NO: 54;
  (ii) a heavy chain FR1 having the amino acid sequence of SEQ ID NO: 19 or the amino acid sequence of SEQ ID NO: 19 except for one or more substitutions such as valine (V) by isoleucine (I) or leucine (L) at position 2 utilizing the Kabat numbering system, or another conservative substitution thereof,
  (iii) a heavy chain FR2 having the amino acid sequence of SEQ ID NO: 21 or the amino acid sequence of SEQ ID NO: 21 except for one or more substitutions such as:
    (a) a substitution of arginine (R) by lysine (K) at position 38, and/or
    (b) a substitution of glutamic acid (E) by lysine (K) or valine (V) at position 46 utilizing the Kabat numbering system or another conservative substitution thereof;
  (iv) a heavy chain FR3 having the amino acid sequence of SEQ ID NO: 27 or the amino acid sequence of SEQ ID NO: 27 except for one or more substitutions such as:
    (a) a substitution of valine (V) by phenylalanine (F) at position 67;
    (b) a substitution of methionine (M) by phenylalanine (F) or isoleucine (I) at position 69;
    (c) a substitution of arginine (R) by leucine (L) at position 71; and/or
    (d) a substitution of arginine (R) by lysine (K) at position 94 utilizing the Kabat numbering system or another conservative substitution thereof, and
  (v) a heavy chain FR4 having the amino acid sequence of SEQ ID NO: 51 or the amino acid sequence of SEQ ID NO: 51 except for one or more conservative substitutions,
and wherein said light chain variable region comprises:
  (i) a CDR1 of SEQ ID NO: 10 or 11, a CDR2 of SEQ ID NO: 12, and a CDR3 of SEQ ID NO: 13;
  (ii) a light chain FR1 having the amino acid sequence of SEQ ID NO: 5 or the amino acid sequence of SEQ ID NO: 5 except for a substitution of asparagine (N) by serine (S) or threonine (T) at position 22 utilizing the Kabat numbering system or another conservative substitution thereof,
  (iii) a light chain FR2 having the amino acid sequence of SEQ ID NO: 7 or the amino acid sequence of SEQ ID NO: 7 except for one or more conservative substitutions;
  (iv) a light chain FR3 having the amino acid sequence of SEQ ID NO: 8 or the amino acid sequence of SEQ ID NO: 8 except for one or more conservative substitutions; and
  (v) a light chain FR4 having the amino acid sequence of SEQ ID NO: 9 or the amino acid sequence of SEQ ID NO: 9 except for one or more conservative substitutions.

Conservative substitutions are minor modification of these nucleotide sequences and/or amino acids are intended to be included as heavy and light chain encoding nucleic acids and their functional fragments. Such minor modifications include, for example, those which do not change the encoded amino acid sequence due to the degeneracy of the genetic code as well as those which result in only a conservative substitution of the encoded amino acid sequence or those that do not substantially alter the binding capacity of the antibody. Conservative substitutions of encoded amino acids include, for example, amino acids which belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are included within the nucleic acids encoding heavy and light chain polypeptides of the invention so long as the nucleic acid or encoded polypeptides retain some, or all, of their function as described herein and which have use in the methods described herein. Non-conservative substitutions are those that are not identified as conservative substitutions. Using the methods described herein, one can ascertain whether it would be possible to substitute a non-conservative amino acid for a framework amino acid residue and test the function of the modified antibody using the assays described elsewhere herein.

Further provided is an antibody or antigen-binding fragment thereof which contains a heavy chain FR1 having an amino acid sequence as set forth in SEQ ID NO: 19; a heavy chain FR2 having an amino acid sequence as set forth in SEQ ID NO: 21; a heavy chain FR3 having an amino acid sequence as set forth in SEQ ID NO: 35 (i.e., an amino acid sequence containing substitutions at positions 67, 71 and 94 utilizing the Kabat numbering system); a heavy chain FR4 having an amino acid sequence as set forth in SEQ ID NO: 51; a light chain FR1 having an amino acid sequence as set forth in SEQ ID NO: 5; a light chain FR2 having an amino acid sequence as set forth in SEQ ID NO: 7; a light chain FR3 having an amino acid sequence as set forth in SEQ ID NO: 8; a light chain FR4 having an amino acid sequence as set forth in SEQ ID NO: 9.

Further provided is an antibody or antigen-binding fragment thereof which contains a heavy chain FR1 having an amino acid sequence as set forth in SEQ ID NO: 19; a heavy chain FR2 having an amino acid sequence as set forth in SEQ ID NO: 23; a heavy chain FR3 having an amino acid sequence as set forth in SEQ ID NO: 33 (i.e., an amino acid sequence containing substitutions at positions 67, 69, 71 and 94 utilizing the Kabat numbering system); a heavy chain FR4 having an amino acid sequence as set forth in SEQ ID NO: 51; a light chain FR1 having an amino acid sequence as set forth in SEQ ID NO: 5; a light chain FR2 having an amino acid sequence as set forth in SEQ ID NO: 7; a light chain FR3 having an amino acid sequence as set forth in SEQ ID NO: 8; a light chain FR4 having an amino acid sequence as set forth in SEQ ID NO: 9.

Further provided is an antibody or antigen-binding fragment thereof described herein having one or more modification in one or more CDRs. In one non-limiting example, the antibody or antigen-binding fragment thereof includes a substitution of cysteine (C) by leucine (L) at position 32 of the $V_L$ utilizing the Kabat numbering system (i.e., position 15 of CDR1 as set forth in SEQ ID NO: 11).

Provided herein are V$_L$ regions of antibodies, or antigen binding fragments thereof, containing one or more FRs such as, for example, SEQ ID NO: 5, SEQ ID NO: 6, SEQ ID NO: 55, SEQ ID NO: 7, SEQ ID NO: 8, SEQ ID NO: 9, the antibodies or antigen binding fragments thereof having specific binding activity for PAI-1 and which are able to induce a conversion of the active form of PAI-1 to the latent form.

Provided herein are V$_H$ regions of antibodies, or antigen binding fragments thereof, containing one or more FRs such as, for example, SEQ ID NO: 19, SEQ ID NO: 20, SEQ ID NO: 57, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, and SEQ ID NO: 51, the antibodies or antigen binding fragments thereof having specific binding activity for PAI-1 and which are able to induce a conversion of the active form of PAI-1 to the latent form.

Further provided herein are antibodies or antigen-binding fragments thereof containing a variable heavy chain FR1 amino acid sequence set forth as SEQ ID NO: 19, 20 or 57; a variable heavy chain FR2 amino acid sequence set forth as SEQ ID NOS: 21, 22, 23, 24, 25 or 26; a variable heavy chain FR3 amino acid sequence set forth as SEQ ID NO: 27, 28, 29, 30, 31, 32, 33, 34, 35, 36, 37, 38, 39, 40, 41, 42, 43, 44, 45, 46, 47, 48, 49 or 50; and a variable heavy chain FR4 of SEQ ID NO: 51. Such antibodies or antigen binding fragments thereof exhibit specific binding activity for PAI-1 and are able to induce a conversion of the active form of PAI-1 to the latent form.

Also provided herein are antibodies or antigen-binding fragments thereof containing a variable light chain FR1 amino acid sequence set forth as SEQ ID NO: 5, 6 or 55; a variable light chain FR2 amino acid sequence set forth as SEQ ID NO: 7; a variable light chain FR3 amino acid sequence set forth as SEQ ID NO: 8, and a variable light chain FR4 amino acid sequence set forth as SEQ ID NO: 9. Such antibodies or antigen binding fragments thereof having specific binding activity for PAI-1 and which are able to induce a conversion of the active form of PAI-1 to the latent form.

CDR3 regions having amino acid sequences substantially as set out as the CDR3 regions of the antibodies described herein will be carried in a structure which allows for binding of the CDR3 regions to PAI-1. The structure for carrying the CDR3s can be of an antibody heavy or light chain sequence or substantial portion thereof in which the CDR3 regions are located at locations corresponding to the CDR3 region of naturally-occurring V$_H$ and V$_L$ antibody variable domains encoded by rearranged immunoglobulin genes.

In one non-limiting example, provided herein are antibodies or antigen binding fragments thereof containing a variable heavy chain having a CDR3 which has an amino acid sequence set forth as SEQ ID NO: 54 and a variable light chain having a CDR3 which has an amino acid sequence set forth as 13 (light chain CDR3) and one or more FR amino acid sequences set forth as, for example, SEQ ID NO: 5, SEQ ID NO: 6, SEQ ID NO: 55, SEQ ID NO: 7, SEQ ID NO: 8, SEQ ID NO: 9, SEQ ID NO: 19, SEQ ID NO: 20, SEQ ID NO: 57, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, and SEQ ID NO: 51 (or such FRs containing one or more additional modifications), where the antibodies or antigen binding fragments have 3 CDRs and 4 FRs in each of the VH and VL regions, have specific binding activity for PAI-1 and which are able to induce a conversion of the active form of PAI-1 to the latent form.

In one aspect, a humanized 33B8 variable heavy chain is fused to a construct of an antibody such as, but not limited to, an IgG1 or an IgG4. In one embodiment, a variable light chain having an amino acid sequence set forth as SEQ ID NO: 101 is used in conjunction with a humanized variable heavy chain fused to a human IgG1 Fc construct having an amino acid sequence set forth as SEQ ID NO: 99. Alternatively, in another embodiment, a variable light chain having an amino acid sequence set forth as SEQ ID NO: 101 is used in conjunction with a humanized variable heavy chain fused to a human IgG4 Fc construct having an amino acid sequence set forth as SEQ ID NO: 100.

Provided herein is an antibody, or antigen-binding fragment thereof, comprising a light chain variable region having an amino acid sequence set forth as SEQ ID NO: 62 and a heavy chain variable region having an amino acid sequence set forth as SEQ ID NO: 64.

Provided herein is an antibody, or antigen-binding fragment thereof, comprising a light chain variable region having an amino acid sequence set forth as SEQ ID NO: 62 and a heavy chain variable region having an amino acid sequence set forth as SEQ ID NO: 64, wherein: the heavy chain variable region further comprises one or more modifications selected from the group consisting of a substitution of tyrosine (Y) by phenylalanine (F) at position 27; a substitution of threonine (T) by asparagine (N) at position 28; a substitution of phenylalanine (F) by isoleucine (I) at position 29; a substitution of threonine (T) by lysine (K) position 30; a substitution of glutamine (Q) by lysine (K) at position 38; a substitution of methionine (M) by isoleucine (I) at position 48; a substitution of arginine (R) by lysine (K) at position 66; a substitution of valine (V) by alanine (A) at position 67; a substitution of alanine (A) by threonine (T) at position 93; and a substitution of threonine (T) by arginine (R) at position 94 utilizing the Kabat numbering system; and the light chain variable region further comprises one or more modifications selected from the group consisting of a substitution of alanine (A) by threonine (T) at position 43; a substitution of proline (P) by valine (V) at position 44; a substitution of phenylalanine (F) by tyrosine (Y) at position 71; and a substitution of tyrosine (Y) by phenylalanine (F) at position 87 utilizing the Kabat numbering system.

Provided herein is an antibody, or antigen-binding fragment thereof, that binds PAI-1 comprising a heavy chain variable region having an amino acid sequence set forth as SEQ ID NO: 64, 65, 66 or 67]; and a light chain variable region having an amino acid sequence set forth as SEQ ID NO: 62 or 63. An antibody, or antigen-binding fragment thereof, can comprise a heavy chain variable region having an amino acid sequence set forth as SEQ ID NO: 64 and a light chain variable region having an amino acid sequence set forth as SEQ ID NO: 62. An antibody, or antigen-binding fragment thereof, can comprise a heavy chain variable region having an amino acid sequence set forth as SEQ ID NO: 64 and a light chain variable region having an amino acid sequence set forth as SEQ ID NO: 63. An antibody, or antigen-binding fragment thereof, can comprise a heavy chain variable region having an amino acid sequence set forth as SEQ ID NO: 65 and a light chain variable region having an amino acid sequence set forth as SEQ ID NO: 62. An antibody, or antigen-binding fragment thereof, can comprise a heavy chain variable region having an amino acid sequence set forth as SEQ ID NO: 65 and a light chain variable region having an amino acid sequence set forth as SEQ ID NO: 63. An antibody, or antigen-binding fragment thereof, can comprise a heavy chain variable region having an amino acid sequence set forth as SEQ ID NO: 66 and a light chain variable region having an amino acid sequence set forth as SEQ ID NO: 62. An antibody, or antigen-binding fragment thereof, can comprise a heavy chain variable region having an amino acid sequence set forth as SEQ ID NO: 66 and a light chain variable region having an amino acid sequence set forth as SEQ ID NO: 63. An antibody, or antigen-binding fragment thereof, can comprise a heavy chain variable region having an amino acid sequence set forth as SEQ ID NO: 67 and a light chain variable region having an amino acid sequence set forth as SEQ ID NO: 62. An antibody, or antigen-binding fragment thereof, can comprise a heavy chain variable region having an amino acid sequence set forth as SEQ ID NO: 67; and a light chain variable region having an amino acid sequence set forth as SEQ ID NO: 63. Such antibodies can bind to PAI-1 and neutralize its activity. In any of such embodiments, a heavy chain variable region can further comprise a substitution of glutamine (Q) by lysine (K); and the light chain variable region further comprise one or more modifications selected from the group consisting of: a substitution of alanine (A) by threonine (T) at position 43, a substitution of proline (P) by valine (V) at position 44, and a substitution of tyrosine (Y) by phenylalanine (F) at position 87 utilizing the Kabat numbering system Provided herein is an antibody, or antigen-binding fragment thereof, that binds PAI-1, comprising a heavy chain variable region and a light chain variable region, wherein said heavy chain variable region comprises:
  (i) a CDR1 of SEQ ID NO: 93, a CDR2 of SEQ ID NO: 94, and a CDR3 of SEQ ID NO: 95;
  (ii) a heavy chain FR1 having the amino acid sequence of SEQ ID NO: 78 or the amino acid sequence of SEQ ID NO: 78 except for one or more substitutions selected from the group consisting of:
    (a) a substitution of tyrosine (Y) by phenylalanine (F) at position 27;
    (b) a substitution of threonine (T) by asparagine (N) at position 28;
    (c) a substitution of phenylalanine (F) by isoleucine (I) at position 29; and
    (d) a substitution of threonine (T) by lysine (K) at position 30 utilizing the Kabat numbering system;
  (iii) a heavy chain FR2 having the amino acid sequence of SEQ ID NO: 84 or the amino acid sequence of SEQ ID NO: 84 except for one or more substitutions selected from the group consisting of:
    (a) a substitution of glutamine (Q) by lysine (K) at position 38, and
    (b) a substitution of methionine (M) by isoleucine (I) at position 48 utilizing the Kabat numbering system;
  (iv) a heavy chain FR3 having the amino acid sequence of SEQ ID NO: 88 or the amino acid sequence of SEQ ID NO: 88 except for one or more substitutions selected from the group consisting of:
    (a) a substitution of arginine (R) by lysine (K) at position 66;
    (b) a substitution of valine (V) by alanine (A) at position 67;
    (c) a substitution of alanine (A) by threonine (T) at position 93; and
    (d) a substitution of threonine (T) by arginine (R) at position 94 utilizing the Kabat numbering system; and
  (v) a heavy chain FR4 having the amino acid sequence of SEQ ID NO: 92 or the amino acid sequence of SEQ ID NO: 92 except for one or more conservative substitutions;
and said light chain variable region comprises:
  (i) a CDR1 of SEQ ID NO: 96, a CDR2 of SEQ ID NO: 97, and a CDR3 of SEQ ID NO: 98;
  (ii) a light chain FR1 having the amino acid sequence of SEQ ID NO: 68 or the amino acid sequence of SEQ ID NO: 68 except for one or more conservative substitutions;
  (iii) a light chain FR2 having the amino acid sequence of SEQ ID NO: 69 or the amino acid sequence of SEQ ID NO: 69 except for one or more substitutions selected from the group consisting of:
    (a) a substitution of alanine (A) by threonine (T) at position 43; and
    (b) a substitution of proline (P) by valine (V) at position 44 utilizing the Kabat numbering system;
  (iv) a light chain FR3 having the amino acid sequence of SEQ ID NO: 73 or the amino acid sequence of SEQ ID NO: 73 except for one or more substitutions selected from the group consisting of:
    (a) a substitution of phenylalanine (F) by tyrosine (Y) at position 71; and
    (b) a substitution of tyrosine (Y) by phenylalanine (F) utilizing the Kabat numbering system; and
  (v) a light chain FR4 having the amino acid sequence of SEQ ID NO: 77 or the amino acid sequence of SEQ ID NO: 77 except for one or more conservative substitutions.

An antibody, or antigen-binding fragment thereof, provided herein can comprise a heavy chain variable region CDR1 having an amino acid sequence as set forth in SEQ ID NO: 93, a heavy chain variable region CDR2 having an amino acid sequence as set forth in SEQ ID NO: 94, a heavy chain variable region CDR3 having an amino acid sequence as set forth in SEQ ID NO: 95, a light chain variable region CDR1 having an amino acid sequence as set forth in SEQ ID NO: 96, a light chain variable region CDR2 having an amino acid sequence as set forth in SEQ ID NO: 97, and a light chain variable region CDR3 having an amino acid sequence as set forth in SEQ ID NO:98.

In one embodiment, the antibody, or antigen-binding fragment thereof, comprises a heavy chain variable region FR1 having an amino acid sequence as set forth in SEQ ID NO: 78; a heavy chain variable region FR2 having an amino acid sequence as set forth in SEQ ID NO: 84; a heavy chain variable region FR3 having an amino acid sequence as set forth in SEQ ID NO: 88; a heavy chain variable region FR4 having an amino acid sequence as set forth in SEQ ID NO: 92.

In another embodiment, the antibody, or antigen-binding fragment thereof, comprises a heavy chain variable region FR1 having an amino acid sequence as set forth in SEQ ID NO: 79; a heavy chain variable region FR2 having an amino acid sequence as set forth in SEQ ID NO: 84; a heavy chain variable region FR3 having an amino acid sequence as set forth in SEQ ID NO: 91; a heavy chain variable region FR4 having an amino acid sequence as set forth in SEQ ID NO: 92.

In another embodiment, the antibody, or antigen-binding fragment thereof, comprises a heavy chain variable region FR1 having an amino acid sequence as set forth in SEQ ID NO: 79; a heavy chain variable region FR2 having an amino acid sequence as set forth in SEQ ID NO: 84; a heavy chain variable region FR3 having an amino acid sequence as set forth in SEQ ID NO: 90; a heavy chain variable region FR4 having an amino acid sequence as set forth in SEQ ID NO: 92.

In another embodiment, the antibody, or antigen-binding fragment thereof, comprises a heavy chain variable region FR1 having an amino acid sequence as set forth in SEQ ID NO: 79; a heavy chain variable region FR2 having an amino acid sequence as set forth in SEQ ID NO: 85; a heavy chain variable region FR3 having an amino acid sequence as set forth in SEQ ID NO: 91; a heavy chain variable region FR4 having an amino acid sequence as set forth in SEQ ID NO: 92.

In another embodiment, the antibody, or antigen-binding fragment thereof, comprises a light chain variable region FR1 having an amino acid sequence as set forth in SEQ ID NO: 68; a light chain variable region FR2 having an amino acid sequence as set forth in SEQ ID NO: 69; a light chain variable region FR3 having an amino acid sequence as set forth in SEQ ID NO: 73; and a light chain variable region FR4 having an amino acid sequence as set forth in SEQ ID NO: 77.

In another embodiment, the antibody, or antigen-binding fragment thereof, comprises a light chain variable region FR1 having an amino acid sequence as set forth in SEQ ID NO: 68; a light chain variable region FR2 having an amino acid sequence as set forth in SEQ ID NO: 69; a light chain variable region FR3 having an amino acid sequence as set forth in SEQ ID NO: 74; and a light chain variable region FR4 having an amino acid sequence as set forth in SEQ ID NO: 77.

A substantial portion of a variable domain will include three CDR regions, together with their intervening framework regions. The portion can also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of humanized PAI-1 antibodies and antigen-binding fragments described herein made by recombinant DNA techniques can result in the introduction of N- or C-terminal residues encoded by linkers introduced to facilitate cloning or other manipulation steps. Other manipulation steps include the introduction of linkers to join variable domains to further protein sequences including immunoglobulin heavy chains, other variable domains (for example in the production of diabodies) or protein labels as discussed in more detail below.

Humanized 55F4 CDR3 regions having amino acid sequences substantially as set out as the CDR3 regions of the antibodies described herein will be carried in a structure which allows for binding of the CDR3 regions to PAI-1. The structure for carrying the CDR3s can be of an antibody heavy or light chain sequence or substantial portion thereof in which the CDR3 regions are located at locations corresponding to the CDR3 region of naturally-occurring $V_H$ and $V_L$ antibody variable domains encoded by rearranged immunoglobulin genes.

In one non-limiting example, provided herein are antibodies or antigen binding fragments thereof containing a variable heavy chain having a CDR3 which has an amino acid sequence set forth as SEQ ID NO: 95 and a variable light chain having a CDR3 which has an amino acid sequence set forth as 98 (light chain CDR3) and one or more FR amino acid sequences set forth as, for example, described above (or such FRs containing one or more additional modifications), where the antibodies or antigen binding fragments have 3 CDRs and 4 FRs in each of the VH and VL regions, have specific binding activity for PAI-1 and which are able to decrease complex formation between PAI-1 and its target proteinases and by increase cleavable PAI-1.

In another aspect, the present application provides a humanized antibody capable of competing with a humanized anti-PAI-1 antibody or antigen-binding described herein under conditions in which at least 10% of an antibody having the $V_H$ and $V_L$ sequences of the antibody is blocked from binding to PAI-1 by competition with such an antibody in an ELISA assay.

Provided herein are neutralizing antibodies or antigen-binding fragments that bind to PAI-1 and neutralize the activity of PAI-1. The neutralizing antibody can for example, increase the rate of conversion of PAI-1 from the active form to the latent form. Alternatively, the neutralizing antibody can for example, decreasing complex formation between PAI-1 and its target proteinases and by increasing cleavable PAI-1.

Binding of an antibody or antigen-binding fragment to PAI-1 can partially (e.g., 5%, 10%, 20%, 30%, 40%, 50%, 60%, 70%, 80%, 90%, 95%, 98%, 99% or any number therein) or completely inhibit the activity of PAI-1 by converting PAI-1 to its latent form, thereby inhibiting interactions of PAI-1 with tPA and/or uPA. Alternatively, binding of an antibody or antigen-binding fragment to PAI-1 can partially (e.g., 5%, 10%, 20%, 30%, 40%, 50%, 60%, 70%, 80%, 90%, 95%, 98%, 99% or any number therein) or completely inhibit the activity of PAI-1 by decreasing complex formation between PAI-1 and its target proteinases and by increasing cleavable PAI-1. The neutralizing or inhibiting activity of an antibody or antigen-binding fragment can be determined using an in vitro assay and/or in vivo using art-recognized assays such as those described herein or otherwise known in the art.

Percentage (%) of inhibition of binding of PAI-1 to tPA and/or uPA (or vice versa) by an antibody or antigen, binding fragment which specifically binds to PAI-1, for example, at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, or greater than negative controls is indicative of an antibody, or antigen, binding fragment thereof, that inhibits the binding of PAI-1 to tPA and/or uPA. Percentage (%) of inhibition of binding of PAI-1 to tPA and/or uPA by such an antibody or antigen, binding fragment of less than 2-fold greater than negative controls is indicative of an antibody or antigen, binding fragment that does not inhibit binding of PAI-1 to tPA and/or uPA.

In one aspect, the antigen-binding fragment of any one of the humanized antibodies described above is a Fab, a Fab', a Fd, a F(ab')$_2$, a Fv, a scFv, a single chain binding polypeptide (e.g., a scFv with Fc portion) or any other functional fragment thereof as described herein.

Antibodies or antigen-binding fragments described herein are useful in detection or diagnostic applications as described in more detail below. Antibodies or antigen-binding fragments described herein are useful for converting PAI-1 to its latent form, decreasing complex formation between PAI-1 and its target proteinases and/or increasing cleavable PAI-1, which, in turn, can decrease persistence of venous and arterial thrombi, decrease atherosclerotic plaque formation, decrease or preventing renal extracellular matrix accumulation, decrease formation or persistence of glomerular sclerosis or a combination thereof.

Antibodies, or antigen-binding fragments thereof, described herein can be further modified to alter the specific properties of the antibody while retaining the desired functionality, if needed. For example, in one embodiment, the compound can be modified to alter a pharmacokinetic property of the compound, such as in vivo stability, solubility, bioavailability or half-life. Antibodies, or antigen-binding fragments thereof, described herein can further comprise a therapeutic moiety, a detectable moiety, or both, for use in diagnostic and/or therapeutic applications as described in more detail below.

Antibodies, or antigen-binding fragments thereof, can be modified using techniques known in the art for various purposes such as, for example, by addition of polyethylene glycol (PEG). PEG modification (PEGylation) can lead to one or more of improved circulation time, improved solubility, improved resistance to proteolysis, reduced antigenicity and immunogenicity, improved bioavailability, reduced toxicity, improved stability, and easier formulation (for a review see, Francis et al., International Journal of Hematology 68:1-18, 1998).

In the case of an antigen-binding fragment which does not contain an Fc portion, an Fc portion can be added to (e.g., recombinantly) the fragment, for example, to increase half-life of the antigen-binding fragment in circulation in blood when administered to a patient. Choice of an appropriate Fc region and methods of to incorporate such fragments are known in the art. Incorporating a Fc region of an IgG into a polypeptide of interest so as to increase its circulatory half-life, but so as not to lose its biological activity can be accomplished using conventional techniques known in the art such as, for example, described in U.S. Pat. No. 6,096,871, which is hereby incorporated by reference in its entirety. Fc portions of antibodies can be further modified to increase half-life of the antigen-binding fragment in circulation in blood when administered to a patient. Modifications can be determined using conventional means in the art such as, for example, described in U.S. Pat. No. 7,217,798, which is hereby incorporated by reference in its entirety. Other methods of improving the half-life of antibody-based fusion proteins in circulation are also known such as, for example, described in U.S. Pat. Nos. 7,091,321 and 6,737,056, each of which is hereby incorporated by reference. Thus, antibodies and antigen-binding fragments as described herein can further comprise antibody constant regions or parts thereof. For example, antibodies or antigen-binding fragments thereof that can inhibit or neutralize PAI-1 can be attached at their C-terminal end to antibody light chain constant domains including human Cκ or Cλ chains. Similarly, antibodies or antigen-binding fragments thereof that can inhibit or neutralize PAI-1 can be attached at their C-terminal end to all or part of an immunoglobulin heavy chain derived from any antibody isotype, e.g., IgG, IgA, IgE, IgD and IgM and any of the isotype subclasses, particularly IgG1, IgG2b, IgG2a, IgG3 and IgG4.

Additionally, the antibodies or antigen-binding fragments described herein can also be modified so that they are able to cross the blood-brain barrier. Such modification of the antibodies or antigen-binding fragments described herein allows for the treatment of neurological diseases such as Alzheimer's disease. Exemplary modifications to allow proteins such as antibodies or antigen-binding fragments to cross the blood-brain barrier are described in US Patent Application Publication 2007/0082380 which is hereby incorporated by reference in its entirety.

Glycosylation of immunoglobulins has been shown to have significant effects on their effector functions, structural stability, and rate of secretion from antibody-producing cells (Leatherbarrow et al., Mol. Immunol. 22:407 (1985)). The carbohydrate groups responsible for these properties are generally attached to the constant (C) regions of the antibodies. For example, glycosylation of IgG at asparagine 297 in the $C_H2$ domain is required for full capacity of IgG to activate the classical pathway of complement-dependent cytolysis (Tao and Morrison, J. Immunol. 143:2595 (1989)). Glycosylation of IgM at asparagine 402 in the $C_H3$ domain is necessary for proper assembly and cytolytic activity of the antibody (Muraoka and Shulman, J. Immunol. 142:695 (1989)). Removal of glycosylation sites as positions 162 and 419 in the $C_H1$ and $C_H3$ domains of an IgA antibody led to intracellular degradation and at least 90% inhibition of secretion (Taylor and Wall, Mol. Cell. Biol. 8:4197 (1988)).

Glycosylation of immunoglobulins in the variable (V) region has also been observed. Sox and Hood reported that about 20% of human antibodies are glycosylated in the V region (Proc. Natl. Acad. Sci. USA 66:975 (1970)). Glycosylation of the V domain is believed to arise from fortuitous occurrences of the N-linked glycosylation signal Asn-Xaa-Ser/Thr in the V region sequence and has not been recognized in the art as playing an important role in immunoglobulin function.

Glycosylation at a variable domain framework residue can alter the binding interaction of the antibody with antigen. The present invention includes criteria by which a limited number of amino acids in the framework or CDRs of a humanized immunoglobulin chain are chosen to be mutated (e.g., by substitution, deletion, or addition of residues) in order to increase the affinity of an antibody.

Affinity for binding a pre-determined polypeptide antigen can, generally, be modulated by introducing one or more mutations into the V region framework, typically in areas adjacent to one or more CDRs and/or in one or more framework regions. Typically, such mutations involve the introduction of conservative amino acid substitutions that either destroy or create the glycosylation site sequences but do not substantially affect the hydropathic structural properties of the polypeptide. Typically, mutations that introduce a proline residue are avoided. Glycosylation of antibodies and antigen-binding fragments thereof is further described in U.S. Pat. No. 6,350,861, which is incorporated by reference herein with respect to glycosylation.

Antibodies, or antigen-binding fragments thereof, can be formulated for short-term delivery or extended (long term) delivery.

Antibodies, or antigen-binding fragments thereof, can decrease persistence of venous and arterial thrombi or atherosclerotic plaque formation. Thus, the antibodies, or antigen-binding fragments thereof, have utility in the therapeutic applications described in more detail below.

Antibodies, or antigen-binding fragments thereof, that bind to PAI-1 can also be used for purification of PAI-1 and/or to detect excess PAI-1 levels in a sample or patient to detect or diagnose a disease or disorder associated with excess levels of PAI-1 as described in more detail below.

Humanized antibodies, antigen-binding fragments, and binding proteins which inhibit or neutralize PAI-1 generated using such methods can be tested for one or more of their binding affinity, avidity, and neutralizing capabilities. Useful humanized antibodies, antigen-binding fragments, and binding proteins can be used to administer a patient to prevent, inhibit, manage or treat a condition disease or disorder associated with PAI-1.

Provided herein are methods of identifying humanized antibodies or antigen-binding fragments thereof that bind to PAI-1. Antibodies and antigen-binding fragments can be evaluated for one or more of binding affinity, association rates, disassociation rates and avidity. In one aspect, antibodies can be evaluated for their ability to neutralize the activity of PAI-1 or a polypeptide in which the PAI-1 binding sequence is present. Measurement binding affinity, association rates, disassociation rates and avidity can be accomplished using art-recognized assays including, but not limited to, an enzyme-linked-immunosorbent assay (ELISA), Scatchard Analysis, BIACORE analysis, etc., as well as other assays commonly used and known to those of ordinary skill in the art.

Measurement of binding of antibodies to PAI-1 and/or the ability of the antibodies and antigen-binding fragments thereof, for example, neutralize the activity of PAI-1, prevent binding of PAI-1 to a receptor or ligand, etc., can be determined using, for example, an enzyme-linked-immunosorbent assay (ELISA), a competitive binding assay, an ELISOPT assay, or any other useful assay known in the art. These assays are commonly used and well-known to those of ordinary skill in the art.

In one non-limiting embodiment, an ELISA assay can be used to measure the neutralizing capability of specific antibodies or antigen-binding fragments that bind to PAI-1, to prevent binding of PAI-1 to tPA and/or uPA.

Assays, such as an ELISA, also can be used to identify antibodies or antigen-binding fragments thereof which exhibit increased specificity for PAI-1 in comparison to other antibodies or antigen-binding fragments thereof. Assays, such as an ELISA, also can be used to identify antibodies or antigen-binding fragments thereof with bind to epitopes across one or more polypeptides and across one or more species of PAI-1. The specificity assay can be conducted by running parallel ELISAs in which a test antibodies or antigen-binding fragments thereof is screened concurrently in separate assay chambers for the ability to bind one or more epitopes on different species of the polypeptide containing the PAI-1 epitopes to identify antibodies or antigen-binding fragments thereof that bind to PAI-1. Another technique for measuring apparent binding affinity familiar to those of skill in the art is a surface plasmon resonance technique (analyzed on a BIACORE 2000 system) (Liljeblad, et al., Glyco. J. 2000, 17:323-329). Standard measurements and traditional binding assays are described by Heeley, R. P., Endocr. Res. 2002, 28:217-229.

Humanized antibodies to PAI-1 can also be assayed for their ability to treat various diseases and conditions, e.g., cardiovascular diseases and diabetes-related complications. Any suitable assay known to one of skill in the art can be used to monitor such effects. Several such techniques are described herein. In one example, the antibodies and antigen-binding fragments described herein are assayed for their ability to neutralize PAI-1. In another example, affinity constants for the antibodies and antigen-binding fragments described herein are determined by surface plasmon resonance (SPR). In yet another example, the antibodies and antigen-binding fragments described herein are assayed for their effect on the rate of PAI-1 inactivation.

II. Compositions

Each of the compounds described herein can be used as a composition when combined with an acceptable carrier or excipient. Such compositions are useful for in vitro or in vivo analysis or for administration to a subject in vivo or ex vivo for treating a subject with the disclosed compounds.

Thus pharmaceutical compositions can include, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

Pharmaceutical formulations comprising a protein of interest, e.g., an antibody or antigen-binding fragment, identified by the methods described herein can be prepared for storage by mixing the protein having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Acceptable carriers are physiologically acceptable to the administered patient and retain the therapeutic properties of the compounds with/in which it is administered. Acceptable carriers and their formulations are and generally described in, for example, Remington' pharmaceutical Sciences (18th Edition, ed. A. Gennaro, Mack Publishing Co., Easton, Pa. 1990). One exemplary carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Each carrier is acceptable in the sense of being compatible with the other ingredients of the formulation and not injurious to a subject to whom it is administered. Nor should an acceptable carrier alter the specific activity of the subject compounds.

In one aspect, provided herein are pharmaceutically acceptable or physiologically acceptable compositions including solvents (aqueous or non-aqueous), solutions, emulsions, dispersion media, coatings, isotonic and absorption promoting or delaying agents, compatible with pharmaceutical administration. Pharmaceutical compositions or pharmaceutical formulations therefore refer to a composition suitable for pharmaceutical use in a subject. The pharmaceutical compositions and formulations include an amount of a compound described herein and a pharmaceutically or physiologically acceptable carrier.

Compositions can be formulated to be compatible with a particular route of administration (i.e., systemic or local). Thus, compositions include carriers, diluents, or excipients suitable for administration by various routes.

In another embodiment, the compositions can further comprise, if needed, an acceptable additive in order to improve the stability of the compounds in composition and/or to control the release rate of the composition. Acceptable additives do not alter the specific activity of the subject compounds. Exemplary acceptable additives include, but are not limited to, a sugar such as mannitol, sorbitol, glucose, xylitol, trehalose, sorbose, sucrose, galactose, dextran, dextrose, fructose, lactose and mixtures thereof. Acceptable additives can be combined with acceptable carriers and/or excipients such as dextrose. Alternatively, exemplary acceptable additives include, but are not limited to, a surfactant such as polysorbate 20 or polysorbate 80 to increase stability of the peptide and decrease gelling of the solution. The surfactant can be added to the composition in an amount of 0.01% to 5% of the solution. Addition of such acceptable additives increases the stability and half-life of the composition in storage.

The pharmaceutical composition can be administered, for example, by injection. Compositions for injection include aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as mannitol, sorbitol, and sodium chloride may be included in the composition. The resulting solutions can be packaged for use as is, or lyophilized; the lyophilized preparation can later be combined with a sterile solution prior to administration. For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as needed. Sterile injectable solutions can be prepared by incorporating an active ingredient in the required amount in an appropriate solvent with one or a combination of ingredients enumerated above, as required, followed by filtered sterilization. Generally, dispersions are prepared by incorporating the active ingredient into a sterile vehicle which contains a basic dispersion medium and the required other ingredients from those enumerated above. In the case of sterile powders for the preparation of sterile injectable solutions, the preferred methods of preparation are vacuum drying and freeze drying which yields a powder of the active ingredient plus any additional desired ingredient from a previously sterile-filtered solution thereof.

Compositions can be conventionally administered intravenously, such as by injection of a unit dose, for example. For injection, an active ingredient can be in the form of a parenterally acceptable aqueous solution which is substantially pyrogen-free and has suitable pH, isotonicity and stability. One can prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Additionally, compositions can be administered via aerosolization. (Lahn et al., *Aerosolized Anti-T-cell-Receptor Antibodies Are Effective against Airway Inflammation and Hyperreactivity*, Int. Arch. Allegery Immuno., 134: 49-55 (2004)).

In one embodiment, the composition is lyophilized, for example, to increase shelf-life in storage. When the compositions are considered for use in medicaments or any of the methods provided herein, it is contemplated that the composition can be substantially free of pyrogens such that the composition will not cause an inflammatory reaction or an unsafe allergic reaction when administered to a human patient. Testing compositions for pyrogens and preparing compositions substantially free of pyrogens are well understood to one or ordinary skill of the art and can be accomplished using commercially available kits.

Acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) Pharm Res. 13:1760 1764; Samanen (1996) J. Pharm. Pharmacol. 48:119 135; and U.S. Pat. No. 5,391,377, describing lipid compositions for oral delivery of therapeutic agents).

The phrase "pharmaceutically acceptable" refers to molecular entities and compositions that are physiologically tolerable and do not typically produce an allergic or similar untoward reaction, such as gastric upset, dizziness and the like, when administered to a human.

The term "unit dose" when used in reference to a therapeutic composition refers to physically discrete units suitable as unitary dosage for humans, each unit containing a predetermined quantity of active material calculated to produce the desired therapeutic effect in association with the required diluent; i.e., carrier, or vehicle.

The compositions can be administered in a manner compatible with the dosage formulation, and in a therapeutically effective amount. The quantity to be administered depends on the subject to be treated, capacity of the subject's immune system to utilize the active ingredient, and degree of binding capacity desired. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood are contemplated.

One embodiment contemplates the use of the compositions described herein to make a medicament for treating a condition, disease or disorder described herein. Medicaments can be formulated based on the physical characteristics of the patient/subject needing treatment, and can be formulated in single or multiple formulations based on the stage of the condition, disease or disorder. Medicaments can be packaged in a suitable package with appropriate labels for the distribution to hospitals and clinics wherein the label is for the indication of treating a subject having a disease described herein. Medicaments can be packaged as a single or multiple units. Instructions for the dosage and administration of the compositions can be included with the packages as described below. The invention is further directed to medicaments of a humanized anti-PAI-1 antibody or antigen binding fragment thereof described hereinabove and a pharmaceutically acceptable carrier.

Provided herein are compositions of humanized antibodies and antigen-binding fragments thereof that bind PAI-1 and include those such as described elsewhere herein. Humanized antibodies and antigen-binding fragments thereof that bind PAI-1 as described herein can be used for the treatment of diabetic nephropathy and various diabetes associated indications such as obesity and insulin resistance syndrome.

A composition (an antibody or an antigen-binding fragment described herein) can be administered alone or in combination with a second composition (an antibody or an antigen-binding fragment described herein), either simultaneously or sequentially dependent upon the condition to be treated. The present application also contemplates and includes compositions comprising two or more antibodies or antigen-binding fragments thereof, herein described. In one embodiment, a second therapeutic treatment is a second form of a humanized anti-PAI-1 antibody described herein containing different modifications from a first form of a humanized anti-PAI-1 antibody. When two or more compositions are administered, the compositions can be administered in combination (either sequentially or simultaneously). A composition can be administered in a single dose or multiple doses.

III. Methods of Use

Compositions of antibodies and antigen-binding fragments described herein can be used as non-therapeutic agents (e.g., as affinity purification agents). Generally, in one such embodiment, a protein of interest is immobilized on a solid phase such a Sephadex resin or filter paper, using conventional methods known in the art. The immobilized protein is contacted with a sample containing the target of interest (or fragment thereof) to be purified, and thereafter the support is washed with a suitable solvent that will remove substantially all the material in the sample except the target protein, which is bound to the immobilized antibody. Finally, the support is washed with another suitable solvent, such as glycine buffer, pH 5.0, which will release the target protein. In addition to purification, compositions can be used for detection, diagnosis and therapy of diseases and disorders associated with PAI-1.

The term "contacting" as used herein refers to adding together a solution or composition of a compound with a liquid medium bathing the polypeptides, cells, tissue or organ from an organism. Alternately, "contacting" refers to mixing together a solution or composition of a compound, with a liquid such as blood, serum, or plasma derived from an organism. For in vitro applications, the solution can also comprise another component, such as dimethyl sulfoxide (DMSO). DMSO facilitates the uptake of the compounds or solubility of the compounds. The solution comprising the test compound may be added to the medium bathing the cells, tissues, or organs, or mixed with another liquid such as blood, by utilizing a delivery apparatus, such as a pipette-based device or syringe-based device. For in vivo applications, contacting can occur, for example, via administration of a composition to a patient by any suitable means.

A "patient" according to one embodiment of the present application, is a mammal (e.g., a human) who exhibits one or more clinical manifestations and/or symptoms of a disease or disorder described herein. In certain situations, the patient may be asymptomatic and yet still have clinical manifestations of the disease or disorder.

An antibody or antigen-binding fragment thereof can be conjugated to a therapeutic moiety or be a fusion protein containing a therapeutic moiety. An antibody or antigen-binding fragment thereof can be conjugated to a detectable moiety or be a fusion protein containing a detectable moiety. In one embodiment, the antibody or antigen-binding fragment thereof can be conjugated to both a therapeutic moiety and a detectable moiety. An antibody or antigen-binding fragment thereof can be conjugated to, or recombinantly engineered with, an affinity tag (e.g., a purification tag).

Antibodies or antigen-binding fragments thereof provided herein are such that they can be conjugated or linked to a therapeutic moiety and/or an imaging or a detectable moiety and/or an affinity tag. Methods for conjugating or linking polypeptides are well known in the art. Associations (binding) between compounds and labels include any means known in the art including, but not limited to, covalent and non-covalent interactions, chemical conjugation as well as recombinant techniques.

A. Neutralization of PAI-1 and Fibrinolysis

Persistence of venous, arterial, and tissue/organ thrombi involves the tissue plasminogen activator inhibitor PAI-1. tPA and/or uPA activates plasmin, the active form of plasminogen, and plasmin is directly involved in the pathways for the degradation or breakdown of fibrin (fibrinolysis), thrombi in general (thrombolysis), as well as extra-cellular matrices (ECM). PAI-1, in its active form, inhibits tPA and uPA and thus directly effects the breakdown of fibrin, thrombi and ECM.

The antibodies and antigen-binding fragments described herein inhibit or neutralize PAI-1 by converting the active form of PAI-1 to the latent form. Alternatively, antibodies and antigen-binding fragments described herein inhibit or neutralize PAI-1 by decreasing complex formation between PAI-1 and its target proteinases and by increasing cleavable PAI-1. Provided herein are compositions and methods for the treatment and/or modulation of fibrinolysis. Also provided herein are compositions and methods for the treatment and/or modulation of thrombolysis. Further provided herein are compositions and methods for the treatment and/or modulation of the degradation of ECM. In one non-limiting example, the antibodies or antigen-binding fragments described herein are administered to induce a conformational change from the active form of PAI-1 to the latent form of PAI-1. In another non-limiting example, antibodies or antigen-binding fragments described herein are administered to decrease complex formation between PAI-1 and its target proteinases and increase cleavable PAI-1. In another non-limiting example, the antibodies or antigen-binding fragments described herein are administered to modulate the breakdown of fibrin. In another non-limiting example, the antibodies or antigen-binding fragments described herein are administered to decrease the persistence of thrombi. In yet another non-limiting example, the antibodies or antigen-binding fragments described herein are administered to modulate the degradation of the extra-cellular matrix.

B. Diagnostic Applications

Humanized anti-PAI-1 antibodies and fragments thereof can be used for in vivo and in vitro detection, diagnostic and/or monitoring purposes. PAI-1 (and in some cases, excess PAI-1) is believed to be involved in multiple diseases and disorders as described further below. Treatment of PAI-1 related diseases and conditions depends, in part, upon their diagnosis, and the antibodies and antigen-binding fragments thereof described herein are useful for the diagnosis of excess PAI-1 or for diagnosis for diseases and conditions associated with PAI-1 activity.

Provided herein is method of detecting levels of PAI-1 in a sample or a subject comprising (i) contacting an antibody or antigen binding fragment described herein with the sample or subject, and (ii) detecting a complex of the antibody or antigen-binding fragment thereof and PAI-1.

In one embodiment, the antibody or antigen-binding fragment further comprises a detectable moiety. Detection can occur in vitro, in vivo or ex vivo. In vitro assays for the detection and/or determination (quantification, qualification, etc.) of PAI-1 with the antibodies or antigen-binding fragments thereof include but are not limited to, for example, ELISAs, RIAs and western blots. In vitro detection, diagnosis or monitoring of PAI-1 can occur by obtaining a sample (e.g., a blood sample) from a patient and testing the sample in, for example, a standard ELISA assay. For example, a 96-well microtiter plate can be coated with an antibody or antigen-binding fragment thereof described herein, washed and coating with PBS-Tween/BSA to inhibit non-specific binding. The blood sample can be serially diluted and placed in duplicate wells compared to a serially-diluted standard curve of PAI-1. After incubating and washing the wells, an anti-PAI-1 antibody labeled with biotin can be added, followed by addition of streptavidin-alkaline phosphatase. The wells can be washed and a substrate (horseradish peroxidase) added to develop the plate. The plate can be read using a conventional plate reader and software.

When detection occurs in vivo, contacting occurs via administration of the antibody or antigen binding fragment using any conventional means such as those described elsewhere herein. In such methods, detection of PAI-1 (and in some cases excess levels of PAI-1) in a sample or a subject can be used to diagnose a disease or disorder associated with, or correlated with the activity of PAI-1 such as those diseases and disorders described herein.

In the in vivo detection, diagnosis or monitoring of PAI-1, a patient is administered an antibody or antigen-binding fragment that binds to PAI-1, which antibody or antigen-binding fragment is bound to a detectable moiety. The detectable moiety can be visualized using art-recognized methods such as, but not limited to, magnetic resonance imaging (MRI), fluorescence, radioimaging, light sources supplied by endoscopes, laparoscopes, or intravascular catheter (i.e., via detection of photoactive agents), photoscanning, positron emission tomography (PET) scanning, whole body nuclear magnetic resonance (NMR), radioscintography, single photon emission computed tomography (SPECT), targeted near infrared region (NIR) scanning, X-ray, ultrasound, etc. such as described, for example, in U.S. Pat. Nos. 6,096,289, 7,115, 716, 7,112,412, U.S. Patent Application No. 20030003048 and U.S. Patent Application No. 20060147379, each of which is incorporated herein in its entirety by reference. Labels for detecting compounds using such methods are also known in the art and described in such patents and applications and are incorporated herein by reference. Visualization of the detectable moiety can allow for detection, diagnosis, and/or monitoring of a condition or disease associated with PAI-1.

Additional diagnostic assays that utilize antibodies specific to the desired target protein, i.e., PAI-1, are known in the art and are also contemplated herein.

Non-limiting conditions, diseases and disorders to be considered for these methods include, but are not limited to, those associated with fibrinolysis or thrombosis such as, for example, diabetic nephropathy and diabetes-associated conditions and cardiovascular diseases (e.g., ischemic heart disease, arteriosclerosis, atherosclerosis, hypertension, angina, hear attack, stroke, deep vein thrombosis, disseminated intravascular coagulation, premature myocardial infarction and coronary heart disease. In the detection, diagnosis or monitoring of such diseases, the subject patient is administered a composition of an antibody or antigen-binding fragment thereof described herein, which antibody or antigen-binding fragment thereof is conjugated to a detectable moiety. The moiety can be visualized using art-recognized methods such as those described above. Visualization of the detectable moiety can allow for detection, diagnosis, and/or monitoring of such conditions and diseases.

For in vitro detection methods, samples to be obtained from a patient include, but are not limited to, blood, tissue biopsy samples and fluid therefrom.

Thus, the present invention provides humanized antibodies and antigen-binding fragments thereof against PAI-1 which are useful for detecting or diagnosing excess levels of PAI-1 or PAI-1 associated with a disease or disorder, potentially indicating need for therapeutic treatment. In certain embodiments, the antibodies comprise a humanized anti-PAI-1 antibody described herein. In other embodiments the antibody further comprises a second agent. Such an agent can be a molecule or moiety such as, for example, a reporter molecule or a detectable label. Detectable labels/moieties for such detection methods are known in the art and are described in more detail below. Reporter molecules are any moiety which can be detected using an assay. Non-limiting examples of reporter molecules which have been conjugated to polypeptides include enzymes, radiolabels, haptens, fluorescent labels, phosphorescent molecules, chemiluminescent molecules, chromophores, luminescent molecules, photoaffinity molecules, colored particles or ligands, such as biotin. Detectable labels include compounds and/or elements that can be detected due to their specific functional properties, and/or chemical characteristics, the use of which allows the polypeptide to which they are attached to be detected, and/or further quantified if desired. Many appropriate detectable (imaging) agents are known in the art, as are methods for their attachment to polypeptides (see, for e.g., U.S. Pat. Nos. 5,021, 236; 4,938,948; and 4,472,509, each of which is hereby incorporated by reference).

Methods of joining polypeptides such as antibodies with detectable moieties are known in the art and include, for example, recombinant DNA technology to form fusion proteins and conjugation (e.g., chemical conjugation). Methods for preparing fusion proteins by chemical conjugation or recombinant engineering are well-known in the art. Methods of covalently and non-covalently linking components are also known in the art. See, e.g., Williams (1995) Biochemistry 34:1787 1797; Dobeli (1998) Protein Expr. Purif. 12:404-414; and Kroll (1993) DNA Cell. Biol. 12: 441-453.

It may be necessary, in some instances, to introduce an unstructured polypeptide linker region between a label or a moiety and one or more portion of the antibodies, antigen-binding fragments or binding proteins described herein. A linker can facilitate enhanced flexibility, and/or reduce steric hindrance between any two fragments. The linker can also facilitate the appropriate folding of each fragment to occur. The linker can be of natural origin, such as a sequence determined to exist in random coil between two domains of a protein. One linker sequence is the linker found between the C-terminal and N-terminal domains of the RNA polymerase a subunit. Other examples of naturally occurring linkers include linkers found in the 1CI and LexA proteins.

Within a linker, an amino acid sequence can be varied based on the characteristics of the linker as determined empirically or as revealed by modeling. Considerations in choosing a linker include flexibility of the linker, charge of the linker, and presence of some amino acids of the linker in the naturally-occurring subunits. The linker can also be designed such that residues in the linker contact deoxyribose nucleic acid (DNA), thereby influencing binding affinity or specificity, or to interact with other proteins. In some cases, such as when it is necessary to span a longer distance between subunits or when the domains must be held in a particular configuration, the linker can, optionally, contain an additional folded domain. In some embodiments, the design of a linker can involve an arrangement of domains which requires the linker to span a relatively short distance, e.g., less than about 10 Angstroms (Å). However, in certain embodiments, linkers span a distance of up to about 50 Angstroms.

Within the linker, the amino acid sequence can be varied based on the characteristics of the linker as determined empirically or as revealed by modeling. Considerations in choosing a linker include flexibility of the linker, charge of the linker, and presence of some amino acids of the linker in the naturally-occurring subunits. The linker can also be designed such that residues in the linker contact DNA, thereby influencing binding affinity or specificity, or to interact with other proteins. In some cases, when it is necessary to span a longer distance between subunits or when the domains must be held in a particular configuration, the linker can optionally contain an additional folded domain.

Methods for coupling polypeptides (free or cell-bound) to beads are known in the art. Methods for selecting coupled polypeptides or cells displaying a polypeptide are also known in the art. Briefly, paramagnetic polystyrene microparticles are commercially available (Spherotech, Inc., Libertyville, Ill.; Invitrogen, Carlsbad, Calif.) that couple peptides to microparticle surfaces that have been modified with functional groups or coated with various antibodies or ligands such as, for example, avidin, streptavidin or biotin.

The paramagnetic property of microparticles allows them to be separated from solution using a magnet. The microparticles can be easily re-suspended when removed from the magnet. Polypeptides can be coupled to paramagnetic polystyrene microparticles coated with a polyurethane layer in a tube. The hydroxy groups on the microparticle surface are activated by reaction with p-toluensulphonyl chloride (Nilsson K and Mosbach K. "p-Toluenesulfonyl chloride as an activating agent of agarose for the preparation of immobilized affinity ligands and proteins." Eur. J. Biochem. 1980: 112: 397-402). Alternatively, paramagnetic polystyrene microparticles containing surface carboxylic acid can be activated with a carbodiimide followed by coupling to a polypeptide, resulting in a stable amide bond between a primary amino group of the polypeptide and the carboxylic acid groups on the surface of the microparticles (Nakajima N and Ikade Y, Mechanism of amide formation by carbodiimide for bioconjugation in aqueous media, Bioconjugate Chem. 1995, 6(1), 123-130; Gilles M A, Hudson A Q and Borders C L Jr, Stability of water-soluble carbodiimides in aqueous solution, Anal Biochem. 1990 Feb. 1; 184(2):244-248; Sehgal D and Vijay I K, a method for the high efficiency of water-soluble carbodiimide-mediated amidation, Anal Biochem. 1994 April; 218(1):87-91; Szajani B et al, Effects of carbodimide structure on the immobilization of enzymes, Appl Biochem Biotechnol. 1991 August; 30(2):225-231). Another option is to couple biotinylated polypeptides to paramagnetic polystyrene microparticles whose surfaces have been covalently linked with a monolayer of streptavidin. (Argarana C E, Kuntz I D, Birken S, Axel R, Cantor C R. Molecular cloning and nucleotide sequence of the streptavidin gene. Nucleic Acids Res. 1986; 14(4):1871-82; Pahler A, Hendrickson W A, Gawinowicz Kolks M A, Aragana C E, Cantor C R. Characterization and crystallization of core streptavidin. J Biol Chem 1987:262 (29):13933-7).

Polypeptides can be conjugated to a wide variety of fluorescent dyes, quenchers and haptens such as fluorescein, R-phycoerythrin, and biotin. Conjugation can occur either during polypeptide synthesis or after the polypeptide has been synthesized and purified. Biotin is a small (244 kilodaltons) vitamin that binds with high affinity to avidin and streptavidin proteins and can be conjugated to most peptides without altering their biological activities. Biotin-labeled polypeptides are easily purified from unlabeled polypeptides using immobilized streptavidin and avidin affinity gels, and streptavidin or avidin-conjugated probes can be used to detect biotinylated polypeptides in, for example, ELISA, dot blot or Western blot applications. N-hydroxysuccinimide esters of biotin are the most commonly used type of biotinylation agent. N-hydroxysuccinimide-activated biotins react efficiently with primary amino groups in physiological buffers to form stable amide bonds. Polypeptides have primary amines at the N-terminus and can also have several primary amines in the side chain of lysine residues that are available as targets for labeling with N-hydroxysuccinimide-activated biotin reagents. Several different N-hydroxysuccinimide esters of biotin are available, with varying properties and spacer arm length (Pierce, Rockford, Ill.). The sulfo-N-hydroxysuccinimide ester reagents are water soluble, enabling reactions to be performed in the absence of organic solvents.

The mole-to-mole ratio of biotin to polypeptide can be estimated using a 2-(4'-Hydroxyazobenzene-2-carboxylic acid) assay using art-recognized techniques (Green, N M, (1975) "Avidin. In Advances in Protein Chemistry." Academic Press, New York. 29, 85-133; Green, N M, (1971) "The use of bifunctional biotinyl compounds to determine the arrangement of subunits in avidin." Biochem J. 125, 781-791; Green, N M., (1965) "A spectrophotometric assay for avidin and biotin based on binding of dyes by avidin." Biochem. J. 94: 23c-24c). Several biotin molecules can be conjugated to a polypeptide and each biotin molecule can bind one molecule of avidin. The biotin-avidin bond formation is very rapid and stable in organic solvents, extreme pH and denaturing reagents. To quantitate biotinylation, a solution containing the biotinylated polypeptide is added to a mixture of 2-(4'-Hydroxyazobenzene-2-carboxylic acid) and avidin. Because biotin has a higher affinity for avidin, it displaces the 2-(4'-Hydroxyazobenzene-2-carboxylic acid) and the absorbance at 500 nanometers decreases proportionately. The amount of biotin in a solution can be quantitated in a single cuvette by measuring the absorbance of the 2-(4'-Hydroxyazobenzene-2-carboxylic acid)-avidin solution before and after addition of the biotin-containing peptide. The change in absorbance relates to the amount of biotin in the sample by the extinction coefficient of the 2-(4'-Hydroxyazobenzene-2-carboxylic acid)-avidin complex.

Alternatively, an antibody, antigen-binding fragment or binding protein can be conjugated with a fluorescent moiety Conjugating polypeptides with fluorescent moieties (e.g., R-Phycoerythrin, fluorescein isothiocyanate (FITC), etc.) can be accomplished using art-recognized techniques described in, for example, Glazer, A N and Stryer L. (1984). Trends Biochem. Sci. 9:423-7; Kronick, M N and Grossman, P D (1983) Clin. Chem. 29:1582-6; Lanier, L L and Loken, M R (1984) J. Immunol., 132:151-156; Parks, D R et al. (1984) Cytometry 5:159-68; Hardy, R R et al. (1983) Nature 306:

270-2; Hardy R R et al. (1984) J. Exp. Med. 159:1169-88; Kronick, M N (1986) J. Immuno. Meth. 92:1-13; Der-Balian G, Kameda, N. and Rowley, G. (1988) Anal. Biochem. 173: 59-63.

In one non-limiting embodiment, an antibody antigen-binding fragment can be associated with (conjugated to) a detectable label, such as a radionuclide, iron-related compound, a dye, an imaging agent or a fluorescent agent for immunodetection of PAI-1 which can be used to visualize binding of the antibodies to PAI-1 in vitro and/or in vivo.

Non-limiting examples of radiolabels include, for example, $^{32}P$, $^{33}P$, $^{43}K$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{77}Br$, $^{81}Rb/^{81}MKr$, $^{87}MSr$, $^{90}Y$, $^{97}Ru$, $^{99}Tc$, $^{100}Pd$, $^{101}Rh$, $^{103}Pb$, $^{105}Rh$, $^{109}Pd$, $^{111}Ag$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Eu$, $^{177}Lu$, $^{186}Re$, $^{188}Re$, $^{189}Re$, $^{191}Os$, $^{193}Pt$, $^{194}Ir$, $^{197}Hg$, $^{199}Au$, $^{203}Pb$, $^{211}At$, $^{212}Pb$, $^{212}Bi$ and $^{213}Bi$. Radiolabels can be attached to compounds using conventional chemistry known in the art of antibody imaging. Radiolabeled compounds are useful in in vitro diagnostics techniques and in in vivo radioimaging techniques and in radioimmunotherapy. For example, in the instance of in vivo imaging, the antibodies and antigen-binding fragments thereof can be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanium, holmium and ferbium. Such detectable moieties also include: metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nanocompounds; magnetic resonance imaging contrast agents; light absorbing, reflecting and/or scattering agents; colloidal particles; fluorophores, such as near-infrared fluorophores. In many embodiments, such secondary functionality/moiety will be relatively large, e.g., at least 25 amu in size, and in many instances can be at least 50, 100 or 250 amu in size. In certain embodiments, the secondary functionality is a chelate moiety for chelating a metal, e.g., a chelator for a radiometal or paramagnetic ion. In embodiments, it is a chelator for a radionuclide useful for radiotherapy or imaging procedures.

C. Treatment with Humanized PAI-1 Antibodies

Provided herein are methods of preventing or treating one or more diseases or disorders associated with PAI-1 comprising administering a composition comprising a humanized antibody or antigen-binding fragment described herein that binds to PAI-1 associated with the disease or disorder and converts PAI-1 to its latent form thereby inhibiting interaction of PAI-1 with tPA and/or uPA.

Provided herein are methods of preventing or treating one or more diseases or disorders associated with PAI-1 comprising administering a composition comprising a humanized antibody or antigen-binding fragment described herein that binds to PAI-1 associated with the disease or disorder, decreases complex formation between PAI-1 and its target proteinases and increases cleavable PAI-1.

As used herein, "prevention" refers to prophylaxis, prevention of onset of symptoms, prevention of progression of a disease or disorder associated with excess levels of PAI-1 or correlated with PAI-1 activity. As used herein, "inhibition," "treatment" and "treating" are used interchangeably and refer to, for example, stasis of symptoms, prolongation of survival, partial or full amelioration of symptoms, and partial or full eradication of a condition, disease or disorder associated with excess levels of PAI-1 or correlated with PAI-1 activity. As further used herein, treatment of cancer includes stasis, partial or total elimination of a cancerous growth or tumor. Treatment or partial elimination includes, for example, a fold reduction in growth or tumor size and/or volume such as about 2-fold, about 3-fold, about 4-fold, about 5-fold, about 10-fold, about 20-fold, about 50-fold, or any fold reduction in between. Similarly, treatment or partial elimination can include a percent reduction in growth or tumor size and/or volume of about 1%, 2%, 3%, 4%, 5%, 10%, 20%, 30%, 40%, 50%, 60%, 70%, 80%, 90%, 95% or any percentage reduction in between.

Compositions can be administered to a patient (e.g., a mammal such as a human or a non-human animal such as a primate, rodent, cow, horse, pig, sheep, etc.) in a therapeutically effective amount which are effective for producing some desired therapeutic effect by inhibiting a disease or disorder such as described herein which can be associated with PAI-1, at a reasonable benefit/risk ratio applicable to any medical treatment. For the administration of the present compositions to human patients, the compositions can be formulated by methodology known by one of ordinary skill in the art. A therapeutically effective amount is an amount achieves at least partially a desired therapeutic or prophylactic effect in an organ or tissue. In one example, the amount of a humanized anti-PAI-1 antibody or antigen binding fragment thereof necessary to bring about prevention and/or therapeutic treatment of a disease or disorder is not fixed per se. The amount of humanized anti-PAI-1 antibody or antigen binding fragment thereof administered will vary with the type of disease, extensiveness of the disease, and size of the mammal suffering from the disease or disorder. In one embodiment, two or more humanized anti-PAI-1 antibodies described herein are administered to a patient in combination. Combination includes concomitant or subsequent administration of the antibodies.

A response is achieved when the patient experiences partial or total alleviation, or reduction of signs or symptoms of illness, and specifically includes, without limitation, prolongation of survival. The expected progression-free survival times can be measured in months to years, depending on prognostic factors including the number of relapses, stage of disease, and other factors. Prolonging survival includes without limitation times of at least 1 month (mo), about at least 2 months (mos.), about at least 3 mos., about at least 4 mos., about at least 6 mos., about at least 1 year, about at least 2 years, about at least 3 years, etc. Overall survival can also be measured in months to years. The patient's symptoms can remain static or can decrease.

A physician or veterinarian having ordinary skill in the art can readily determine and prescribe the effective amount (ED50) of the composition required. For example, the physician or veterinarian could start doses of the compounds employed in the composition at levels lower than that required in order to achieve the desired therapeutic effect and gradually increase the dosage until the desired effect is achieved.

Compositions can be administered to a patient by any convenient route such as described above. Regardless of the route of administration selected, the compounds of the present invention, which can be used in a suitable hydrated form, and/or the compositions, are formulated into acceptable dosage forms such as described below or by other conventional methods known to those of skill in the art.

Actual dosage levels of the active ingredients in the compositions can be varied so as to obtain an amount of the active ingredient that is effective to achieve the desired therapeutic response for a particular patient, composition, and mode of administration, without being toxic to the patient. The selected dosage level will depend upon a variety of factors including the activity of the particular compound employed, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts.

Antibodies can be combined with a therapeutic moiety or to a detectable (imaging) moiety using methods known in the art such as, for example, chemical conjugation, covalent or non-covalent bonds or recombinant techniques to create conjugates or fusion proteins such as described in more detail below. Alternatively, antibodies and/or other agents can be combined in separate compositions for simultaneous or sequential administration.

The unique specificity of the antibodies which recognize (e.g., bind) an epitope on PAI-1 and promotes conversion of PAI-1 to its latent form, thereby inhibiting binding of PAI-1 to tPA and/or uPA, provides diagnostic and therapeutic uses to in diseases characterized by thrombosis and fibrinolysis such as described herein.

The unique specificity of the antibodies which recognize (e.g., bind) an epitope on PAI-1, decreases complex formation between PAI-1 and its target proteinases and increases cleavable PAI-1, thereby inhibiting binding of PAI-1 to tPA and/or uPA, provides diagnostic and therapeutic uses to in diseases characterized by thrombosis and fibrinolysis such as described herein.

Humanized anti-PAI-1 antibodies and fragments thereof can be administered to a subject such as a mammal (e.g., a human), suffering from a medical disorder, e.g., diabetic nephropathy which a targeting ligand can selectively bind. PAI-1 is believed to be involved in the etiology of diabetic nephropathy (Baricos, et al., Extracellular Matrix Degradation by Cultured Mesangial Cells: Mediators and Modulators (2003) Exp. Biol. Med. 228:1018-1022). Provided herein is a method for treating a subject having chronic kidney disease by administering a humanized antibody or fragment thereof described herein that binds PAI-1 and inhibits binding of PAI-1 to tPA and/or uPA by converting PAI-1 to its latent form. Further provided herein is a method of treating a subject having diabetic nephropathy by administering a humanized antibody or fragment thereof described herein that binds PAI-1 and inhibits binding of PAI-1 to tPA and/or uPA by converting PAI-1 to its latent form. Further provided herein is a method of treating a subject having diabetic nephropathy by administering a humanized antibody or fragment thereof described herein that binds PAI-1, decreases complex formation between PAI-1 and its target proteinases and increases cleavable PAI-1.

PAI-1 is also believed to be involved in the causes of obesity (Li-Jun Ma, et al., Prevention of Obesity and Insulin Resistance in Mice Lacking Plasminogen Activator Inhibitor 1 (February 2004) Diabetes, Vol. 53, pp. 336-346.). Provided herein is a method of treating obesity by administering a humanized antibody or fragment thereof described herein that binds PAI-1. Similarly, PAI-1 is further believed to be involved in insulin resistance syndrome and/or metabolic syndrome. Further provided herein is a method of treating insulin resistance syndrome by administering a humanized antibody or fragment thereof described herein that binds PAI-1 and inhibits binding of PAI-1 to tPA and/or uPA by converting PAI-1 to its latent form. Further provided herein is a method of treating insulin resistance syndrome by administering a humanized antibody or fragment thereof described herein that binds PAI-1, decreases complex formation between PAI-1 and its target proteinases and increases cleavable PAI-1.

PAI-1 is further known to be involved in the persistence of thrombi and cardiovascular diseases (Naya et al., *Elevated Plasma Plaminogen Activator Inhibitor Type-1 is an Independent Predictor of Coronary Microvascular Dysfunction in Hypertension*, Circ. J., 71: 348-353 (2007); Smith et al., *Which Hemostatic Markers Add to the Predictive Value of Conventional Risk Factors for Coronary Heart Disease and Ischemic Stroke?*, Circulation, 112:3080-3087 (2005)). Provided herein is a method of decreasing the persistence of thrombi. Further provided herein is a method of treating cardiovascular disease via administering a humanized antibody or fragment thereof described herein that binds PAI-1. Exemplary cardiovascular diseases contemplated herein include, but are not limited to, ischemic heart disease, arteriosclerosis, atherosclerosis, hypertension, angina, heart attack, stroke, deep vein thrombosis, disseminated intravascular coagulation, premature myocardial infarction, peripheral artery disease and coronary artery disease. Further provided herein is a method of treating a cardiovascular disease by administering a humanized antibody or fragment thereof described herein that binds PAI-1 and inhibits binding of PAI-1 to tPA and/or uPA by converting PAI-1 to its latent form. Further provided herein is a method of treating a cardiovascular disease by administering a humanized antibody or fragment thereof described herein that binds PAI-1, decreases complex formation between PAI-1 and its target proteinases and increases cleavable PAI-1.

PAI-1 is also believed to be involved in the establishment and progression of Alzheimer's disease and the degradation of beta-amyloid deposits. (Wang et al., *Beta-Amyloid Degradation and Alzheimer's Disease*, J. Biomedicine and Biotech., 2006: 1-12 (2006); Tucker et al., *Tissue Plasminogen Activator Requires Plasminogen to Modulate Amyloid-beta Nerotoxicity and Deposition*, J. Neurochem. 75:2172-2177 (2000)). Provided herein is a method of decreasing the persistence of beta-amyloid. Further provided herein is a method of treating Alzheimer's disease via administering a humanized antibody or fragment thereof described herein that binds PAI-1.

PAI-1 is believed to be involved in acute respiratory distress syndrome (ARDS). (Ware et al., *Coagulation and fibrinolysis in human acute lung injury—New therapeutic targets?*, Keio J. Med. 54(3): 142-149 (2005)). Furthermore, PAI-1 is also believed to be involved in idiopathic pulmonary fibrosis (IPF). (Thomas Geiser, *Idiopathic pulmonary fibrosis—a disorder of alveolar wound repair*, Swiss Med. Wkly, 133: 405-411 (2003)). Provided herein is a method for increasing fibrinolysis in the lungs. Also provided herein is a method for decreasing fibrin deposition in the lungs. Further provided herein is a method of treating ARDS via the administration of a humanized antibody or fragment thereof described herein that binds PAI-1. Also provided herein is a method of treating IPF via the administration of a humanized antibody or fragment thereof described herein that binds PAI-1.

PAI-1 is further correlated with the persistence of malignant tumors or cancerous growths where the cancer or tumor expresses high levels of PAI-1. (Dellas et al., *Historical analysis of PAI-1 from its discovery to its potential role in cell motility and disease*, Thomb. Haemost., 93: 631-40 (2005)).

It is believed that high levels of PAI-1 may contribute to metastasis and/or angiogenesis in cancerous growths or tumors. Provided herein is a method of treating cancer by administering a humanized antibody or fragment thereof described herein that binds PAI-1.

Toxicity and therapeutic efficacy of such ingredient can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. While compounds that exhibit toxic side effects may be used, care should be taken to design a delivery system that targets such compounds to the site of affected tissue in order to minimize potential damage to healthy cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration arrange that includes the $IC_{50}$ (i.e., the concentration of the test compound which achieves a half-maximal inhibition of symptoms) as determined in cell culture. Levels in plasma can be measured, for example, by high performance liquid chromatography. Such information can be used to more accurately determine useful doses in humans.

Fibrotic Conditions

A variety of conditions are characterized by excess accumulation of extracellular matrix (collagen, fibronectin and other matrix components). Such conditions include, but are not limited to, fibrotic diseases of the kidney (e.g., glomerulonephritis, diabetes-associated pathologies such as diabetic kidney disease), fibrotic diseases of the respiratory system (e.g., adult or acute respiratory distress syndrome (ARDS), asthma, COPD), fibrotic diseases of the liver (e.g., due to cirrhosis, hepatitis C viral (HCV) infection, hepatitis B viral (HBV) infection, non-alcoholic steatohepatitis (NASH), etc.), and post infarction cardiac fibrosis. Also included are fibrocystic diseases such as fibrosclerosis and fibrotic cancers such as, but not limited to, cancers of the breast, uterus, pancreas or colon, and including fibroids, fibroma, fibroadenomas and fibrosarcomas. Such conditions also include, for example, fibrosis occurring post-transplantation of organs or any of the other indications described herein.

There are also a number of medical conditions associated with an excess accumulation of extracellular matrix involving increased collagen, fibronectin and other matrix components. Such conditions include, for example, but are not limited to, post myocardial infarction, left ventricular hypertrophy, pulmonary fibrosis, liver cirrhosis, veno-occlusive disease, post-spinal cord injury, post-retinal and glaucoma surgery, post-angioplasty restenosis and renal interstitial fibrosis, arteriovenous graft failure, endometriosis, excessive scarring such as keloid scars and scars resulting from injury, burns or surgery.

Excess deposition and accumulation of extracellular matrix (ECM) is found in diseases such as fibrosis of the kidney or lung. (Border and Ruoslahti, J. Clin. Invest. 90:1-7 (1992)). Fibrogenic action results from simultaneous stimulation of matrix protein synthesis (Border et al., Kidney Int 37:689-695 (1990), inhibition of matrix degradation and turnover and enhanced cell-matrix interactions through modulation of integrin receptors that facilitate ECM assembly.

Dermal scarring following dermal injury results from excessive accumulation of fibrous tissue made up of collagen, fibronectin and proteoglycans at a wound site. Because the fibrous extracellular matrix lacks elasticity, scar tissue can impair essential tissue function as well as result in an undesirable cosmetic appearance (Shah et al., Lancet 339:213-214 (1992)).

Soon after a wound occurs in a subject, the wound healing process starts with a coagulation of fibrin and fibronectin to form a matrix or a clot and a gathering of platelets at the wound site. As the platelets coagulate, inflammatory cells, such as neutrophils, lymphocytes, and macrophages, are also attracted to the wound site and release factors for wound healing. For example, macrophages secrete cytokines and growth factors such as fibroblast growth factors (FGF), platelet-derived growth factors (PDGF), tumor necrosis growth factors (TNF-alpha), vascular endothelial growth factors (VEGF), interleukin-1 (IL-1), interferon-gamma (INF-gamma); and an epidermal growth factor-like substance. Activated platelets also release epidermal growth factor (EGF), PDGF, transforming growth factors alpha, beta1, and beta2 (TGF-alpha, TGF-alpha, and TGF-beta, respectively); platelet derived epidermal growth factor (PDEGF), platelet-activating factor (PAF), insulin-like growth factor-1 (INF-1), fibronectin, and serotonin. Together these biological factors are involved in the infiltration, proliferation, and migration of keratinocytes, fibroblasts, and endothelial cells. Towards the end of the inflammation phase, proteins, fats, and cross-linked new collagen aggregate together and form a transient scaffold.

During the migration and proliferation phase, cells that have migrated into the wound site undergo rapid mitosis and differentiation. These cells include keratinocytes and fibroblasts. On one hand, keratinocytes undergo an epithelization process in which the cells stratify and differentiate to form an epidermal covering. Keratinocytes also release keratinocyte growth factor (KGF) and VEGF to stimulate angiogenesis, TGF-alpha as a chemoattractant, PDGF to promote extracellular matrix (ECM) formation, and proteases to dissolve non-viable tissue and fibrin barriers. Migrated fibroblasts, on the other hand, synthesize and deposit collagen and proteoglycans, release growth factors such as KGF, connective tissue growth factors (CTGF), plasminogen activator inhibitor-1 (PAI-1) and TGF-beta. Like the keratinocytes, fibroblasts also release proteases that expedite the subsequent remodeling process. All these cellular activities such as migration, proliferation, differentiation, degradation of the transient scaffold, and synthesis of a new matrix in the migration and proliferation phase are often described as a fibroplasia process.

The final stage of wound healing is involved in a remodeling process which changes the deposition pattern of matrix components. As described, the initial matrix is a clot of fibrin and fibronectin resulting from homeostasis. With the proliferation and migration of fibroblasts, collagen is synthesized and deposited replacing and rearranging the initial matrix with aid from proteases. Collagen fibers gradually increase in thickness and align along the stress line of the wound. At the end of normal scar formation, the final scar shows collagen fibers mostly parallel to the epidermis. (See, Hunt et al., Physiology of Wound Healing, Adv. Skin Wound Care 13: 6-11 (2000); Ferguson et al., Plas. Reconstr. Surg. 97: 854-60 (1996); Gailit & Clark, Curr. Opin. Cell Biol. 6: 717-25 (1994)).

The present invention relates to reducing the activity of Plasminogen Activator Inhibitor-1 (PAI-1) to suppress an excessive deposition of collagen which is known as a cause for the formation of abnormal scars. These abnormal scars include but are not limited to keloids, adhesions, hypertrophic scars, skin disfiguring conditions, fibrosis, fibrocystic conditions, contractures, and scleroderma, all of which are associated with or caused by an excessive deposit of collagen in a wound healing process. If needed, PAI-1 activity in a wound healing process can be measured to determine the propensity of the formation of an abnormal scar. Accordingly, aspects of the present invention are directed to the reduction of PAI-1 activity to decrease an excessive accumulation of collagen, prevent the formation of an abnormal scar, and/or treat abnormal scars that result from an excessive accumulation of collagen.

The humanized antibodies and antigen-binding fragments which bind PAI-1 and are described herein can be used to treat fibrotic conditions. Described herein are methods of treating or preventing fibrotic conditions via the administration of the antibodies and antigen-binding fragments described herein. The humanized antibodies and antigen-binding fragments described herein can also be used in medicaments for the treatment of fibrotic conditions described herein.

The humanized antibodies and antigen-binding fragments which bind PAI-1 and are described herein can be used to treat fibrosis associated with wound healing. Described herein are methods of treating or preventing fibrosis associated with wound healing via the administration of the antibodies and antigen-binding fragments described herein. The humanized antibodies and antigen-binding fragments described herein can also be used in medicaments for the treatment of fibrosis associated with wound healing.

The humanized antibodies and antigen-binding fragments which bind PAI-1 and are described herein can be used to treat liver fibrosis. Described herein are methods of treating or preventing liver fibrosis via the administration of the antibodies and antigen-binding fragments described herein. The humanized antibodies and antigen-binding fragments described herein can also be used in medicaments for the treatment of liver fibrosis. Various liver fibrosis models are available for assessment of the effect of anti-PAI-1 on disease indications: Ferru et al. Scand. J. Immunol. 48: 233-240 (1998); Safadi et al. Gastroenterology 127: 870-882 (2004); Novobrantseva et al. J. Clin. Invest. 115: 3072-3082 (2005); Chiaramonte et al. J. Clin. Invest. 104: 777-785 (1999); Shi et al. PNAS USA 94: 10663-10668 (1997).

The humanized antibodies and antigen-binding fragments which bind PAI-1 and are described herein can be used to treat kidney fibrosis. Described herein are methods of treating or preventing kidney fibrosis via the administration of the antibodies and antigen-binding fragments described herein. The humanized antibodies and antigen-binding fragments described herein can also be used in medicaments for the treatment of kidney fibrosis.

The humanized antibodies and antigen-binding fragments which bind PAI-1 and are described herein can be used to treat cardiac fibrosis. Described herein are methods of treating or preventing cardiac fibrosis via the administration of the antibodies and antigen-binding fragments described herein. The humanized antibodies and antigen-binding fragments described herein can also be used in medicaments for the treatment of cardiac fibrosis.

The humanized antibodies and antigen-binding fragments which bind PAI-1 and are described herein can be used to treat endometriosis. Described herein are methods of treating or preventing endometriosis via the administration of the antibodies and antigen-binding fragments described herein. The humanized antibodies and antigen-binding fragments described herein can also be used in medicaments for the treatment of endometriosis.

Compounds of the present invention can be, as needed, administered in combination with one or more therapeutic treatments. One would understand that the listing of therapeutic regimens listed below represents conventional therapies, but the present invention encompasses other known therapeutic regimens which are not specifically disclosed herein.

In one embodiment, the one or more therapeutic wound healing treatments administered in conjunction with antibodies and antigen-binding fragments described herein include, but are not limited to, diketopiperazine based compounds, tetramic acid based compounds, hydroxyquinolinone based compounds, Enalapril®, Eprosartan, Troglitazone, Vitamin C, Vitamin E, Mifepristone (RU486), and Spironolactone, or any combination thereof.

In one embodiment, the one or more therapeutic HCV treatments administered in conjunction with antibodies and antigen-binding fragments described herein. Compounds of the present invention can be, as needed, administered in combination with one or more therapeutic treatments including, but not limited to, Interferon alpha (IFN-α), Ribavirin, or a combination thereof.

In one embodiment, the one or more therapeutic HBV treatments administered in conjunction with antibodies and antigen-binding fragments described herein. Compounds of the present invention can be, as needed, administered in combination with one or more therapeutic treatments including, but not limited to, Lamivudine (a nucleoside analog), IFN-α or a combination thereof.

In one embodiment, the one or more therapeutic endometriosis treatments administered in conjunction with antibodies and antigen-binding fragments described herein. Compounds of the present invention can be, as needed, administered in combination with one or more therapeutic treatments including, but not limited to, total hysterectomy (removal of uterus and cervix), supracervical hysterectomy (removal of uterus and preservation of the cervix), and bilateral Salpingo-Oophorectomy (removal of the fallopian tubes and ovaries).

In one embodiment, the one or more therapeutic cirrhosis treatments administered in conjunction with antibodies and antigen-binding fragments described herein. Compounds of the present invention can be, as needed, administered in combination with one or more therapeutic treatments including, but not limited to, alcohol detoxification, albumin, pegylated IFNα2b with Ribavirin, or a combination thereof.

In one embodiment, the one or more therapeutic post-transplantation treatments administered in conjunction with antibodies and antigen-binding fragments described herein include, but are not limited to, administration of immunosuppressive drugs to prevent immune reactions to a transplanted organ and to also suppress the formation of fibrosis (mediated by immune cell damage).

Compounds of the present invention can be, as needed, administered in combination with one or more therapeutic treatments including, but not limited to, kidney transplant immunosuppressive drugs such as, for example, Cyclosporin A, Tacrolimus (PROGRAF®), Azathioprine (IMURAN®), Mycophenolate mophetil (CELLCEPT®), Prednisone/steroids, Sirolimus/Rapamycin (RAPAMUNE®), or any combination thereof.

Compounds of the present invention can be, as needed, administered in combination with one or more therapeutic treatments including, but not limited to, liver transplant immunosuppressive drugs such as, for example, Azathioprine (IMURAN®), Mycophenolate mophetil (CELLCEPT®), Cyclosporine (SANDIMMUNE®, NEORAL®), Daclizumamab/Basiliximab (anti-IL-2 receptor-alpha), or any combination thereof.

Multiple Sclerosis

Multiple sclerosis (MS) is characterized by inflammation, focal demyelination and axonal degeneration, preceded by disturbances in the blood-brain barrier (BBB), with entry of serum proteins, including fibrin(ogen), into the central nervous system (CNS). Fibrin is deposited in the axons in MS and in chronic experimental allergic encephalomyelitis (EAE), and up-regulation of components of the components of the plasminogen activator (fibrinolytic) system correlates with onset of inflammation and migration of leukocytes into the brain parenchyma. Influx of fibrin(ogen) is associated with up-regulated activity of tPA. In MS, tPA activation is matched by a significant increase in PAI-1, preventing the efficient clearance of fibrin. In EAE, an animal model of MS, mice deficient in tPA suffer an early onset and more severe form of disease that is associated with high levels of PAI-1 and inefficient fibrin removal. Similar findings have been observed in a peripheral nerve injury model in which fibrin hindered axonal regeneration and contributed to demyelination and axonal degeneration. In acute EAE, perivascular fibrin deposits have been shown to correlate with the occurrence of paralytic clinical signs; rats treated with ancrod, a defibrinogenating agent, showed a marked reduction in fibrin deposits and exhibited no paralytic signs. PAI-1 was further shown to play a role in regulating cell motility of leukocytes through interaction with uPA and its receptor (uPAR). Interaction of uPAR with uPA, PAI-1, low-density lipoprotein-receptor-related protein (LRP), vitronectin and integrins provides a mechanism for cell chemotaxix, adhesion and migration (East et al. Neuropathology and Applied Neurobiology, 34(2): 216-30 (2008)).

The humanized antibodies and antigen-binding fragments which bind PAI-1 and are described herein can be used to treat multiple sclerosis. Described herein are methods of treating or preventing multiple sclerosis via the administration of the antibodies and antigen-binding fragments described herein. The humanized antibodies and antigen-binding fragments described herein can also be used in medicaments for the treatment of multiple sclerosis.

Compounds of the present invention can be, as needed, administered in combination with one or more therapeutic treatments. In one embodiment, the one or more therapeutic treatments include, but are not limited to, ENBRIL®, or other conventional medicinal therapeutic regimens.

Arthritis

Arthritis compromises the quality of life for large numbers of people. For example, more than 5 million people suffer from rheumatoid arthritis (RA) worldwide, of which 2.5 million are in the United States. About 50,000-70,000 children in the United States have been diagnosed with juvenile RA, and psoriatic arthritis affects in the range of 2.5 to 5 million people in the United States alone.

Rheumatoid arthritis (RA) is a systemic chronic autoimmune disease characterized by synovial hyperplasia and inflammatory cell recruitment, intra-articular fibrin deposition, and, in its later stages, cartilage and bone destruction. It is well documented that the degradation of the extracellular matrix (ECM) in bone and cartilage that takes place during the development of RA is dependent on the action of a variety of proteolytic enzymes secreted by both soft and hard tissue cellular elements, as well as by inflammatory cells. Many different proteases are believed to contribute to matrix destruction during RA, although the exact mechanisms responsible for this process and how it is regulated are poorly understood. However, indirect evidence indicates that both matrix metalloproteinases (MMPs) and plasminogen activators (PAs) may play a fundamental role in the pathophysiology of rheumatic disease.

The plasminogen-activation system is a versatile, temporally controlled enzymatic system in which plasminogen is activated to the proteolytic enzyme plasmin by either of the two physiological plasminogen—activators, tissue-type plasminogen activator (tPA) and urokinase-type plasminogen activator (uPA). uPA is involved in tissue remodeling during wound healing, inflammatory cellular migration, neo-vascularization and tumor cell invasion, while tPA, a key enzyme in thrombosis, is involved in the dissolution of clots in blood vessels and the maintenance of hemostasis in the vasculature. Activation of the plasminogen-activation system is initiated by the release of tPA or uPA by specific cells in response to external signals and leads to a locally expressed extracellular proteolytic activity (Vassalli et al., J. Exp. Med. 1977; 146: 857-868; Saksela & Rifkin, Annu. Rev. Cell Biol. 1988; 4: 93-126). The PA-system is also regulated by specific inhibitors directed against PAs and plasmin, including PA-inhibitor type 1 (PAI-1), PA-inhibitor type 2 (PAI-2), protease nexin 1 (PN-1) and a 2-anti-plasmin (Saksela & Rifkin, Annu. Rev. Cell Biol. 1988; 4:93-126; Ny et al., Thromb. Res. 1993; 71: 1-45). All of these inhibitors, which belong to the serpin family, are suicide inhibitors that are cleaved by cognate protease (Wilczynska et al., Nature Struct. Biol. 1997; 4: 354-357). One feature of the PA-plasmin system is the amplification achieved by the conversion of plasminogen to plasmin. Because of the high concentration of plasminogen in virtually all tissues, the production of relatively small amounts of PA can result in high local concentrations of plasmin.

Accumulation of intra-articular fibrin, resulting from the altered balance between coagulation and fibrinolysis, is a common feature of RA and it is possible that these fibrin deposits can have adverse effects (Weinberg et al., Ann. Rheum. Dis. 1991; 56:550-557; Jasini, In: Immunopathogenesis of Rheumatoid Arthritis. G. S. Panayi and P. M. Johnson (Eds.), Red Books, Surrey. 137-146 (1991)). In this context, degradation of fibrin matrix, which is mainly performed by plasmin, could be beneficial. The possibility that plasmin may, in fact, play a beneficial role in intra-articular fibrin removal has only recently been discussed (Busso et al., J. Clin. Invest, 102: 41-50 (1998)).

Antigen-induced arthritis in mice serves as a model for human rheumatoid arthritis. In a PAI-1 murine knockout model in which mice did not express PAI-1 and in which arthritis was induced, it was observed that mice had significantly decreased synovial accumulation of fibrin in arthritic joints, the synovial tissue content of D-dimers (the specific fibrin degradation products generated by plasmin) were increased and PA activity was increased in synovial tissues. As a result, fibrin accumulation in arthritic joints and the severity of antigen-induced arthritis (AIA) were reduced (Ness et al. Rheumatology, 41: 136-141 (2002)).

The humanized antibodies and antigen-binding fragments which bind PAI-1 and are described herein can be used to treat arthritic conditions such as, for example, rheumatoid arthritis and osteoarthritis. Described herein are methods of treating or preventing arthritic conditions via the administration of the antibodies and antigen-binding fragments described herein. The humanized antibodies and antigen-binding fragments described herein can also be used in medicaments for the treatment of arthritic conditions.

Compounds of the present invention can be, as needed, administered in combination with one or more therapeutic treatments. In one embodiment, the one or more therapeutic treatments include, but are not limited to, anti-inflammatory agents (e.g., NSAIDS and steroids), joint replacement, or any other conventional medicinal therapies.

Liver Disease

The humanized antibodies and antigen-binding fragments which bind PAI-1 and are described herein can be used to treat liver fibrosis. Described herein are methods of treating or preventing liver fibrosis via the administration of the antibodies and antigen-binding fragments described herein. The humanized antibodies and antigen-binding fragments described herein can also be used in medicaments for the treatment of liver fibrosis. Various liver fibrosis models are available for assessment of the effect of anti-PAI-1 on disease indications: Ferru et al. Scand. J. Immunol. 48: 233-240 (1998); Safadi et al. Gastroenterology 127: 870-882 (2004); Novobrantseva et al. J. Clin. Invest. 115: 3072-3082 (2005); Chiaramonte et al. J. Clin. Invest. 104: 777-785 (1999); Shi et al. PNAS USA 94: 10663-10668 (1997).

Alcoholic liver disease is the major cause of liver disease in Western countries; in Asian countries, viral hepatitis is the major cause.

Fatty change and alcoholic hepatitis are typically reversible. The later stages of fibrosis and cirrhosis tend to be irreversible but can usually be well managed for long periods of time. Fatty change (steatosis) is the accumulation of fat in liver cells which can be seen as fatty globules under the microscope. Alcoholism causes large fatty globules (macrovesicular steatosis). Other causes of macrovesicular steatosis include diabetes, obesity and starvation. Some people get an acute alcoholic hepatitis or inflammatory reaction to the cells affected by fatty change; this is called alcoholic steatonecrosis and the inflammation typically predisposes a subject to liver fibrosis.

Cirrhosis is a late stage of liver disease marked by fibrosis and altered liver architecture. It is often progressive and may, in some cases, eventually lead to liver failure. Late complications of cirrhosis or liver failure include portal hypertension, coagulation disorders, ascites and other complications including hepatic encephalopathy and the hepatorenal syndrome.

Cirrhosis is typically characterized by replacement of liver tissue by fibrous scar tissue as well as regenerative nodules (lumps that occur as a result of a process in which damaged tissue is regenerated), leading to progressive loss of liver function. Cirrhosis is most commonly caused by alcoholism, hepatitis B and C and fatty liver disease but has many other possible causes. Some cases are cryptogenic, i.e., of unknown cause.

Ascites (fluid retention in the abdominal cavity) is the most common complication of cirrhosis and is associated with a poor quality of life, increased risk of infection, and a poor long-term outcome. Other potentially life-threatening complications are hepatic encephalopathy (confusion and coma) and bleeding from esophageal varices. Cirrhosis is generally irreversible once it occurs, and treatment generally focuses on preventing progression and complications. In advanced stages of cirrhosis, the only current treatment option is a liver transplant.

Alcoholic liver disease (ALD) ranks among the major causes of morbidity and mortality in the world, and affects millions of patients worldwide each year. Progression of the disease is well characterized and is actually a spectrum of liver diseases, which ranges initially from simple steatosis, to inflammation and necrosis (steatohepatitis), to fibrosis and cirrhosis. Although the progression of ALD is well characterized, there is no current universally-accepted therapy available to halt or reverse this process in humans.

Liver cirrhosis is a worldwide health problem. It is the irreversible end result of fibrous scarring, and is characterized by diffused disorganization of the normal liver structure of regenerative nodules and fibrotic tissue (Lee, M.Y., Hepatitis B virus infection N. Engl. J. Med, 24, 1733-1745, 1997). It has become one of the leading causes of death by disease.

Hepatic cirrhosis is a disease resulting from hepatic chronic damage. Damage might be toxic (chronic ingestion of alcohol), infectious (viral hepatitis, mainly by hepatitis B and/or C virus), immunological, (primary biliary cirrhosis), by biliary obstruction, (secondary biliary cirrhosis), or metabolic (Wilson's disease). All forms of cirrhosis have characteristics in common: synthesis and excessive deposition of proteins of extracellular matrix (ECM), mainly collagen I and to a lesser extent collagens IV and II), and consequently the formation of nodules of hepatocytes, abnormal vascularization and portal hypertension. These physiopathological processes lead to an alteration in the blood supply and in consequence in the nutrition of hepatic cells. Regardless of the etiological agent and morphologic differences, all forms of cirrhosis have as a common end, hepatic failure causing the patient's death.

Incidence of cirrhosis is growing as a result of the widespread occurrence of chronic hepatitis and the obvious lack of an established therapy for hepatic fibrosis. It is estimated that 350 million people worldwide have chronic HBV infection (Xu et al., (2003) Cur. Gene Ther. 3, 341-356; Ueki et al., (1999) Nature Med., 5, 226-230). In Southeast Asia, Africa and China, more than 50% of the population is infected, and 8% to 15% have become chronically infected. Chronic HBV infection is the cause of up to 50% of cirrhosis cases in these regions (Xu et al., Id.; Ueki et al., Id). The resulting distortion of the liver architecture compromises the function of hepatocytes, causing systemic life-threatening complications.

Cirrhosis still remains untreatable by conventional therapy. Recent progress in vector development has heralded a possible treatment (Lee, Id; Rudolph et al., Science 287:1253-1258, 2000). However, the oncogenic potential of therapeutic genes, such as hepatic growth factor (HGF) (Ueki et al., Id) and telomerase genes (Rudolf et al., Id), might prevent their use in humans.

Cirrhosis has many possible causes; sometimes more than one cause is present in the same patient. In the Western World, chronic alcoholism and hepatitis C are the most common causes.

Alcoholic liver disease (ALD). Alcoholic cirrhosis develops in 15% of individuals who drink heavily for more than a decade. There is great variability in the amount of alcohol needed to cause cirrhosis (as little as 3-4 drinks a day in some men and 2-3 in some women). Alcohol seems to injure the liver by blocking the normal metabolism of protein, fats, and carbohydrates. Patients may also have concurrent alcoholic hepatitis with fever, hepatomegaly, jaundice, and anorexia. AST and ALT are both elevated but less than 300 IU/L with a AST:ALT ratio>2.0, a value rarely seen in other liver diseases. Liver biopsy may show hepatocyte necrosis, Mallory bodies, neutrophilic infiltration with perivenular inflammation.

Chronic hepatitis C. Infection with this virus causes inflammation of and low grade damage to the liver that over several decades can lead to cirrhosis. Chronic hepatitis C may be diagnosed with serologic assays (e.g., the enzyme immunoassay, EIA-2) that detect hepatitis C antibody or viral RNA.

Chronic hepatitis B. The hepatitis B virus is probably the most common cause of cirrhosis worldwide, especially South-East Asia, but it is less common in the United States and the Western world. Hepatitis B causes liver inflammation and injury that over several decades can lead to cirrhosis. Hepatitis D is dependent on the presence of hepatitis B, but accelerates cirrhosis in co-infection. Chronic hepatitis B can be diagnosed with detection of HBsAG>6 months after initial infection.

Non-alcoholic steatohepatitis (NASH). In NASH, fat builds up in the liver and eventually causes scar tissue. This type of hepatitis appears to be associated with diabetes, protein malnutrition, obesity, coronary artery disease, and treatment with corticosteroid medications. This disorder is similar to that of alcoholic liver disease but a patient may not have an alcohol history.

Primary biliary cirrhosis. A patient may be asymptomatic or complain of fatigue, pruritus, and non-jaundice skin hyperpigmentation with hepatomegaly. There is prominent alkaline phosphatase elevation as well as elevations in cholesterol and bilirubin. Diagnosis is made using antimitochondrial antibodies with liver biopsy as confirmation if showing florid bile duct lesions; it is more common in women.

Primary sclerosing cholangitis. PSC is a progressive cholestatic disorder presenting with pruritus, steatorrhea, fat soluble vitamin deficiencies, and metabolic bone disease. There is a strong association with inflammatory bowel disease (IBD), especially ulcerative colitis. Diagnosis is best with contrast cholangiography showing diffuse, multifocal strictures and focal dilation of bile ducts, leading to a beaded appearance. Non-specific serum immunoglobulins may also be elevated.

Autoimmune hepatitis. This disease is caused by the immunologic damage to the liver causing inflammation and eventually scarring and cirrhosis. Findings include elevations in serum globulins, especially gamma globulins. Therapy with prednisone+/−azathioprine is beneficial. Cirrhosis due to autoimmune hepatitis still has 10-year survival of 90%+.

Hereditary hemochromatosis usually presents with family history of cirrhosis, skin hyperpigmentation, diabetes mellitus, pseudogout, and/or cardiomyopathy, all due to signs of iron overload. For diagnosis, laboratories generally show fasting transferrin saturation of >60% and ferritin>300 ng/mL. Genetic testing may be used to identify HFE mutations. Current treatment is with phlebotomy to lower total body iron levels.

Wilson's disease is an autosomal recessive disorder characterized by low serum ceruloplasmin and increased hepatic copper content on liver biopsy. A patient may also have Kayser-Fleischer rings in the cornea and present with an altered mental status.

One or more of the following are generally found in patients diagnosed with cirrhosis:

Aminotransferases—AST and ALT are moderately elevated, with AST>ALT. However, normal aminotransferases do not preclude cirrhosis.

Alkaline phosphatase (AP)—usually slightly elevated.

GGT—correlates with AP levels. Typically much higher in chronic liver disease from alcohol.

Bilirubin—may elevate as cirrhosis progresses.

Albumin—levels fall as the synthetic function of the liver declines with worsening cirrhosis since albumin is exclusively synthesized in the liver Prothrombin time—increases since the liver synthesizes clotting factors.

Globulins—increased due to shunting of bacterial antigens away from the liver to lymphoid tissue.

Serum sodium—hyponatremia due to inability to excrete free water resulting from high levels of ADH and aldosterone.

Thrombocytopenia—due to both congestive splenomegaly as well as decreased thrombopoietin from the liver. However, this rarely results in platelet count<50,000/mL.

Leukopenia and neutropenia—due to splenomegaly with splenic margination.

Coagulation defects—the liver produces most of the coagulation factors and thus coagulopathy correlates with worsening liver disease.

Chronic inflammation represents one hallmark of the progression of ALD. A key concept in the hepatic inflammatory response during ALD is priming and sensitization. Specifically, inflammatory cells are affected by alcohol so that they respond more robustly to an inflammatory insult (i.e., "primed"). Furthermore, target cells respond more robustly to products produced by inflammatory cells (i.e., "sensitized"). Inflammatory cytokines (e.g., TNFα) have roles in both priming and sensitization in experimental ALD. For example, macrophages from alcohol exposed animals produce more TNFα after stimulus and TNFα is more cytotoxic to hepatocytes from alcohol-exposed animals. However, the potential roles of other aspects of the inflammatory response in ALD have been less studied.

The early stages of alcoholic liver disease (ALD) involve chronic inflammation. Whereas mechanisms of by which this effect is mediated are not completely understood, enhanced sensitivity to circulating lipopolysaccharide may contribute to this process. It has recently been shown that ethanol induces activation of plasminogen activator inhibitor-1 (PAI-1). PAI-1 causes fibrin accumulation in liver by inhibiting degradation of fibrin (fibrinolysis). LPS also enhances fibrin accumulation by activating the coagulation cascade. Ethanol may, therefore, increase fibrin accumulation caused by LPS, enhancing liver damage.

PAI-1 has been postulated to mediate inflammatory effects in vivo. Experiments with PAI-1−/− mice exposed to chronic enteral ethanol showed that, in addition to blunting steatosis, genetic inhibition of PAI-1 expression also conferred profound anti-inflammatory effects. Indeed, whereas knocking out PAI-1 partially blunted the steatotic changes caused by ethanol, there was almost complete protection against the inflammatory changes caused by alcohol in this strain. A similar anti-inflammatory effect of knocking-out PAI-1 has been observed in a mouse model of glomerulonephritis. Whereas PAI-1, the main inhibitor of fibrinolysis, is well known to be induced during inflammation, how PAI-1 may actually contribute to inflammatory processes is less understood. One mechanism by which PAI-1 may contribute to inflammation is via its classic role of impairing fibrinolysis.

The humanized antibodies and antigen-binding fragments which bind PAI-1 and are described herein can be used to treat ALD. Described herein are methods of treating or preventing ALD via the administration of the antibodies and antigen-binding fragments described herein. The humanized antibodies and antigen-binding fragments described herein can also be used in medicaments for the treatment of ALD.

In one embodiment, treatment of a subject with the humanized anti-PAI-1 antibodies described herein may result in decreased AST and/or ALT levels, decreased levels of alkaline phosphatase (AP), decreased GGT and/or AP levels, decreased bilirubin, decreased prothrombin time, decreased globulins, reduction in thrombocytopenia, decreased hyponatremia, decreased leukopenia and neutropenia, reduction in coagulation defects, or a combination thereof. Reduction or decrease in levels of compounds or symptoms may be by 5%, 10%, 15%, 20%, 30%, 40%, 50%, 60%, 70%, 80%, 90%, 95%, 100%, or any integer therein, compared to levels observed prior to treatment. Reduction or decrease may also be by 1.5 fold, 5 fold, 10 fold, 15 fold, 20 fold, 30 fold, 40 fold, 50 fold, 60 fold, 70 fold, 80 fold, 90 fold, 95 fold, 100 fold, or any integer therein, compared to levels observed prior to treatment.

In addition to the embodiments described above, or alternatively, treatment of a subject with the humanized anti-PAI-1 antibodies described herein may result in increased albumin. Increase in levels of albumin may be by 5%, 10%, 15%, 20%, 30%, 40%, 50%, 60%, 70%, 80%, 90%, 95%, 100%, or any integer therein, compared to levels observed prior to treatment. Increase in levels of albumin may also be by 1.5 fold, 5 fold, 10 fold, 15 fold, 20 fold, 30 fold, 40 fold, 50 fold, 60 fold, 70 fold, 80 fold, 90 fold, 95 fold, 100 fold, or any integer therein, compared to levels observed prior to treatment.

Treatment also encompasses any improvement in symptoms or general health of the subject being treated.

The severity of cirrhosis is generally classified with the Child-Pugh score. This score uses bilirubin, albumin, INR, presence and severity of ascites and encephalopathy to classify patients in class A, B or C; class A has a favorable prognosis, while class C is at high risk of death. More scores, used in the allocation of liver transplants but also in other contexts, are the Model for End-Stage Liver Disease (MELD) score and its pediatric counterpart, the Pediatric End-Stage Liver Disease (PELD) score. The hepatic venous pressure gradient, i.e., the difference in venous pressure between afferent and efferent blood to the liver, also determines severity of cirrhosis, although hard to measure. A value of 16 mm or more means a greatly increased risk of dying. Treatment also encompasses any improvement in symptoms or general health of the subject being treated.

Treatment may, in some cases, also include other forms of treatment in combination therapy. For example, a subject may be co-administered a humanized anti-PAI-1 antibody described herein in combination with alcohol abstinence, diet modification (e.g., salt modification), diuretics, laxatives, antibiotics, antiviral drugs, chelation therapy (e.g., penicillamine), anti-hypertension drugs, liver transplantation, enemas, thiamine, steroids, or a combination thereof.

Chronic Kidney Disease, Diabetic Nephropathy, Macular Degeneration and Diabetes-Associated Conditions Accumulation of the glomerular mesangial extracellular matrix (ECM) leading to glomerulosclerosis is a common finding in diabetic nephropathy and other chronic kidney diseases. Several lines of evidence indicate that ECM accumulation in such chronic renal diseases results from both increased synthesis and degreased degradation of ECM components and it is widely accepted that ECM degradation in glomeruli and glomerular cells is mediated by a plasminogen activator-plasmin-matrix metalloproteinase-2 (MMP)-2 cascade. In addition, a variety of studies have reported decreased plasminogen activator (PA) activity, decreased plasmin activity, or increased levels of PA inhibitor 1 (PAI-1; the major PA inhibitor), in glomeruli obtained from animals with experimentally induced glomerular injuries known to result in mesangial matrix accumulation (Baricos, et al., "Extracellular Matrix Degradation by Cultured Mesangial Cells: Mediators and Modulators" (2003) Exp. Biol. Med. 228:1018-1022).

PAI-1 is a protein associated with extracellular matrix. Macular degeneration (AMD) is the loss of photoreceptors in the portion of the central retina, termed the macula, responsible for high-acuity vision. Degeneration of the macula is associated with abnormal deposition of extracellular matrix components and other debris in the membrane between the retinal pigment epithelium and the vascular choroid. This debris-like material is termed drusen. Drusen is observed with a funduscopic eye examination. Normal eyes may have maculas free of drusen, yet drusen may be abundant in the retinal periphery. The presence of soft drusen in the macula, in the absence of any loss of macular vision, is considered an early stage of AMD.

Choroidal neovascularization (CNV) commonly occurs in macular degenerasin in addition to other ocular disorders and is associated with proliferation of choroidal endothelial cells, overproduction of extracellular matrix, and formation of a fibrovascular subretinal membrane. Retinal pigment epithelium cell proliferation and production of angiogenic factors appears to effect choroidal neovascularization.

Diabetic retinopathy (DR) is an ocular disorder that develops in diabetes due to thickening of capillary basement membranes and lack of contact between pericytes and endothelial cells of the capillaries. Loss of pericytes increases leakage of the capillaries and leads to breakdown of the blood-retina barrier.

Proliferative vitreoretinopathy is associated with cellular proliferation of cellular and fibrotic membranes within the vitreous membranes and on the surfaces of the retina. Retinal pigment epithelium cell proliferation and migration is common with this ocular disorder. The membranes associated with proliferative vitreoretinopathy contain extracellular matrix components such as collagen types I, II, and IV and fibronectin, and become progressively fibrotic.

The humanized antibodies and antigen-binding fragments which bind PAI-1 and are described herein can be used to treat or prevent diabetic nephropathy. Described herein are methods of treating or preventing diabetic nephropathy via the administration of the antibodies and antigen-binding fragments described herein. The humanized antibodies and antigen-binding fragments described herein can also be used in medicaments for the treatment of diabetic nephropathy.

The humanized antibodies and antigen-binding fragments which bind PAI-1 and are described herein can be used to treat or prevent macular degeneration, CNV or proliferative vitreoretinopathy. Described herein are methods of treating or preventing macular degeneration, CNV or proliferative vitreoretinopathy via the administration of the antibodies and antigen-binding fragments described herein. The humanized antibodies and antigen-binding fragments described herein can also be used in medicaments for the treatment of macular degeneration, CNV or proliferative vitreoretinopathy.

Compounds of the present invention can be, as needed, administered in combination with one or more standard therapeutic treatments known in the art. For example, for treatment of diabetic nephropathy, compounds of the present invention can be administered in combination with, for example, ACE inhibitors, angiotensin II receptor blockers (ARBS) or any other conventional therapy such as, for example, glucose management.

Obesity is reaching epidemic proportions worldwide. More than half of the adults in the U.S. are overweight or obese. Obesity is a strong risk factor for the development of insulin resistance and type 2 diabetes. Type 2 diabetes affects ~17 million adults in the U.S. with increased morbidity and mortality due to increased micro- and macrovascular complications. Aggressive intervention in the early course of the disease can decrease many of the above consequences. Importantly, the prevalence of obesity-related disorders emphasizes the need for concerted efforts to prevent obesity rather than just treatment of its associated diseases.

Increased PAI-1 has been linked to not only thrombosis and fibrosis but also insulin resistance. Circulating PAI-1 levels in humans are increased in obesity and the insulin resistance syndrome, and these increased levels correlate strongly with the degree of insulinemia. Adipose tissue produces and secretes a large number of hormones, cytokines, and proteins that affect glucose homeostasis and insulin sensitivity, including tumor necrosis factor-α, PAI-1, leptin, peroxisome proliferator-activated receptor (PPAR)-γ, resistin and adiponectin. PAI-1 is over-expressed in adipose tissue of obese mice and humans, and adipose tissue itself can directly contribute to the elevated PAI-1 levels. Additionally, studies on PAI-1 genetic knock-out mice show increased protection against the development of diabetes. Thus, the elevated PAI-1 associated with obesity is believed to be a contributor to obesity and progression to diabetes as well as a consequence of obesity (Li-Jun Ma, et al., Prevention of Obesity and Insulin Resistance in Mice Lacking Plasminogen Activator Inhibitor 1 (February 2004) Diabetes, Vol. 53, pp. 336-346).

The humanized antibodies and antigen-binding fragments which bind PAI-1 and are described herein can be used to treat or prevent obesity. Provided herein are methods of treating or preventing obesity via the administration of the antibodies and antigen-binding fragments described herein. Also provided herein are methods of treating or preventing insulin resistance syndrome via the administration of the antibodies and antigen-binding fragments described herein. The humanized antibodies and antigen-binding fragments described herein can also be used in medicaments for the treatment of obesity and insulin resistance syndrome.

Compounds of the present invention can be, as needed, administered in combination with one or more therapeutic treatments such as, for example, insulin or any other conventional therapy. One would understand that the listing of therapeutic regimens represents conventional therapies, but the present invention encompasses other known therapeutic regimens which are not specifically disclosed herein. In one embodiment, the one or more therapeutic treatments include, but are not limited to, diet modification, weight loss, exercise, gastric bypass surgery, insulin treatment, or any combination thereof.

Alzheimer's Disease

Plasmin and tPA are known to be involved in the degradation and/or clearance of beta-amyloid plaques which are the hallmarks of Alzheimer's disease. Activated tPA, in turn, activates plasminogen which is known to degrade beta-amyloid plaques. (Wang et al., *Beta-Amyloid Degradation and Alzheimer's Disease*, J. Biomedicine and Biotech., 2006: 1-12 (2006)). Additionally, PAI-1 has also been shown to be upregulated in Alzheimer's affected brain tissue. (Tucker et al., *Tissue Plasminogen Activator Requires Plasminogen to Modulate Amyloid-beta Neurotoxicity and Deposition*, J. Neurochem. 75: 2172-2177 (2000)). Alzheimer's disease is known to be an inheritable disease, thus more common in families with a history of the disease, but it may occur in any segment of the population. Clinical symptoms of Alzheimer's disease and its progression are well known, and thus identification of a patient population for which treatment is warranted is easily accomplished.

The humanized antibodies and antigen-binding fragments which bind PAI-1 described herein can be used to treat Alzheimer's disease by reducing the amount of PAI-1 in the serum. The humanized antibodies and antigen-binding fragments which bind PAI-1 and are further modified to cross the blood-brain barrier as described herein can also be used to treat or prevent Alzheimer's disease. The humanized antibodies and antigen-binding fragments further modified to cross the blood-brain barrier as described herein can also be used in medicaments for the treatment of Alzheimer's disease.

Compounds of the present invention can be, as needed, administered in combination with one or more therapeutic treatments. One would understand that the listing of therapeutic regimens listed below represents conventional therapies, but the present invention encompasses other known therapeutic regimens which are not specifically disclosed herein. In one embodiment, the one or more therapeutic treatments include, but are not limited to, a radiation with gold particles attached to beta amyloid fibrils.

Cardiovascular Diseases

The cardiovascular disease that can be treated or prevented in accordance with the invention is not limited to any particular disorder. Exemplary diseases in this regard include but are not limited to ischemic heart disease, arteriosclerosis, atherosclerosis, hypertension, angina, heart attack, stroke, deep vein thrombosis, disseminated intravascular coagulation, premature myocardial infarction, and coronary artery disease. Risk factors associated with cardiovascular disease are well known, and thus afford the clinician a means by which to identify that patient population for which prevention of cardiovascular disease is warranted. Such risk factors include, but are not limited to, obesity, diabetes, high blood pressure, stress, lowered estrogen levels, chronic inflammation, and combinations thereof. Subjects who present with more than one risk factor may be that much more susceptible to developing cardiovascular disease, and are appropriate subjects for the preventative treatment as provided by the invention.

The humanized antibodies and antigen-binding fragments which bind PAI-1 and are described herein can be used to treat or prevent cardiovascular disease. Described herein are methods of treating or preventing cardiovascular disease via the administration of the antibodies and antigen-binding fragments described herein. The humanized antibodies and antigen-binding fragments described herein can also be used in medicaments for the treatment of cardiovascular disease. In one embodiment, the antibodies or antigen-binding fragments described herein are administered to treat ischemic heart disease. In another embodiment, the antibodies or antigen-binding fragments described herein are administered to treat arteriosclerosis. In yet another embodiment, the antibodies or antigen-binding fragments described herein are administered to treat atherosclerosis. Further embodiments include methods of treating hypertension, angina, heart attack, stroke, deep vein thrombosis, disseminated intravascular coagulation, premature myocardial infarction, peripheral artery disease (PAD or PAOD) and coronary artery disease by administering the antibodies or antigen-binding fragments described herein.

Compounds of the present invention can be, as needed, administered in combination with one or more therapeutic treatments. One would understand that the listing of therapeutic regimens listed below represents conventional therapies, but the present invention encompasses other known therapeutic regimens which are not specifically disclosed herein. In one embodiment, the one or more therapeutic treatments include, but are not limited to, angiotensin-converting enzyme (ACE) inhibitors (e.g., Ramipril), angiotensin receptor blockers, beta-blockers, aspirin, exercise, anti-platelet agents (CLOPIDOGREL®), Cilostazol, or any combination thereof.

Respiratory Diseases

Respiratory diseases believed to implicate PAI-1 include acute respiratory distress syndrome (ARDS), idiopathic pulmonary fibrosis (IPF), asthma and chronic obstructive pulmonary disease (COPD).

ARDS is believed to result from alterations in alveolar fibrinoloysis precipitated by localized insult and inflammation. IPF is defined as a type of chronic fibrosing interstitial pneumonia of unknown cause and limited to the lungs. Both diseases, while manifesting differently in the lungs, are characterized by increased levels of PAI-1 in the diseased tissue as well as increased fibrosis. (Ware et al., *Coagulation and fibrinolysis in human acute lung injury—New therapeutic targets?*, Keio J. Med. 54(3): 142-149 (2005); Thomas Geiser, *Idiopathic pulmonary fibrosis—a disorder of alveolar wound repair*, Swiss Med. Wkly. 133: 405-411 (2003)). The identification of this factor comprises one of many known clinical indicia of disease, all of which afford clinicians a means to identify subjects in need of treatment for ARDS and/or IPF. The humanized antibodies and antigen-binding fragments which bind PAI-1 and are described herein can be used to treat or prevent ARDS and/or IPF. Described herein are methods of treating or preventing ARDS and/or IPF via the administration of the antibodies and antigen-binding fragments described herein. The humanized antibodies and antigen-binding fragments described herein can also be used in medicaments for the treatment of ARDS and/or IPF.

The mechanisms responsible for the development of asthma in atopic patients include genetic predisposition and the effects of environmental exposures to inflammatory stimuli in the airways of susceptible individuals (Bleecker, E. R., and D. A. Meyers in Genetics of Allergy and Asthma. M. N. Blumenthal, and B. Bjorksten, (eds. Marcel Dekker, New York, p. 307 1997). Asthma represents a chronic inflammatory process of the airways. The consequences of chronic inflammation in the asthmatic airways include increased numbers of fibroblasts and the deposition of extracellular matrix (ECM) such as collagen, fibronectin, and laminin within the airway wall (Altraja, A., et al. Am. J. Respir. Cell. Mol. Biol. 15: 482, 1996; Roche, W. R., et al. Lancet. 1:520, 1989). The plasminogen activator (PA) system has an important role in controlling endogenous fibrosis and regulating ECM proteolysis relevant to tissue remodeling (Gabazza, E. C., et al. Lung. 177: 253, 1999). The tissue-type PA (tPA) and urokinase-type PA (uPA) converts plasminogen to plasmin, which enhances proteolytic degradation of the ECM. An important mechanism in the regulation of PA activity is inhibition of uPA or tPA by three major inhibitors, which are PAI-1, PAI-2, and PAI-3 (Kruitoff, E. K. Enzyme 40: 113, 1988). Among these three inhibitors, PAI-1 is the most important in controlling lung fibrosis (Geiger, M., et al, Immunopharmacology 32: 53, 1996; Lardot, C., et al. Eur. Respir. J. 11: 912, 1988; Kruitoff E. K., et al. J. Biol. Chem. 261: 11207, 1986). PAI-1 overexpressing mice suffered severe lung injury and deposition of ECM after bleomycin challenge (Eitzman, D. T., et al. J. Clin. Invest. 97: 232, 1996) or hyperoxia (Barazzone, C., et al. J. Clin. Invest. 98: 2666, 1996), whereas PAI-1 deficient mice were protected against such a fibrotic reaction. These findings show that PAI-1 is closely associated with fibrosis and ECM accumulation after lung injury or inflammation. Recently, the induction of PAI-1 was demonstrated in mast cells of the asthmatic airway (Cho, S. H., et al. J. Immunol. 165: 3154-3161, 2000).

Described herein are methods of treating or preventing asthma or chronic obstructive pulmonary disease (COPD) via the administration of the antibodies and antigen-binding fragments described herein. The humanized antibodies and antigen-binding fragments described herein can also be used in medicaments for the treatment of asthma and/or chronic obstructive pulmonary disease (COPD).

Compounds of the present invention can be, as needed, administered in combination with one or more therapeutic treatments. One would understand that the listing of therapeutic regimens listed below represents conventional therapies, but the present invention encompasses other known therapeutic regimens which are not specifically disclosed herein. In one embodiment, the one or more therapeutic treatments include, but are not limited to, budesonide, prednisone, bleomycin, a beta adrenergic compound, or any combination thereof.

Cancer

PAI-1 is believed to be involved in both the prevention of degradation of tumor tissue as well as the stimulation of angiogenesis in tumor tissue. PAI-1 protein is often expressed by cancer cells in non-invasive areas, suggesting that this inhibitor plays a role in protecting the tumor tissue against the proteolytic degradation.

Exemplary tumors with high levels of PAI-1 and low or unfavorable prognosis include breast cancers as well as colon adenocarcinomas. PAI-1 mRNA is known to be expressed by endothelial cells in the tumor stroma of colon adenocarcinomas as well as breast cancer, while there is no PAI-1 expression in the surrounding normal tissue, suggesting that PAI-1 plays a role in protecting the tumor tissue against degradation. Another role of PAI-1 is to participate in the process of tumor angiogenesis. PAI-1 and uPA interactions are known to be involved in angiogenesis, PAI-1 has been found in angiogenic, growing tumors (Noel et al., *Membrane associated proteases and their inhibitors in tumor angiogenesis*, J. Clin. Pathol. 57: 577-584 (2004)). Thus, the inhibition of PAI-1 represents a treatment option for cancerous tumors. The humanized antibodies and antigen-binding fragments which bind PAI-1 and are described herein can be used to treat cancerous tumors. The humanized antibodies and antigen-binding fragments described herein can also be used in medicaments for the treatment cancerous tumors.

A tumor or cancer to be treated in the methods described herein includes, but is not limited to, a lung cancer, a gynecologic malignancy, a melanoma, a breast cancer, a pancreatic cancer, an ovarian cancer, a uterine cancer, a colon cancer, a prostate cancer, a kidney cancer, a head cancer, a pancreatic cancer, a uterine cancer, a neck cancer or a renal cell cancer. In one embodiment, a tumor to be treated is a primary tumor. In another embodiment, a tumor to be treated is a metastatic tumor. In one embodiment, a tumor or cancer to be treated is of epithelial origin.

In accordance with the invention, the humanized PAI-1 antibodies or fragments thereof can be administered alone or in combination with active or inactive agents. When combinations are used, the invention contemplates simultaneous or sequential administration of the humanized PAI-1 antibodies or antigen-binding fragments and the active or inactive agents.

Compounds of the present invention can be, as needed, administered in combination with one or more therapeutic treatments. One would understand that the listing of therapeutic regimens listed below represents conventional therapies, but the present invention encompasses other known therapeutic regimens which are not specifically disclosed herein.

A review of methods for conducting three-dimensional in vitro tissue culture models of breast cancer are described by Kim et al., Breast Cancer Research Treatment 85(3): 281-91 (2004). Other in vivo and in vitro models for testing cancers are known and can be used to test anti-PAI-1 antibodies described herein.

In one embodiment, the cancer is prostate cancer and the one or more therapeutic treatments is surgery, radiotherapy (e.g., external beam or braquitherapy), hormonal deprivation (androgen suppression), heat shock protein 90 (HSP90) inhibitors, chemotherapy (e.g., doxcetaxel, platinum-based chemotherapy such as platin, carboplatin, satraplatin and oxaliplatin, taxane, estramustin), prednisone or prednisolone, cholesterol-lowering drugs such as statins, leutinizing hormone-releasing hormone (LHRH) agonists, RNAi therapy, whole tumor cells genetically modified to secrete granulocyte macrophage—colony stimulating factor (GM-CSF) (also known as GVAX), or any combination thereof.

In one embodiment, the cancer is ovarian cancer and the one or more therapeutic treatments is surgery, chemotherapy (e.g., doxorubicin, gemcitabine, Rubitecan, and platinum-based chemotherapeutics such as cisplatin, carboplatin and oxaliplatin), melphalan, paclitaxel, topoisomerase I inhibitors such as topotecan and irinotecan, taxane-based therapy, hormones, radiation therapy, whole body hypothermia, isoflavone derivatives such as Phenoxodial, cytotoxic macrolides such as Epothilones, angiogenesis inhibitors such as bevacizumab, signal transduction inhibitors such as trastuzumab, gene therapy, RNAi therapy, immunotherapy, monoclonal antibodies, phosphatidylinositol-like kinase inhibitors such as rapamycin, or any combination thereof.

In one embodiment, the cancer is lung cancer and the one or more therapeutic treatments is surgery, radiotherapy (e.g., thoracic radiotherapy, radiation therapy with charged particles, Uracil-tegafur and Platinum-based chemotherapy (e.g., cisplatin, carboplatin, oxaliplatin, etc.) and vinorebline, Erlotinib (Tarceva), Gefitinib (Iressa), anti-epidermal growth factor receptor antibodies (e.g., Cetuximab), anti-vascular endothelial growth factor antibodies (e.g., Bevacizumab), small molecule inhibitors of tyrosine kinases, direct inhibitors of proteins involved in lung cancer cell proliferation, Aurora kinase inhibitors, laser-induced thermotherapy, RNAi therapy, whole tumor cells genetically modified to secrete granulocyte macrophage—colony stimulating factor (GM-CSF) (also known as GVAX), or any combination thereof.

In one embodiment, the cancer is breast cancer and the one or more therapeutic treatments is surgery, monoclonal antibodies (e.g., Her-2 antibodies, herceptin), hypoxic cells, adjuvant chemotherapy such as single agent chemotherapy or combination chemotherapy (e.g., anthracycline- and taxane-based polychemotherapies or target-specific trastuzumab with or without endocrine manipulation with or without PMRT, virorelbine), selective estrogen receptor modulators such as Tamoxifen and Raloxifene, allosteric estrogen receptor modulators such as Trilostane, radiation (e.g., interstitial brachytherapy, Mammosite device, 3-dimensional conformal external radiation and intraoperative radiotherapy), Aromatase inhibitors that suppress total body synthesis (e.g., anastrozole, exemestane and letrozole), RNAi therapy, intravenous analogs of rapamycin that are immunosuppressive and anti-proliferative such as Temsirolimus (CCI779), or any combination thereof.

In one embodiment, the cancer is colon cancer and the one or more therapeutic treatments is surgery, radiation therapy, and chemotherapy (e.g., 5-fluorouracil, levamisole, leucovorin or semustine (methyl CCNU)), N-[2-(dimethylamino)ethyl]acridine-4-carboxamide and other related carboxamide anticancer drugs; non-topoisomerase II inhibitors, liposomal topotecan, taxane class of anticancer agents (e.g., paclitaxel or docetaxel), a compound of the xanthenone acetic acid class (e.g., 5,6-dimethylanthenone-4-acetic acid PMAA), laminarin, site-selective cyclic AMP Analogs (e.g., 8-chloroadenosine 3',5'-cyclic phosphate), pyranoindole inhibitors of Cox-2, carbazole inhibitors of Cox-2, tetrahydrocarbazole inhibitors of Cox-2, indene inhibitors of Cox-2, localized inhibitors of NSAIDS (e.g., anthranilic acids, aspirin (5-acetylsalicylic acid), azodisal sodium, carboheterocyclic acids, carprofen, chlorambucil, diclophenac, fenbufen, fenclofenac, fenoprofen, flufenamic acid, flurbiprofen, fluprofen, furosemide, gold sodium thiomalate, ibuprofen, indomethacin, indoprofen, ketoprofen, lonazolac, loxoprofen, meclofenamic acid, mefanamic acid, melphalan, naproxen, penicillamin, phenylacetic acids, proprionic acids, salicylic acids, salazosulfapyridine, sulindac, tolmetin, a pyrazolone butazone propazone NSAID, meloxicam, oxicams, piroxicam, feldene, piroxicam beta cyclodextran, tenoxicam, etodolac, and oxaprozin), an inhibitor of HER-2/neu, RNAi therapy, GM-CSF, monoclonal antibodies (e.g., anti-Her-2/neu antibodies, anti-CEA antibodies, A33 (HB 8779), 100-210 (HB 11764) and 100-310 (HB 11028)), hormonal therapy, pyrimidineamines, camptothecin derivatives (e.g., CPT-11), folinic acid (FA), Gemcitabine, Ara-C, platinum-based chemotherapeutics such as cisplatin, carboplatin and oxaliplatin, a cGMP-specific phosphodiesterase inhibitor, or any combination thereof.

In one embodiment, the cancer is pancreatic cancer and the one or more therapeutic treatments is surgery, radiation therapy (RT), Fluorouracil (5-FU) and RT, systemic therapy, stenting, Gemcitabine (GEMZAR®), Gemcitabine and RT, Cetuximab, erlotinib (TARCEVA®), chemoradiation, bevacizumab (AVASTIN®), or any combination thereof.

IV. Packages and Kits

In still further embodiments, the present application concerns kits for use with the compounds described above. Humanized antibodies or antigen-binding fragments that bind PAI-1 can be provided in a kit. The kits will thus comprise, in suitable container means, a composition comprising an antibody or antigen-binding fragment thereof that binds PAI-1. The kit may comprise an antibody or antigen-binding fragment thereof that binds PAI-1 in suitable container means.

The container means of the kits will generally include at least one vial, test tube, flask, bottle, syringe and/or other container means, into which the at least one polypeptide can be placed, and/or preferably, suitably aliquoted. The kits can include a means for containing at least one fusion protein, detectable moiety, reporter molecule, and/or any other reagent containers in close confinement for commercial sale. Such containers may include injection and/or blow-molded plastic containers into which the desired vials are retained. Kits can also include printed material for use of the materials in the kit.

Packages and kits can additionally include a buffering agent, a preservative and/or a stabilizing agent in a pharmaceutical formulation. Each component of the kit can be enclosed within an individual container and all of the various containers can be within a single package. Invention kits can be designed for cold storage or room temperature storage.

Additionally, the preparations can contain stabilizers to increase the shelf-life of the kits and include, for example, bovine serum albumin (BSA). Where the compositions are lyophilized, the kit can contain further preparations of solutions to reconstitute the lyophilized preparations. Acceptable reconstitution solutions are well known in the art and include, for example, pharmaceutically acceptable phosphate buffered saline (PBS).

Additionally, the packages or kits provided herein can further include any of the other moieties provided herein such as, for example, one or more reporter molecules and/or one or more detectable moieties/agents.

Packages and kits can further include one or more components for an assay, such as, for example, an ELISA assay. Samples to be tested in this application include, for example, blood, plasma, and tissue sections and secretions, urine, lymph, and products thereof. Packages and kits can further include one or more components for collection of a sample (e.g., a syringe, a cup, a swab, etc.).

Packages and kits can further include a label specifying, for example, a product description, mode of administration and/or indication of treatment. Packages provided herein can include any of the compositions as described herein. The package can further include a label for treating a diabetic nephropathy, obesity, or cardiovascular disease.

The term "packaging material" refers to a physical structure housing the components of the kit. The packaging material can maintain the components sterilely and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method of the invention. A kit can include a compound in a pack, or dispenser together with instructions for administering the compound in a method described herein.

Instructions can include instructions for practicing any of the methods described herein including treatment methods. Instructions can additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, IC tip and hybrids of these such as magnetic/optical storage media.

The embodiments of the compounds and methods of the present application are intended to be illustrative and not limiting. Modifications and variations can be made by persons skilled in the art in light of the above teachings specifically those that may pertain to alterations in the antibodies or antigen-binding fragments which bind PAI-1 surrounding the described modifications while maintaining near native functionally with respect to binding, inhibition, or neutralization of PAI-1. Therefore, it should be understood that changes may be made in the particular embodiments disclosed which are within the scope of what is described.

EXAMPLES

The application may be better understood by reference to the following non-limiting examples, which are provided as exemplary embodiments of the application. The following examples are presented in order to more fully illustrate embodiments of the invention and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the invention; it should be understood that various alternatives to the embodiments described herein may be employed in practicing the methods described herein.

Example 1

The functional properties of the antibodies and antigen-binding fragments thereof can be determined by assessing their ability to inhibit active PAI-1 utilizing a PAI-1 neutralization assay.

PAI-1 activity is determined using a plasminogen coupled chromogenic method. Briefly, 25 µL PAI-1 (50 ng mL-1 active PAI-1) is incubated in the wells of a 96-well microtiter plate with an equal volume of either TBS buffer (0.05 M Tris.HCl, 0.01 M NaCl pH 7.4 containing 0.01% Tween 80) or with serial 2-fold dilutions of antibody or antigen-binding fragment thereof, resulting in a molar excess (antibody:PAI-1) between 1 and 128. The mixture is allowed to react for 2 h at room temperature. Subsequently, 50 µL of tPA (20 IU mL-1 or 40 ng mL-1) is added and the plate is incubated for 15 min at 37° C. Then, 100 µL of a solution containing plasminogen (1 µM), CNBr-digested fibrinogen (1 µM) and S-2403 (0.6 mM) is added. The absorbance change at 405 nm is recorded to measure the residual tPA activity. One hundred percent PAI-1 activity is defined as the PAI-1 activity observed in the absence of antibody (or fragment). The percentage inhibition (i.e. neutralization of PAI-1 activity) by the antibody (or fragment) is calculated from the residual PAI-1 activity measured in the presence of the antibody (or fragment).

Example 2

The effects of antibodies or antigen-binding fragments thereof described herein on the rate of PAI-1 inactivation can be determined using conventional techniques. For example, the half-life of PAI-1 in the presence of antibody or antigen-binding fragment thereof can be calculated.

PAI-1 (40 µg mL$^{-1}$ in PBS) is incubated with a 3-fold molar excess of antibody or antigen-binding fragment thereof at 37° C. At various time intervals, an aliquot is removed and incubated with a 2-fold molar excess of tPA (25 min at 37° C.). The reaction products are analyzed by SDS-PAGE followed by silver staining. Quantification of the reaction products is performed by subsequent densitometric scanning (e.g., Lab-scan® and Image-Master®). Based on the amount of active PAI-1 at each time point, the half-life of PAI-1 in the presence of antibody or antigen-binding fragment thereof can be calculated.

Example 3

Effects of the antibodies or antigen-binding fragments thereof described herein on the reaction products generated during interaction of PAI-1 with tPA can be assessed using conventional techniques.

Briefly, PAI-1 (40 µg mL-1 in PBS) is incubated for 10 min at 37 CC either in the absence (control) or in the presence of an 8-fold molar excess of antibody or antigen-binding fragment. Samples are then incubated with a 2-fold molar excess of tPA (25 min at 37° C.). The reaction is terminated by adding SDS (final concentration of 1%) and heating for 30 s at 100° C. The reaction products are analyzed by SDS-PAGE followed by staining with Coomassie brilliant blue. Quantification of the reaction products is performed by subsequent densitometric scanning.

Example 4

Affinity of antibodies and antigen-binding fragments thereof described herein for PAI-1 can be assessed using conventional techniques such as, for example, surface plasmon resonance (SPR; Biacore).

Affinity constants for the binding of the various antibodies and antigen-binding fragments to PAI-1 are determined by SPR using, for example, a BIAcore™ 3000 analytical system equipped with a CM5 sensor chip (BIAcore AB). The antibodies or antigen-binding fragments are covalently coupled to the CM5 sensorchip up to 1500 resonance units (using a concentration of 10 µmL$^{-1}$ in 10M acetate buffer and pH appropriate for the specific antibody or antigen-binding fragment tested). PAI-1 is injected (40 µL) at concentrations between 5 and 250 nM at a flow rate of 30 µL min$^{-1}$. Ten microliters of a 10-mM HCl solution is used to regenerate the chip after each cycle. Association and dissociation rate constants are calculated with the software of the BIAcore™ 3000 (Langmuir binding model).

Example 5

This example describes an in vivo method to test the effect of antibodies and antigen-binding fragments thereof described herein on the treatment of glomerular nephritis.

White New Zealand rabbits are separated into different treatment groups with multiple animals placed in each treatment group. Glomerular nephritis is induced by the intravenous administration of horse anti-rabbit glomerular basement membrane (GBM) followed by the administration of rabbit anti-horse antibody. Rabbit test groups are then administered dosages of the anti-PAI antibody or antigen binding fragment at time points as pre-determined in multiple dosing regimens established for the 14 day trial period. Efficacy of treatment is assessed by determination of proteinuria via ELISA or HPLC throughout the 14 day treatment period. Animals are sacrificed throughout the treatment period to examine kidneys and glomeruli for evidence of morphological changes, glomerular nephritis and extra-cellular matrix deposition via light and electron microscopy and immunohistochemical staining. Efficacy of the anti-PAI-1 antibodies and antigen-binding fragments described herein for the treatment of diabetic nephropathy can be tested via this rabbit model of glomerular nephritis.

Example 6

This example describes an in vivo method to test the effect of antibodies and antigen-binding fragments thereof described herein on thrombolysis.

New Zealand White rabbits are exposed to one of four preparatory regimens: rabbits in group I are fed a regular diet for 8 months; rabbits in group II are fed a diet of 1% cholesterol for 2 months alternated with 2 months of a regular diet for a total of 8 months; rabbits in group III undergo balloon-induced arterial wall injury, followed by a regular diet for 8 months; and rabbits in group IV undergo balloon-induced arterial wall injury, followed by a diet of 1% cholesterol for 2 months, then followed by a regular diet for 2 months for a total of 4 months. Following arterial wall injury, Rabbits are assigned treatment groups and administered concentrations of antibody or antigen-binding fragment in varying frequency as pre-determined in multiple dosing regimens established for the testing period. Rabbits are sacrificed throughout the treatment period and arterial walls are excised and examined for thrombus formation, PAI-1 concentration, and tPA/uPA concentrations in the injured arterial tissue. PAI-1 and tPA/uPA is identified by PCR from the excised tissue or by immunohistochemical staining. Thrombus formation is assessed by immunohistological and microscopy techniques to identify and establish an effective dose and dosing schedule for the stimulation of thrombolysis.

Example 7

Expression of a Humanized 33B8 PAI-1 Antibody pcDNA3.1(+) Constructs.

Two dsDNA sequences containing codons for the humanized 33B8 VH (H1) and VL (κ1) regions (corresponding to SEQ ID NOS: 17 and 3, respectively) were synthesized at Blue Heron. These synthesized sequences also contain nucleotides necessary to add or conserve restriction endonuclease sites at the 5' and 3' ends as indicated. All codons in upper case have been optimized for expression in Chinese Hamster Ovary (CHO) cells. Signal peptide (underlined) and constant region sequences used to complete the heavy and light chains were derived from cDNAs purchased from Open Biosystems. Coding region sequences of all constructs were confirmed by DNA sequencing. The protein products are designated CT140 (for IgG4) and CT110 (for IgG1).

Heavy Chain Construct Nucleic Acid and Amino Acid Sequences, Respectively

H1 Codopt (SEQ ID NO: 102)
atatataagcttgccaccatggacTGGACTTGGCGCATCCTCTTTTTGGT

GGCCGCCGCTACTGGAGCTCATTCTCAGGTCCAGCTTGTCCAGTCTGGAG

CTGAAGTGAAAAAACCTGGAGCTTCTGTGAAAGTATCTTGTAAGGCAAGC

GGATATACTTTCACAAACTACGGCATGAATTGGGTTCGCCAGGCCCCTGG

CCAGGGACTGGAGTGGATGGGATGGATTAATACTTACACCGGAGAGCCTA

CCTACACCGATGACTTTAAGGGTCGTTTTACAATGACCCTCGACACAAGC

ATTTCCACTGCCTACATGGAGCTGTCCCGACTCAGAAGCGATGACACCGC

CGTATACTACTGTGCTAAGGATGTTTCTGGATTCGTGTTCGATTACTGGG

GCCAGGGTACACTGGTGACCGTATCTAGCGCCTCAACCAAAGGCCCATCT

GTTTTCCCCTTGGCCCCTAGCTCCAAGTCTACATCCGGGGGCACAGCAGC

TCTGGGCTGTCTTGTGAAGGATTACTTTCCAgaaccggtgactgtg (SEQ ID NO: 103)
MDWTWRILFLVAAATGAHSQVQLVQSGAEVKKPGASVKVSCKASGYTFTN

YGMNWVRQAPGQGLEWMGWINTYTGEPTYTDDFKGRFTMTLDTSISTAYM

ELSRLRSDDTAVYYCAKDVSGFVFDYWGQGTLVTVSSASTKGPSVFPLAP

SSKSTSGGTAALGCLVKDYFPEPVTV

Restriction endonuclease sites are as follows: (SEQ ID NOS 104-105, respectively in order of appearance)

```
5"      HindIII                                    AgeI        3"
        |      Kozak consensus                     |
        ATA TAT AAG CTT gcc acc atg gAC    //    GAA CCG CTG
                                  M  D  W           E   P   V
```

H1 contains a signal peptide (underlined) sequence from an IgG1 (GenBank Accession No. BC111019, GenBank Accession No. AAH80557). H1 contains part of the CH1 region from BC07249.

Figure 5:
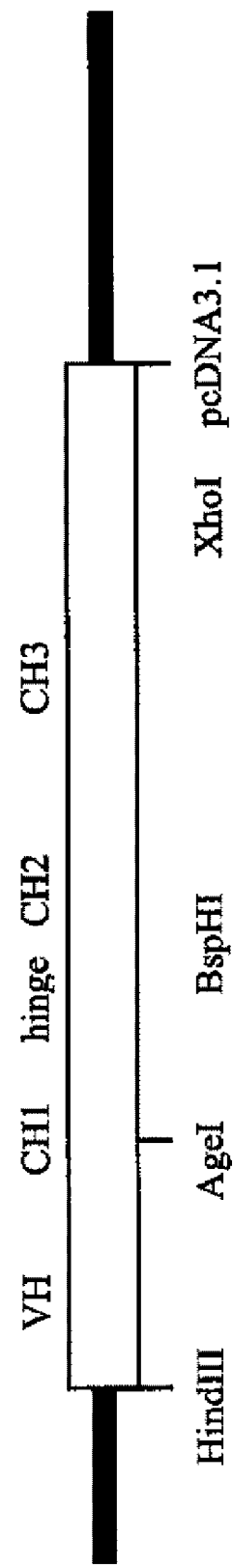
FIG. 5 Illustrates a 3-way ligation: H1 was ligated to the CH1, hinge, CH2 and CH3 of an IgG4 (GenBank Accession No. BC111019, GenBank Accession No. AAI11020) at a conserved AgeI restriction site. The HindIII and XhoI sites were ligated to the corresponding sites in pcDNA3.1 (+).

In a 3-way ligation, H1 was ligated to the CH1, hinge, CH2 and CH3 of an IgG1 (GenBank Accession No. BC072419, GenBank Accession No. AAH72419) coding region at a conserved Age I restriction site. The 5' HindIII and 3' XhoI sites were ligated to the corresponding sites in pcDNA3.1 (Invitrogen, Carlsbad, Calif.). Similarly, in a 3-way ligation, H1 was ligated to the $CH_1$, hinge, CH2 and CH3 of an IgG4 (GenBank Accession No. BC111019, GenBank Accession No. AAI21020) (See FIG. 5).

Kappa Chain Construct Nucleic Acid and Amino Acid Sequences, Respectively
K1 Codopt (SEQ ID NO: 106)
ctatatataagcttgccaccATGAGGTTGCCAGCTCAGGTCCTCGGTCTG

GTGATGCTCTGGGTAAGCGGCAGCAGCGGTGACATCGTGATGACCCAGTC

CCCTGATAGTTTGGCTGTGAGTCTCGGCGAGCGGGCCACAATTAATTGTA

AGAGCAGTCAAAGTCTGTTGAATATCATTAAGCAGAAAAATTGTCTTGCC

TGGTATCAACAAAAGCCTGGCCAGCCACCTAAGCTGCTGATATACTGGGC

TAGTACTCGTGAATCCGGTGTGCCCGATCGGTTTTCCGGAAGCGGTTCCG

GGACTGACTTCACTCTGACAATTTCTAGCCTGCAGGCCGAGGACGTTGCC

GTTTACTACTGCCAGCAGTATTACAGTTACCCCTACACATTCGGACAGGG

AACCAAACTGGAAATCAAACGCAGTGTCGCCGCTccatctgtcttcatct tc

-continued (SEQ ID NO: 107)
MRLPAQLLGLLMLWVSGSSGDIVMTQSPDSLAVSLGERATINCKSSQSLL

NIIKQKNCLAWYQQKPGQPPKLLIYWASTRESGVPDRLFSGSGSGTDFTL

TISSLQAEDVAVYYCQQYYSYPYTFGQGTKLEIKRTVAAPSVFIF

Restriction endonuclease sites are as follows: (SEQ ID NOS 108-110, respectively in order of appearance)

```
5"    HindIII                           <BbsI    3"
      |    Kozak consensus              |
      ATA TAT AAG CTT gcc acc atg  //  CCA TCT GTC TTC
                        M  R  L   //   P   S   V   F
```

K1 contains a signal peptide (underlined) sequence from a kappa light chain (GenBank Accession No. BC093097).

Figure 6:
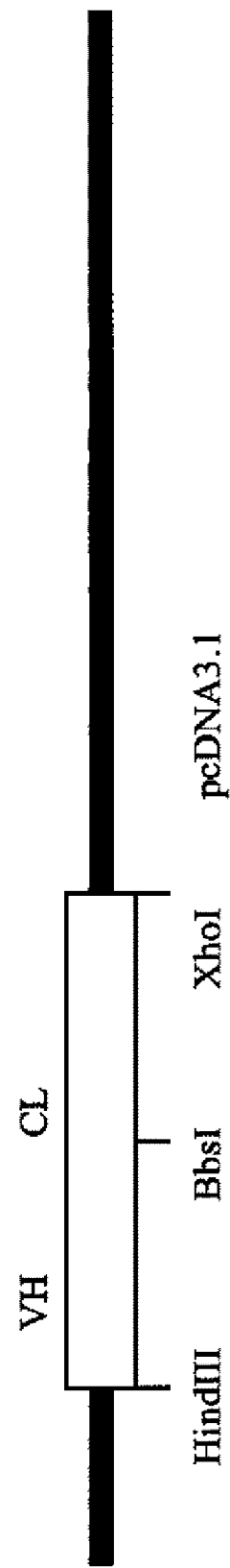
FIG. 6 Illustrates a 3-way ligation: κ1 was ligated to the CL of a Kappa (κ) light chain (GenBank Accession No. BC093097) coding region at a conserved BbsI restriction site.

In a 3-way ligation, K1 was ligated to the CL of a Kappa (κ) light chain (GenBank Accession No. BC093097) coding region at a conserved BbsI restriction site. The 5' HindIII site and 3' XhoI site were ligated into the corresponding sites in pcDNA3.1 (+) (See FIG. 6).

pVITRO1 Constructs

The heavy and light chain coding regions from pcDNA3.1 constructs described above were subcloned into a bicistronic expression vector, pVITRO1 (Invitrogen, Carlsbad, Calif.). Primers were designed to generate coding regions with terminal restriction sites to facilitate insertion into the multiple cloning sites (MCS) of pVITRO1. In addition 8-base pair restriction sites were added to facilitate generation of future constructs. The Kappa chain was ligated into the BamHI and BspEI sites in MCS1. The IgG1 heavy chain was ligated into the BglII and NheI sites of MCS2.

It has been well established that IgG4 can be expressed as a "half-antibody;" that is, one heavy chain and one light chain. To stabilize IgG4, its hinge region was replaced with that of IgG1. Thus in a 3-way ligation (into pVITRO MCS2; FIG. 7), a BglII to BspHI fragment of IgG1 containing the VH, CH1 and hinge region was ligated to a BspHI to NheI fragment of IgG4 containing the IgG4 Fc region.

Primers used for PCR and transfer of Ig sequences from pcDNA3.1 to pVITRO are as follows:

```
Sense primer for IgG1 and IgG4:
      BglII    PacI
5' ATAT AGATCT TTAATTAA TGCCACCATGGACTGGAC         (SEQ ID NO: 111)

Antisense primer for IgG4:
      NheI     FseI     *
5' ATAT GCTAGC GGCCGGCC TCATCATTTACCCAGAGACAGG     (SEQ ID NO: 112)

Antisense primer for IgG1:
      NheI     FseI     *
5' ATAT GCTAGC GGCCGGCC TCATCATTTACCCGGAGACAGG     (SEQ ID NO: 113)

Antisense primer for Kappa:
      BamHI
5' ATAT GGATCC GCG GCC GCC TAC TAA CAC TCT CCC CTG TTG   (SEQ ID NO: 114)

Sense primer for Kappa:
      BspEI
5' ATAT TCCGGA ATT TAA ATT CCC ACC ATG AGG TTG CCA G    (SEQ ID NO: 115)
```

Example 8

Humanized antibodies were engineered from parental murine monoclonal antibody 33B8 which exhibit high PAI-1 affinity and neutralizing activity. The antibodies were expressed in mammalian cells and tested for activity in in vitro systems. Transient and stable expression vector constructs for both IgG1 (CT110; amino acid sequence provided in FIG. 8A) and IgG4 (CT140; amino acid sequence provided in FIG. 8B) were generated. To stabilize IgG4, the hinge was replaced with that of IgG1 (Angal, King et al. 1993).

Several bioanalytical assays are utilized to support selection of the final drug candidate and initial pharmacokinetic assessment. These include a PAI-1 ELISA (P-ELISA) consisting of n-terminal biotin-labeled PAI-1 immobilized to strepavidin coated microtiter wells (see protocol below).

CT140 binding was detected with HRP conjugated anti-human antibody. The current sensitivity of the assay is 10-20 ng/ml.

ELISA Protocol Using Neutravidin™ Coated Plates

All reagents are brought to room temperature (18-23° C.) and dilutions are made in Wash Buffer (1×TBS, 0.1% BSA, 0.05% Tween). Briefly, protocol steps are as follows:

Add 100 μL of Neutravidin™ Pierce#31000 (0.5 μg/ml in TBS) to 96-well Immulon-4 plates. Incubate 1 hour at room temperature (RT).
Wash wells 3 times with 200 μl Wash Buffer.
Add 50 μL of biotinylated biomolecule (0.06 nM) Incubate 1 hour at RT.
Wash plate 3 times in Wash Buffer.
Add 100 μL of 1° Ab Incubate 30 min RT
Wash plate 3 times in Wash Buffer.
Add 50 μL of 2° Ab-HRP (1:10,000) Incubate 30 min RT
Wash plate 4 times in Wash Buffer.
Add 100 μl TMB Reagent (substrate). Incubate at room temperature.
Add 100 μL of 2 M Sulfuric Acid to stop development of the substrate.
Plates were read using a 450 m filter with a 615-620 nm filter as the reference.

CT140 specifically bound human and murine PAI-1 to a greater extent than the murine parental antibody (mP1) and the control antibody (FIG. 12).

Example 9

PAI-1 Neutralization

An established PAI-1 activity assay was tested which measures PAI-1 inhibition of uPA cleavage of a chromogenic substrate as described by Gorlatova, Cale et al. 2007). This assay can be used to determine efficiency of PAI-1 neutralization by CT140.

Neutralization Assay Protocol

All reagents are brought to room temperature (18-23° C.) and the plate reader is pre-warmed to 37° C. All dilutions are conducted in Assay Buffer (0.15 M NaCl, 0.05 M Tris (pH 7.5), 0.01% Tween, 100 μg/ml BSA).

Final Conditions
Duplicate Wells
100 μl
1.5 U uPA/well
8 nM wt active human PAI-1 (Molecular Innovations# PAI-A) 25 μl chromogenic substrate (Centerchem# Pefachrome uPA 8294)
0-80 μg/ml CT140.

Assay steps are as follows: fifty (50) μl of dilutions of CT140 are placed into 96 wells (Falcon 30720); add 25 μl of uPA (1.5 U), 3 seconds (s) shaking on plate reader; incubate 5 minutes at 37° C.; add 25 μl chromogenic substrate to develop the plates. Plates are shaken for 3 s and read every 5 minutes (min) up to 30 min on a plate reader with a 405 nm filter at 37° C. Percentage (%) activity was calculated from mean V.

CT140 was found to neutralize uPA to an extent similar the murine monoclonal antibody 33B8 (FIG. 11).

Example 10

CT110/CT140 Affinity for Different Species of PAI-1

Binding of CT140 to rat, mouse, rabbit and human PAI-1 was determined by P-ELISA (see FIG. 12). The relative affinity of CT140 is human=rabbit>mouse>rat (FIG. 12A, FIG. 12B, FIG. 12C and FIG. 12D, respectively). Preliminary assessment by ELISA yielded an approximate 2 to 4-fold greater affinity for human PAI-1 relative to the parental mouse antibody (data not shown). The affinity for human and rabbit PAI-1 appears to be 4 to 5 times greater relative to mouse monoclonal antibody 33B8 (mP-1).

The humanized antibody was found to bind to mouse PAI-1. The relative affinity of CT140 for mouse PAI-1 is approximately the same as that of the mouse parent antibody binding to rabbit PAI-1. Since the parent antibody has demonstrated efficacy in a rabbit disease model, CT140 can be expected to demonstrate efficacy in a mouse disease model. The changes made proximal to CDRs during the process of humanization, appears to result in a higher affinity for human PAI-1 and significant reactivity to mouse and rat PAI-1. CT140 affinity for mouse PAI-1 appears to be over 10-fold greater relative to the parent mouse anti-PAI-1.

Example 11

This experiment was conducted to measure the binding constants for hP-1 (humanized mAb CT140) and mP-1 (mouse antibody 33B8).

hP-1 was captured onto an anti-human IgG surface (Cat-tag goat mAb) at 5 different surface densities. hP-1 and mP-1 were diluted to a starting concentration of 100 nM and tested in a 3-fold dilution series using PBS with 0.005% Tween-20 and 0.1 mg/ml BSA. Binding data were collected at 25° C. The association phase was monitored for 5 minutes and the dissociation phase was monitored for 2.5 hours. The response data for each antigen over the 5 different density mAb surfaces were globally fit to a simple 1:1 interaction model. A fit to the data was determined (data not shown) a binding constants were determined at 25° C. A summary of the binding constants is provided in the following table.

|  | $k_a$ (M$^{-1}$s$^{-1}$) | $K_d$ (s$^{-1}$) | $K_D$ |
| --- | --- | --- | --- |
| hP-1 | 5.30(1)e5 | 8(1)e-6 | 15(2) pM |
| mP-1 | 3.93(2)e5 | 0.00314(3) | 8.01(9) nM |

Example 12

CT140 Neutralization of PAI-1

The ability of CT140 to neutralize PAI-1 inhibition of uPA protease activity was determined (FIG. 11). The data indicates that the neutralizing activity of CT140 is equivalent to the parental antibody. A human antibody control did not neutralize PAI-1 activity. The neutralizing activity of CT140 and variants is compared in a minimum of three assays.

Example 13

Detection of PAI-1 Antibodies in Plasma

A P-ELISA may be used to monitor plasma levels of CT140 in PK and efficacy studies. The P-ELISA was able to detect a PAI-1 antibody in spiked plasma samples (closed circle "●") compared to control IgG (line; —), antibody in the absence of plasma (closed diamond; "♦"), or antibody+ EDTA (closed square "■") as illustrated in FIG. 13. The effect of variables that effect detection of CT140 in plasma samples by the P-ELISA can be determined. This includes sample processing and storage conditions.

Example 14

In Vivo Liver Fibrosis Assessment

A liver fibrosis experiment was conducted to determine the effect of CT140 treatment on fibrosis in mouse disease model. Liver fibrosis was induced in mice by bile duct ligation.

A. Immunohistology

Materials and Methods

Mice were housed in a pathogen-free barrier facility accredited by the Association for Assessment and Accreditation of Laboratory Animal Care and procedures were approved by the local Institutional Animal Care and Use Committee. Eight week old male C57BL/6J mice were obtained from Jackson Laboratory (Bar Harbor, Me.). Food and tap water were allowed ad libitum. Sham-operated mice underwent a laparotomy with exposure but not ligation of the common bile duct. A second group of mice underwent bile duct ligation (BDL). BDL was performed by surgical ligation of the common hepatic bile duct under isoflurane anesthesia according to methods described by Bergheim et al. (J. Pharmacol. Exp. Ther. 316: 592-600 (2006)). A third group of animals underwent BDL, were injected with PAI-1 antibody solution (or saline vehicle) intraperitoneally 7, 10, 13 and 16 days after BDL and were sacrificed 18 days after BDL.

Mice were anesthetized by injection of a ketamine HCL/xylazine solution (100/15 mg/kg intramuscularly (i.m.); Sigma-Aldrich, St. Louis, Mo.). Blood was collected from the vena cava just prior to sacrifice by exsanguination and citrated plasma was stored at −80° C. for further analysis. Portions of liver tissue were frozen immediately in liquid nitrogen, while others were fixed in 10% neutral buffered formalin for subsequent sectioning and mounting on microscope slides.

Formalin fixed, paraffin embedded liver sections were cut at 5 μm and mounted on glass slides. Sections were deparaffinized and stained with hematoxylin-eosin (H+E). Pathologic changes were assessed in blinded manner. Neutrophil accumulation in the livers was assessed by staining tissue sections for chloracetate esterase (CAE), a specific marker for neutrophils, using the napthol AS-D chloracetate esterase kit (Sigma, St. Louis Mo.) using methods described by Gujral et al. (Am. J. Physiol. Gastrointest. Liver Physiol. 286: G499-G507 (2004)) and Guo et al. (Hepatology 40: 583-589 (2004)).

Extracellular matrix accumulation in liver sections was determined by staining with Sirius red-fast green (Lopez-De Leon and Rojkind, (1985) J. Histochem. Cytochem 33: 737-743). Sirius red staining was quantitated by image-analysis as described previously (Bergheim et al. J. Pharmacol. Exp. Ther. 316: 592-600 (2006)).

Results: Treatment with CT140 Protects Mice from Liver Fibrosis

Representative photomicrographs depicting hematoxylin and eosin (H+E; 100×), chloroacetate esterase (CAE; 200×) and Sirius red (100×) stains were examined. The pathology of tissues looked markedly different between placebo and CT140 treated mice (data not shown). The H+E stain shows some morphological differences. Briefly, the CT140 treated group morphology parallels the sham laparotomy group morphology. The CAE stain shows that there are fewer neutrophils (pink in the stain) in the CT140-treated Ab group compared to BDL control animals, and the CT140 group CAE staining parallels the sham laparotomy group CAE staining. Bile duct ligation caused a robust increase in the incidence of bile pools with necroinflammatory foci in livers of PBS-treated BDL mice; furthermore, large areas of more basophilic cells can be seen and which are likely areas of fibrosis. Whereas, the incidence of bile pools was not blunted in antibody treated mice, they appeared to contain fewer infiltrating inflammatory cells than PBS-treated BDL mice. The amount of basophilic cells in the microscope field in antibody treated mice was less than in PBS-treated BDL mice.

FIG. 14 illustrates the effect of PAI-1 neutralizing antibody on Sirius red staining after bile duct ligation in mice. Image-analysis is reported as fold of sham-operated control animals. The Sirius red staining shows that there is greatly reduced collagen in the group treated with CT140 compared to and BDL control animals, and the CT140 group Siruis red staining parallels the sham laparotomy group Siruis red staining.

B. Effect of PAI-1 Neutralizing Antibody on the Expression of Key Genes of Liver Fibrosis Materials and Methods: RNA Isolation and Real-Time RT-PCR Total RNA was extracted from liver tissue samples by a guanidium thiocyanate-based method (RNA STAT 60 Tel-Test, Ambion, Austin, Tex.). RNA concentrations were determined spectrophotometrically, and 1 μg total RNA was reverse transcribed using an AMV reverse transcriptase kit (Promega, Madison, Wis.) and random primers. Polymerase chain reaction (PCR) primers and probes were designed using Primer 3 (Whitehead Institute for Biomedical Research, Cambridge, Mass.). Primers were designed to cross introns to ensure that only cDNA (and not DNA) was amplified. The fluorogenic MGB probe was labeled with the reporter dye FAM (6-carboxyfluorescein). TaqMan Universal PCR Master Mix (Applied Biosystems, Foster City, Calif.) was used to prepare the PCR mix. The 2× mixture was optimized for TaqMan reactions and contains AmpliTaq gold DNA polymerase, AmpErase, dNTPs with UTP and a passive reference. Primers and probe were added to a final concentration of 300 nM and 100 nM, respectively. The amplification reactions were carried out in the ABI Prism 7700 sequence detection system (Applied Biosystems) with initial hold steps (50° C. for 2 min, followed by 95° C. for 10 min) and 50 cycles of a two-step PCR (92° C. for 15 sec, 60° C. for 1 min). The fluorescence intensity of each sample was measured at each temperature change to monitor amplification of the target gene. The comparative CT method was used to determine fold differences between samples. The comparative CT method determines the amount of target, normalized to an endogenous reference (β-actin) and relative to a calibrator (2-ΔΔCt). The purity of PCR products were verified by gel electrophoresis.

Results

Bile duct ligation (BDL) or sham surgery (Sham) was performed as described above. Real-time RT-PCR was performed as described in the Materials and Methods. FIG. 15 illustrates hepatic mRNA expression of PAI-1 (FIG. 15A), Col1α1 (FIG. 15B) and αSMA (FIG. 15C). Results were normalized to beta actin; data are means±SEM (n=4-6) and are reported as fold over control values.

There is a significant decrease in alpha-smooth muscle actin indicating that CT140 decrease the population of myofibroblasts, the most prominent population of matrix producing cells.

Conclusion

Anti-PAI-1 humanized antibody CT140 was shown to protect mice from liver fibrosis.

Example 15

Rheumatoid Arthritis Animal Model

Induction of Arthritis

Antigen-induced arthritis (AIA) in mice is established as described previously (Brackertz et al., Arthritis Rhem., 20: 841-50 (1977)). Briefly, animals are immunized on days 0 and 7 with 100 μg methylated bovine serum albumin (MBSA; Sigma Chemical Company, Buchs, Switzerland) emulsified in 0.1 ml complete Freund's adjuvant (CFA) containing 200 μg mycobacterial strain H37RA (Difco, Basel, Switzerland) by intradermal injection at the base of the tail. On day 0, animals received, as an additional adjuvant, $2\times10^9$ heat-killed *Bordetella pertussis* organisms (Berna, Bern, Switzerland) injected intraperitoneally. Arthritis is induced in the right knee on day 21 by intra-articular injection of 100 μg of mBSA in 10 μl sterile phosphate-buffered saline (PBS), the left knee being injected with sterile PBS alone. Experimental mice are injected with anti-PAI-1 antibody; control animals are injected with PAI-1 or isotype control antibody.

Isotopic Quantification of Joint Inflammation

Joint inflammation is measured by $^{99m}$Tc uptake in the knee joint as described (Kruisjen et al., Agents Actions 11: 640-2 (1981)). Briefly, mice are first sedated by intraperitoneal administration of sodium pentobarbital (50 mg/kg) and then injected subcutaneously in the neck region with 10 μCi$^{99m}$Tc. The accumulation of the isotope in the knee is determined by external gamma-counting after 15 min. The ratio of $^{99m}$Tc uptake in the inflamed arthritic knee to $^{99m}$Tc uptake in the contralateral control knee is calculated. A ratio higher than 1.1 indicated joint inflammation.

Histological Grading of Arthritis

Mice are killed and the knees are dissected and fixed in 10% buffered formalin for 4 days. Fixed tissues are decalcified for 3 weeks in 15% ethylenediamine tetraacetic acid (EDTA), dehydrated and embedded in paraffin. Sagittal sections (6 μm) of the whole knee joint are stained with safranin-O and counterstained with fast green/iron haematoxylin. Histological sections are graded by two observers unaware of animal genotype or treatment. Synovial cell infiltrate and exudate are scored from 0 to 6 (0=no cells; 6=maximum number of inflammatory cells). Cartilage proteoglycan depletion (damage), reflected by loss of safranin-O staining intensity, is scored on a scale from 0 (fully stained cartilage) to 6 (totally unstained cartilage) in proportion to severity.

Fibrin Immunohistochemistry

Paraffin-embedded sections are processed for fibrin immunohistochemistry exactly as described before (van der Laan et al., Arthritis Rheum., 43: 1710-8 (2002)). Fibrin immunostaining in the synovial membrane is graded independently by two observers unaware of animal treatment on a scale from 0 (no fibrin at all) to 6 (maximum of fibrin staining).

Cryostat Section Preparation

Dissected knees are embedded in Tissue-Tek OCT, then immediately frozen in pre-cooled hexane and stored at −70° C. until use. Sections are cut on a motor-driven Leica cryostat with a retraction microtome and a tungsten carbide knife at a cabinet temperature of −25° C.

Tissue Protein Extract Preparation

Cryostat sections of joint tissue are homogenized in 50 mM Tris-HCl pH 7.5, containing 110 mM NaCl, 10 mM EDTA and 0.1% NP-40. The homogenate is centrifuged at 4000 g for 10 min at 4° C. and the supernatant stored at −20° C. Protein content of the tissue extracts is measured by the method of Bradford using BSA as a standard.

D-Dimer Measurements

The D-dimer concentration in tissue extracts is measured by a commercially available enzyme-linked immunosorbent assay (ELISA) kit designed for human D-dimer (Asserachrom D-Di; Diagnostica Stago, Asnières, France), which cross-reacts with murine D-dimer. The content of murine D-dimer is calculated according to the human D-dimer standard curve, normalized per mg of protein and expressed as the percentage of D-dimer in control mice.

Plasminogen Activators Zymographies

Tissue protein extracts are analyzed by sodium dodecyl sulphate-polyacrylamide gel electrophoresis (SDS-PAGE) zymography as described (van der Laan et al., Arthritis Rheum., 43: 1710-8 (2002)). Briefly, after SDS-PAGE of the samples, the gel is washed in Triton X-100 and layered over a casein underlay containing 2% non-fat dry milk, 0.9% agar and 40 μg/ml of purified human plasminogen in PBS (with 0.9 mM $Ca^{2+}$ and 1 ms $Mg^{2+}$). Underlays are incubated in a humidity chamber of 37° C. for 3-4 h, during which PAs diffused from the gel into the underlay, converting plasminogen into plasmin, which in turn lysed the insoluble casein. Zones of plasminogen-dependent caseinolysis appeared as black areas when visualized under dark-ground illumination. Photographs are taken using dark-ground illumination.

Statistical Analysis

The Wilcoxon rank sum test for unpaired variables (two-tailed) is used to compare differences between groups. P values<0.05 are considered significant.

Example 16

Multiple Sclerosis Animal Model

SCH-Induced EAE

Groups of mice receive 1 mg of freeze dried spinal cord homogenate (SCH) in Freund's adjuvant injected into the flanks on day 0, day 7 and day 28. The homogenate is emulsified in 300 μl incomplete Freudy's adjuvant (IFA; Difco, Beckton Dickenson, Oxford, UK) supplemented with 4 mg/ml of *Mycobacterium tuberculosis* (113 7Ra) (Difeo) and 1 mg/ml *Mycobacterium butyricurn* (Difco). Mice are monitored and weighed daily. Experimental animals are immunized with an anti-PAI-1 antibody or antigen-binding fragment thereof; control mice are injected with PBS or isotype control antibody.

Assessment of Functional Deficit in EAE Mice

Clinical disease is assessed and scored: 0=normal, 1=limp tail, 2=impaired righting reflex, 3=partial paralysis of hind limbs, 4=complete paralysis of hind limbs and 5=moribund/death. In addition, intermediate scores are given when appropriate: 0.5=loss of tail tonicity. 1.5=slower than normal righting reflex, 2.5=hind limb weakness and 3.5=paralysis of one hind-limb and paresis in the other. The mean day of onset, mean maximal score, mean score at experiment termination and the incidence of relapse are calculated from the data.

For specimen collection, mice are killed with $CO_2$ and immediately perfused intracardially with phosphate buffered saline (PBS). Samples are taken from various time points throughout CREAE to correspond to the acute, remission and relapse stages of disease [15-20, 30 and 40 days post induction (dpi)]. Spinal cords are removed under hydrostatic pressure [15]. Once removed, the tissue is immediately snap frozen on dry ice, wrapped in foil and stored at −70° C. until used.

Immunohistochemical Staining

Cryostat sections (10-μm) cut onto Vectabond-coated slides (Vector, Peterborough, UK) are fixed in methanol (−20° C., 5 min) and stained using a three-step peroxidase method as previously described in the art. Briefly, these are labeled with the primary antibody overnight at 4° C. or for 1 hour (h) at room temperature (RT) with antibodies against myelin basic protein (MBP) (1:2000, Chemicon, Hampshire, UK), phosphorylated neurofilament (SMI35; 1:10 000, Sternberger Monoclonals, Baltimore, Mass., USA), non-phosphorylated neurofilament (SM132; 1:5000, Sternberger Monoclonals) or CD45 (1:2000, Serotec. Kidlington, UK). This is followed by incubation with an appropriate horseradish peroxidase (HRP) conjugate. Sections stained for CD45 are counterstained with Mayer's haemotoxylin (VWR, Leicestershire. UK). Omissions of primary antibody, secondary antibody or avidin biotin complex are routinely used as controls.

Histopathological Evaluation

The total number of perivascular cuffs is determined in a spinal cord longitudinal section area of 4 cm$^2$ as described previously (East et al. Am. J. Pathol., 167: 545-554 (2005)). The average cuff count is taken from a total of three slides from three different mice per time point.

Protein Extraction and Western Blotting

Snap-frozen samples of spinal cord from mice are weighed, finely cut arid resuspended at 1:10 g wet weight/ml in Tris-HCl buffer pH 7.4 (100 mM Tris, 5 mM EDTA. 150 mM NaCl. with 1% Triton X-100). Samples are homogenized using a high-intensity ultrasonic processor (Jencons Scientific Ltd, Leighton Buzzard, UK) and incubated on ice for 30 minutes (min). The tissue suspensions are spun at 15000 g in an Eppendorf centrifuge for 60 min at 4° C. and the supernatants collected and stored in aliquots at −70° C. The total protein concentration of spinal cord homogenates is determined by the Folinphenol method (Lowry et al., J. Biol. Chem., 193: 265-75 (1951)).

For Western blot analysis, 40 μg of supernatant protein is resolved on a Tris-HCl 1 sodium dodecyl sulphatepolyacrylamide gel (SDS-PAGE; Bio-Rad, Hertfordshire, UK) and transferred to an Immobilon-P polyvinylidene difluoride membrane (Millipore, Bedlbrd, UK). Non-specific binding sites on the membrane are blocked with 5% Marvel® dried fat free milk (Premier International Food (UK) Ltd, Lincolnshire (UK) dissolved in Tris-buffered saline (T-TBS: 10 mmol/l Tris, pH 7.4, 150 mmol/l NaCl and 0.1% Tween 20) for 1 h at RT and then incubated with the primary antibody diluted 1:1000 in 5% Marvel® in T-TBS for 2 h at RT. After washing in T-TBS, the membrane is incubated with the secondary antibody, which is coupled to HRP: anti-mouse IgG HRP (1:1000, Affinity Bioreagents, Cambridge, UK), anti-rabbit IgG HRP (1:1000: Amersham Biosciences, Buckinghamshire, UK) or anti-goat IgG HRP (1:1000, Santa Cruz Biotechnology, Santa Cruz, Calif., USA) for 1 h at RT. After three final washes, the blots are developed by enhanced chemiluminescence (Amersham Biosciences). To gain a semiquantitative measure of specific proteins, resulting blots are analysed using the GelPro analysis software package (Media Cybernetics, Silver Springs, Md., USA) and the band density is measured in arbitrary units. To ensure equal loading of protein, membranes are stripped with Gelstrip (Chemicon) according to the manufacturer's instructions and probed with anti-β-actin antibody.

Enzyme-linked immunosorbant assays (ELISAs) are performed. Costar 96-well plates are coated with mouse antibodies against PAI-1, tPA or uPA at 4 μg/ml for 48 h at 4° C. (Declerck et al., Thromb. Haemost, 74: 1305-9 (1995)). The wells are blocked with 1% bovine serum albumin (BSA) in 1×PBS overnight at 4° C. and plates are then washed with 1×PBS Tween 80 (0.004%). Protein extract samples and standards are diluted in 1×PBS containing 0.004% Tween 80, 0.1% BSA and 5 mM EDTA, and are added 180 μl per well and incubated overnight at 4° C. Standard curves ranged from 0.023 to 3 ng/ml (PAI-1), 0.078-10 ng/ml (tPA) and 0.156-20 ng/ml (uPA). After washing, a biotinylated secondary antibody (PAI-1, tPA or uPA) is added for 1 h at 37° C. After addition of the ABC complex (Vector) for 1 h at RT, plates are developed using o-phenylenediamine, and the reaction is stopped using 4 M sulphuric acid. Absorbance is read at 490 nm with a reference reading at 650 nm. Assessment of tPA activity is performed by ELISA (Oxford Biomedical Research, Biogenesis, Dorset, UK) and is carried out according to the manufacturers instructions.

Clot Lysis Assay

In order to investigate the fibrinolytic capacity of different CNS tissue extracts, and to determine whether this changed during experimental neuroinflammation, a clot lysis assay is performed as previously described (Urano et al., Haemostasis, 26: 220-7 (1996)). Spinal cord tissue protein extracts are mixed 1:10 with dilution buffer (50 mM Tris, 0.2% Triton X-100, pH 7.4 with HCl). Forty microliters of diluted sample or standard is mixed with 360 μl of dilution buffer containing 7.3 μM human fibrinogen (Sigma), 0.25 μM human lysplasminogen (Chromogenix. Milan, Italy), 1.7 mM $CaCl_2$, 0.7 mM $MgCl_2$ and 12.5 mM NaCl. Samples are added in duplicate (180 μl per well) to 96-well microtitre plates containing 20 μl human thrombin per weL1 (100 U/ml, Sigma) and incubated at 37° C. Absorbance is measured at 405 nm in 15- or 30 mm intervals for 5 h. Human recombinant tpA (2 mg/ml: Technoclone, Dorking, Surry, UK) mixed with dilution buffer is used as a positive control, while omission of sample or plasminogen in the buffer is used as a negative control.

Statistical Analysis

Data are analyzed with the GraphPad Prism computer package (GraphPad Software, San Diego, Calif., USA). A normality and quality of variance test is performed on all data to determine which test is appropriate. A t-test, for normally distributed data sets, or a Mann-Whitney U-test, for nonparametric data, is used with significance level set at 95%. If variances of data sets are significantly different Welch's correction is applied to correct for this. The P-value for significance is adjusted for multiple comparisons to 0.21 using the Bonferroni correction method for analysis of clinical score data. For analysis of disease incidence, a Kaplan-Meier survival curve is analyzed using a logrank test. The parametric Pearson's correlation test is used for the regression analysis and the r-value given where appropriate. All values are indicated as the mean±standard error of the mean (SEM). P-values are taken as an indicator of statistical significance: *P<0.05, P<0.01 and *P<0.001.

Example 17

Inhibition of Cell Migration

Materials—Placenta-derived human LRP is obtained. A plasmid encoding glutathione S-transferase fused to RAP (GST-RAP) is obtained and used for expression of GST-RAP in *Escherichia coli* DH5α. As the GST tag does not interfere with the binding properties of RAP, GST-RAP is used throughout the present study and is referred to as RAP. The BIACORE®3000 biosensor system, reagents, and CM5 sensor chips (research grade), are from Biacore AB (Uppsala, Sweden). Human fibronectin is from Roche Applied Science. Nonspecific rabbit and mouse IgG, as well as collagen I, formylated peptide fMLP, FITC-, and TRITC-phalloidin are from Sigma. Rabbit anti-phosphotyrosine polyclonal antibody, and anti-mouse IgG rhodamine conjugated F(ab')$_2$ fragment secondary antibody, are from Chemicon (Temecula, Calif.). Mouse anti-human Jak1 and anti-human Stat1 monoclonal antibodies are from BD Biosciences, Transduction Laboratories (Lexington, Ky.). The Jak inhibitor AG-490 is from Biomol (Plymouth Meeting, Pa.). VN is purified from human plasma as described previously. Antibodies against human PAI-1 are those as described. The polyclonal antibody against human LRP is from RDI, Research Diagnostics (Flanders, N.J.), and further purified using the affinity chromatography kit MabTrap G II (Amersham Biosciences).

Cell Culture—Human smooth muscle cells (AoSMC, CASMC), human endothelial cells (HAEC, HCAEC) from the aortic and coronary arteries, respectively, and human dermal microvascular endothelial cells, neonatal (HMVEC-d neo), are cultured according to the supplier (Clonetics, Charlotte, N.C.). Rat smooth muscle cells (RSMC) are obtained for use. MEF-1 are wild-type murine embryonic fibroblasts derived from the same mouse strain as MEF-2. MEF-2 is genetically deficient in LRP. RSMC, HT-1080 (highly invasive human fibrosarcoma cells), IF6 (non-invasive human melanoma cells that do not express uPA), MEF-1, and MEF-2 cells are cultured in Dulbecco's modified Eagle's medium plus 10% fetal calf serum.

Migration Assays—Chemotaxis assays are performed as previously described, using modified Boyden chambers. Briefly, ~50,000 cells are added to the upper well of Boyden chambers, and the molecules to be tested are added to the lower well in serum-free medium. Anti-PAI-1 antibodies or control antibodies are added to both wells. Haptotaxis assays are performed under the same conditions, except that the filters are washed with serum-free Dulbecco's modified Eagle's medium containing 0.2% bovine serum albumin, and then preincubated with the indicated amounts of PAI-1 or fibronectin in the Dulbecco's modified Eagle's medium solution for 3 h at 37° C. The filters are washed, and then serum-free medium is added to both the upper and lower wells. Wounding assays are performed as previously described. Briefly, confluent monolayers are scraped with a pipette tip, and the number of cells migrating into the wound over the next 24 h is then determined. Chemokinesis assays are performed as described, except that cells are stimulated for increasing times with 2 nM PAI-1 in the presence or absence of 5 μg/ml RAP, and are only labeled with phalloidin. The cells are then counted using an Olympus UplanF 1 40 lens. Quantification of the actin cytoskeleton reorganization is performed by taking low magnification photographs and counting the resting cells (those that exhibit numerous stress fibers and a non-polarized morphology) and non-resting cells (polarized cell shape with reorganized actin cytoskeleton due to a decrease in stress fibers, and increased membrane ruffling and actin semi-rings). All experiments are performed at least twice in triplicate. Results are the mean±S.E. of the number of cells counted in ten high power (×40) fields per filter and expressed as fold over control. Random cell migration (i.e. migration in the absence of chemoattractant) is given the arbitrary value of 100%.

Immunofluorescence Microscopy—Cells are cultured, fixed, stained, and mounted as described, except that in some experiments, cells are pretreated for 5 min with RAP (5 μg/ml). Cells are stained either with anti-phosphotyrosine, anti-Jak1, or anti-Stat1 antibody, and then are double-stained with phalloidin for visualization of filamentous actin. In some cases, the above cells are triple stained by employing the additional nucleus probe DAPI (4',6-diamidino-2-phenyliadole, Roche Applied Science). Fluorescence photographs are taken using an Olympus BX60 microscope coupled to a DVC camera using Olympus UplanFI 100 lens, and analyzed with C-view and Image pro-plus software.

Example 18

Assessment of Human Tumor Angiogenesis

Materials and Methods

An in vitro human tissue-based angiogenesis model is created that allows the outgrowth of microvessels from a three-dimensional tissue fragment implanted in a fibrin-based matrix. The fibrin matrix is supplemented by a growth medium. The differential growth pattern of tumor cells and angiogenic vessels in the fibrin gel matrix separates the angiogenic vessels and the tumor stroma into two independently observable regions of interest (vessel and tissue compartments). The angiogenic potential of a tissue can be determined by measuring the growth of microvessels into the matrix.

Preparation of the Assay Plates

Preparation of Tumor Fragments

Fresh tumors are processed immediately after harvesting. Tumor fragments 2 mm in diameter and 1 mm thick are created and immediately embedded into fibrin gels. The fibrin gels are prepared in 96-well plates by using a specific tumor-supporting medium, as described below.

Preparation of the Tissue-Supporting Medium

A serum-free growth medium consisting of a balanced salt solution, an antibiotic-antifungal solution, and an endothelial growth medium is buffered to a pH of 7.4. Specifically, 9.5 g of medium 199 (Gibco BRL, Grand Island, N.Y.) is dissolved in 980 mL of deionized $H_2O$. Ten milliliters of antibiotic-antimycotic solution (Gibco) containing 10,000 U of penicillin base, 10,000 U of streptomycin base, and 25•g of amphotericin B is added. The pH is then adjusted by adding 2.2 g of $NaHCO_3$ (EM Science, Gibbston, N.J.). This is further titrated with 1 N NaOH to pH 7.4. This solution is mixed with endothelial growth medium (Gibco) in a 3:1 ratio and sterilized by passing it through a 22-•m filter. Endothelial growth medium is a commercially available serum-free medium designed for the growth and maintenance of vascular endothelial cells.

Preparation of Fibrin Matrix Components for Tumor Fragment Embedding

A procoagulation solution is prepared by dissolving fibrinogen (0.12 g: Sigma, St. Louis, Mo.) and 0.2 g of •-aminocaproic acid in 40 mL of endothelial growth medium. Human thrombin (2•L; Sigma) is placed in the bottom of each well of a 96-well plate and allowed to evaporate until dry.

Final Assembly of the Fibrin Matrix Tumor System and Maintenance of the Well Plates Each tumor disk is placed in the center of a thrombin-treated well. The procoagulation solution (0.2 mL) is carefully layered over the tumor fragments to prevent the formation of air bubbles in the clot. Fibrin clot formation took place within 20 to 30 minutes at 37° C. A layer of tissue-supporting medium is added over the fibrin gel. The plates are kept at 37° C. in a 5% $CO_2$/95% air humidified atmosphere. Anti-PAI-1 antibodies as described herein are added to test samples; control antibodies are added to control samples.

Confirmation and Evaluation of the Angiogenic Response

Individual wells containing tumor fragment/angiogenic vessel compartments are examined under an inverted phase microscope. Histopathologic evaluation is performed with standard techniques.

Viability Assay

Cell/tissue viability is evaluated by using a colorimetric 3-(4,5-dimethylthiazol-2-yl)-2,5-diphenyltetrazolium bromide (MTT) assay (Promega, Madison, Wis.). This assay is based on the cellular conversion of a tetrazolium salt into a blue formazan product. The MTT assay is performed at the end of a specified time period both on the tissue fragment and on angiogenic sprouts. Viable cells convert the colorless tetrazolium salt into a blue end product.

Histopathology and Immunohistochemistry

Histopathologic assessment is performed by hematoxylin and eosin staining. Immunohistochemistry is performed with anti-factor VIII antibody.

Angiogenic Response Measures

To determine the extent of neovessel growth, each well containing tumor fragment/angiogenic vessel compartments is visually divided into four quadrants, and each quadrant is rated on a 0 to 4 scale for the amount (length, density, and percentage of the circumference involved in the angiogenic response) of angiogenic growth (FIG. 3). A total score of 0 to 16 is calculated for each well.

Angiogenic Growth Fraction

The angiogenic growth fraction is defined as the percentage of tumor fragments that developed capillary growth into the fibrin matrix. Angiogenic fraction (AF) is the number of wells in which any angiogenic activity is observed during the observation period (day 2 to day 14) divided by total number of wells.

Angiogenic Index

The AI is the mean of the angiogenic scores (AS) of all angiogenic wells on day 14:

AI••AS (Excluding AS•0)!/•wells (excluding AS•0 AS•0)

Tumor Fragment Sources

Human Tumor Xenografts

Three different human carcinoma cell lines obtained from the American Tissue Culture Collection (Rockville, Md.) are used to create xenografts. The human breast carcinoma cell line MDA-MB0231 is maintained in Lebowitz's L-15 medium (Life Technologies, Inc., Grand Island, N.Y.) and supplemented with 10% fetal bovine serum (FBS; Life Technologies). The human neuroblastoma cell line IMR-32 is maintained in minimum essential medium (Life Technologies) and supplemented with 15% FBS, nonessential amino acids (Life Technologies), L-glutamine (Cellgro; Mediatech, Herdon, Va.), and antibiotics. The human prostate cancer cell line LNCaP is maintained in 85% to 90% RPMI 1640 and supplemented with 10% to 15% FBS. Cells are harvested at subconfluence and resuspended in Hank's balanced salt solution (Life Technologies).

Nude mice are injected with $1.5 \times 10^7$ tumor cells subcutaneously in both flank regions. Injected mice invariably grew solid tumors over a period of 4 to 6 weeks. Tumors are allowed to reach a size of 1.5 to 2 cm. Tumor harvesting is performed with sterile techniques under inhaled anesthesia with methoxyflurane, and the animals are killed immediately after tumor collection. All animal experiments are performed with the approval of the Louisiana State University Health Sciences Center's Institutional Animal Care and Use Committee.

Fresh Human Tumor Tissues

Fresh discarded tissue samples are anonymously obtained (with approval) from fresh surgical specimens of patients with breast cancer and thyroid cancer.

Example 19

Modulation of Adipocyte Differentiation

Cell culture. To determine the effects of PAI-1 deficiency on adipocyte differentiation, glucose uptake, and TNF-α-induced insulin resistance, primary cultures of adipocytes are obtained from 4-wk-old male PAI-1+/+ or PAI-1−/− mice (both on C57BL/6 background) as previously described. Differentiation of preadipocytes to adipocytes is induced by addition of an adipogenic hormonal cocktail (1 µg/ml insulin, 0.25 µM dexamethasone, and 0.5 mM isobutylmethylxanthine) and confirmed morphologically by multiple oil red O-stained fat droplets in the cytoplasm. Primary adipocytes at day 10 after induction of differentiation are used for this study. Insulin-resistant primary adipocytes are obtained by incubating these differentiated 10-day adipocytes for an additional 3 days in the presence of 3 ng/ml TNF-α (Sigma, St. Louis, Mo.) with or without insulin stimulation for 10 min.

For studies of altered PAI-1 expression, murine 3T3-L1 Preadipocytes are used (American Type Culture Collection, Manassas, Va.) grown in DMEM supplemented with 10% fetal bovine serum, 2 mM L-glutamine, 50 U/ml penicillin, and 50 µg/ml streptomycin at 37° C. in 5% $CO_2$. After confluence is reached (2 days), differentiation is initiated with adipogenic hormonal cocktail as described above for 2 days and then with DMEM containing insulin (1 µg/ml) alone for 2 days, followed by an additional 2 days in medium without insulin. These differentiated 3T3-L1 adipocytes at day 6 exhibit intracellular lipid droplets and are used for this study. To inhibit PAI-1, 3T3-L1 preadipocytes are treated for 6 days with a neutralizing antibody against PAI-1 (e.g., those described herein, 10 µg/ml) along with induction of differentiation. A class-matched, non-inhibitory antibody (e.g., MA-32K3) is used as a control antibody.

Adenoviral infection of 3T3-L1 preadipocytes. Recombinant adenovirus bearing human PAI-1 (Ad-PAI-1) and control adenovirus expressing Escherichia coli β-galactosidase (Ad-lacz) are obtained. The recombinant viruses are propagated in HEK 293 cells and purified by CsCl density gradient centrifugation. 3T3-L1 pre-adipocyte cultures (2 days post-confluence) in six-well plates are infected with the Ad-PAI-1 or Ad-lacz by addition of $1 \times 10^9$ plaque-forming units/well for 3 h before induction of differentiation. The medium containing free virus is then removed, fresh DMEM with 10% fetal bovine serum is added, and cells are induced to differentiate as above.

Oil Red O staining. Differentiation of pre-adipocytes to adipocytes is monitored by measurement of intracellular lipid accumulation using Oil Red O staining. After fixation with 10% formalin in PBS for 1 h, the cells are washed and stained with filtered 0.3% Oil Red O in 55% isopropanol for 1 h, followed by counterstaining with 0.5% methyl green (Polysciences, Warrington, Pa.) in 0.1 M sodium acetate, pH 7.4. Differentiation is calculated as percent cells with Oil Red O positivity of total cells, assessed under ×100 magnification.

Glucose uptake. [2-3H]deoxyglucose uptake is measured as described previously. Briefly, primary adipocytes (10 days post-differentiation) and 3T3-L1 adipocytes (6 days post-differentiation) in six-well plates are cultured overnight in serum free-DMEM with low glucose (1 g/l). After KRP buffer wash (containing 136 in M NaCl, 4.7 mM KCl, 1 mM $CaCl_2$, 1 mM MgSO4, 5 mM sodium pyrophosphate, 20 mM HEPES, and 1% BSA), cells are incubated with 1 ml KRP buffer at 37° C. for 20 min in the presence or absence of insulin as indicated. [2-3H]deoxyglucose is added for a final concentration of 0.1 mM (11.0 Ci/mmol; PerkinElmer Life Sciences, Boston, Mass.) and incubated for 10 min at 37° C. The cells are washed with cold KRP buffer and solubilized in 0.1% SDS. The radioactivity of a 200-µl aliquot is determined in a scintillation counter. Glucose uptake is expressed as the degree of increase compared with basal PAI-1+/+ or 3T3-L1 cells, normalized to protein concentration in each sample.

RNA extraction and assessment. Total RNA is extracted from cells as described previously. Relative quantitation of expression of several murine genes in primary adipocytes and 3T3-L1 adipocytes is determined by a real-time, one-step RT-PCR assay (TaqMan) using an ABI Prism 7700 sequence detection system (Applied Biosystems, Foster City, Calif.). A 25-µl reaction mixture
containing 2 µg of total RNA, 0.5 µM of each primer, and 0.2 µM TaqMan probe is mixed with 25 µl of the TaqMan One-Step RT-PCR 2× Master Mix (Applied Biosystems), as described previously. Primers and probes designed to target mouse PPARγ, adiponectin, resistin, PAI-1, uPA, and collagen I genes. The reaction conditions are designed as follows: RT at 48° C. for 30 min and initial denaturation at 95° C. for 10 min followed by 40 cycles with 15 s at 95° C. for denaturing and 1 min at 60° C. for annealing and extension. The threshold cycle (CT), i.e., the cycle number at which the amount of amplified gene of interest reached a fixed threshold, is subsequently determined. Relative quantification of each target mRNA level is normalized to 18S rRNA or β-actin and calculated by the comparative CT method described elsewhere.

Immunofluorescence. 3T3-L1 cells cultured on cover slips are infected with Ad-PAI-1 or Ad-lacz or not treated as described above. After fixation in methanol-acetone (1:1) for 10 min at room temperature, the cells are permeabilized and blocked with 0.1% Triton X-100 and 5% BSA in PBS for 10 min. After being washed, the cells are then incubated with sheep anti-PAI-1 antibody (1:25; American Diagnostica, Stamford, Conn.) or goat anti-β-Gal antibody (1:25; Biogenesis) for 1 h at room temperature. FITC-conjugated rabbit anti-sheep IgG (DakoCytomation, Carprinteria, Calif.) or FITC-conjugated rabbit anti-goat IgG antibodies (Dako) are then applied and incubated for 1 h. Internalization of inhibitory PAI-1 antibody or control antibody in 3T3-L1 cells is assessed by direct staining of permeabilized cells with fluorochrome tetramethylrhodamine isothiocyanate-conjugated rabbit anti-mouse IgG (1:25; Dako). Images of immunofluorescent cells are captured with a Zeiss AxioCam camera attached to a Nikon Eclipse E400 microscope.

Western blotting. Adipocytes (primary and 3T3-L1) grown in six-well plates are induced to differentiate along with treatments indicated above. Cells are lysed in lysis buffer [containing 150 mM NaCl, 50 mM Tris-HCl, pH 7.5, 5 mM EDTA, 1% Nonidet P-40, 0.5% sodium deoxycholate, 0.1% SDS, 100 µg/ml phenylmethylsulfonyl fluoride, and 1:100 proteinase inhibitor cocktail tablet (Roche Diagnostics, Mannheim, Germany)]. Total protein (30 µg) is separated on SDS-PAGE and transferred to a nitrocellulose membrane. Western blottings are performed with polyclonal rabbit antibodies against PPARγ (catalog no. 2492; Cell Signaling Technology, Beverly, Mass.), C/EBPα (14AA; Santa Cruz Biotechnology, Santa Cruz, Calif.), or fatty acid-binding protein (aP2, C-15; Santa Cruz Biotechnology). The blots are subsequently incubated with horseradish peroxidase (HRP)-conjugated donkey anti-rabbit IgG (Amersham Biosciences, Little Chalfont, UK) or HRP-conjugated bovine anti-goat IgG (Santa Cruz Biotechnology). Immunoreactive proteins are detected and visualized by using enhanced chemiluminescence detection reagents (Amersham Biosciences). The membranes are restripped for β-actin by using monoclonal anti-β-actin antibody (Sigma), as a control for normalization.

Plasmin activity. Total plasmin activity in 3T3-L1 cells lysis is measured by a modified protocol as described previously using a plasmin-specific chromogenic substrate (Chromozym PL; Roche Molecular Biochemicals, Indianapolis, Ind.). This substance is specifically cleaved by plasmin into a residual peptide and 4-nitroaniline, which can be detected spectrophotometrically. 3T3-L1 adipocyte lysis (80 µl) and 20 µl of 3 mM Chromozym PL are added per reaction.

Absorbance is measured at 405 nm. A standard linear curve is generated with serial dilutions of human plasmin (Roche). Results are expressed as units per milligram protein.

Statistical analysis. Data are presented as means SE, unless otherwise noted. P values are calculated by ANOVA followed by unpaired t-test as appropriate. A P value of <0.05 is considered to be significant.

Example 20

Age-Related Macular Degeneration and Choroidal Neovascularization

RT-PCR Analysis of Human and Murine Neovascular Membranes

The methods conform to the tenets of the Declaration of Helsinki for research involving human subjects. Submacular CNV (SCNV) specimens are completely removed during surgery for 360° macular translocation in patients with exudative AMD that is not amenable to conventional laser or photodynamic therapy. The specimens are immediately frozen in liquid nitrogen and stored at −80° C. until RT-PCR analysis.

At selected intervals (days 3-40) after laser induction in mice (described later), choroidal neovascular membranes and adjacent neural retina intact regions are separately extracted from frozen sections by laser capture microdissection (laser pressure catapulting [LPC] technique) as previously described. The specimens are covered with 100 µL lysis buffer, and total RNA isolation is performed with a kit (PUREscript RNA Isolation Kit; BIOzym, Landgraaf, The Netherlands) according to the manufacturer's protocol.

The frozen murine and human tissues are first pulverized using a dismembrator (B. Braun Biotech International, GmBH, Melsungen, Germany) and total RNA is extracted with a kit (RNeasy; Quiagen, Paris, France) according to the manufacturer's protocol. 28S rRNA is amplified with an aliquot of 10 ng of total RNA, with a reverse transcriptase RNA PCR kit (GeneAmp Thermostable rTth; Applied Biosystems, Foster City, Calif.) and two pairs of primers (identical for human and murine; sense: 5'-GTTCACCCACTAATAGG-GAACGTGA-3' and reverse: 5'GGATTCTGACTTFAGAG-GCGTTCAGT-3' for 28S mRNA; and sense: 5'-AGGGCT-TCATGCCCCACTTCTTCA-3' and reverse: 5'-AGTAGAGGGCATTCACCAGCACCA-3' for PAi-1 (Eurogentec, Liege, Belgium). Reverse transcription is performed at 70° C. for 15 minutes followed by a 2-minute incubation at 95° C. for denaturation of RNA-DNA heteroduplexes. Amplification (33 cycles for PAI-1 and 19 cycles for 28S, or 45 cycles for PAI-1 and 35 cycles for 285 in the case of LPC material) started by a cycle of 15 seconds at 94° C., 20 seconds at 60° C. and 10 seconds at 72° C. RT-PCR products are resolved on 2% agarose gels and analyzed with a fluorescence imager (Fluor-S MultiImager; Bio-Rad, Richmond, Calif.) after staining with ethidium bromide (FMC BioProducts, Philadelphia, Pa.). The expected size for RT-PCR products is 212 bp for 28S and 197 bp for PAI-1.

Murine Model of Laser-Induced Choroidal Neovascularization

Mice of either sex, 2 to 4 months old, with a mixed genetic background of 87% C57BL/6 and 13% 129 strain, are used throughout the study. The animals are maintained with a 12-hour light-dark cycle and had free access to food and water. Animal experiments are performed in compliance with the ARVO Statement for the Use of Animals in Ophthalmic and Vision Research. Test animals are treated with neutralizing anti-PAI-1 antibodies and control animals are treated with non-neutralizing isotype control antibodies.

CNV is induced in mice by four burns (usually at the 6, 9, 12, and 3 o'clock positions around the optic disc) with a green argon laser (532 nm, 50 μm diameter spot size; 0.05-second duration, 400 mW) as previously described. Mice with hemorrhaging or that do not exhibit an evident bubble at the site of every Laser impact (the sign of a ruptured Bruch's membrane) are excluded from further analysis. Included animals (five or more m each condition) are killed at day 14 (except for spatial and temporal mRNA profiles). Before death, fluorescein angiograms (intraperitoneal injection of 0.3 mL of 1% fluorescein sodium: Ciba, Mechelen, Belgium) are performed to confirm that laser burns are showing late-phase increasing hyperfluorescent spots (corresponding to the leakage of fluorescein from newly formed permeable capillaries). The eyes are then enucleated and either fixed in buffered 3.5% formalin solution for routine histology or embedded in optimal cutting temperature compound (Tissue TeK; Miles Laboratories, Naperville, Ill.) and frozen in liquid nitrogen for cryostat sectioning. CNV is quantified as previously described. Briefly, frozen serial sections are cut throughout the entire extent of each burn, and the thickest region (minimum of five per lesion) selected for the quantification. Using a computer-assisted image-analysis system (Micro Image version 3.0 for Windows 95/N1; Olympus Optical Co. Europe GmbH, Birkeroed, Denmark), neovascularization is estimated by the ratio (B/C) of the thickness from the bottom of the pigmented choroidal layer to the top of the neovascular membrane (B) to the thickness of the intact-pigmented choroid adjacent to the lesion (C). A mean B/C ratio is determined for each laser impact.

Immunohistochemistry

Cryostat sections (5 μm thick) are fixed in paraformaldehyde 1% in 0.07 M phosphate-buffered saline (PBS; pH 7.0) for 5 minutes or in acetone for 10 minutes at room temperature and then incubated with the primary antibody. Antibodies raised against mouse platelet endothelial cell adhesion molecule (PECAM; rat monoclonal, diluted 1:20; PharMingen, San Diego, Calif.), and murine fibrinogen/fibrin (diluted 1:400, goat polyclonal antibody; Nordic Immunologic, Tilburg, The Netherlands) are incubated for 1 hour at room temperature. The sections are washed in PBS (three times, 10 minutes each) and appropriate secondary antibody conjugated to horseradish peroxidase (HRP), or tetramethylrhodamine isothiocyanate (TRITC) are added: rabbit anti-goat IgG (diluted 1/100; Dako, Glostrup, Denmark) and rabbit anti-rat IgG (diluted 1/40; Sigma-Aldrich, St. Louis, Mo.) are applied for 30 minutes. For immunostaining of fibrinogen/fibrin, a drop of 3-amino-9-ethylcarbazole AEC+; Dako) is added, and sections are counterstained for 1 minute in hematoxlin. For immunofluorescence staining, after three washes in PBS for 10 minutes each and a final rinse in 10 mM Tris-HCl buffer (pH 8.8), labeling is analyzed under an inverted microscope equipped with epifluorescence optics. Specificity of staining is assessed by substitution of non-immune serum for primary antibody (not shown).

Statistical Analysis

Data are analyzed on computer (Prism 3.0; GraphPad, San Diego Calif.). The Mann-Whitney test is used to determine whether there are significant (P<0.05) differences between different experimental conditions.

Example 21

The following example describes the effect of anti-PAI-1 antibodies on early stages of alcoholic liver disease (ALD) in an in vivo mouse model.

The effect of ethanol pretreatment on LPS-induced liver injury and fibrin deposition was determined in mice. Ethanol enhanced liver damage caused by LPS, as determined by plasma parameters and histological indices of inflammation and damage. This effect was concomitant with a significant increase in PAI-1 expression. Extracellular fibrin accumulation caused by LPS was also robustly increased by ethanol pre-exposure. Co-administration of the thrombin inhibitor hirudin or the MEK inhibitor U0126 significantly attenuated the enhanced liver damage caused by ethanol pre-exposure; this protection correlated with a significant blunting of the induction of PAI-1 caused by ethanol/LPS. Furthermore, thrombin/MEK inhibition prevented the synergistic effect of ethanol on the extracellular accumulation of fibrin caused by LPS. Similar protective effects on fibrin accumulation were observed in mice injected with PAI-1 inactivating antibody.

These results suggest that enhanced LPS-induced liver injury caused by ethanol is mediated, at least in part, by fibrin accumulation in livers, mediated by an inhibition of fibrinolysis by PAI-1. These results also support the hypothesis that fibrin accumulation may play a critical role in the development of alcohol-induced liver injury.

Animals and Treatments

Six week old male C57BL/6J mice were purchased from The Jackson Laboratory (Bar Harbor, Me.). Mice were housed in a pathogen-free barrier facility accredited by the Association for Assessment and Accreditation of Laboratory Animal Care, and procedures were approved by the University of Louisville's Institutional Animal Care and Use Committee. Food and tap water were allowed ad libitum.

Animals received ethanol (6 g/kg i.g.) or isocaloric/isovolumetric maltose-dextrin solution for 3 days. LPS (*E. coli*, serotype 055:B5; Sigma, St Louis, Mo.; 10 mg/kg intraperitoneally (i.p.)) was injected 24 h after the last ethanol administration. Hirudin (Refludan, Berlex, Montville, N.J., 1 mg/kg subcutaneously (s.c.)) or vehicle (saline) was given 30, 150 and 270 minutes after LPS. U0126 (Calbiochem, La Jolla, Calif., 10 mg/kg i.p.) or vehicle (DMSO) was administered 60 minutes after LPS. Test mice were injected with PAI-1 inactivating antibody i.p. (200 μl/mouse; ~10 mg/kg) 30 mm prior to injection with LPS. Mice were anesthetized with ketamine/xylazine (100/15 mg/kg, intramuscularly i.m.) at select time points up to 48 h after injection with LPS (timeline, FIG. 18). Blood was collected from the vena cava just prior to sacrifice by exsanguination, and citrated plasma was stored at −80° C. for further analysis. Portions of liver tissue were snap-frozen in liquid nitrogen, frozen-fixed in OCT-Compound (Sakura Finetek, Torrance, Calif.), or were fixed in 10% neutral buffered formalin for subsequent sectioning and mounting on microscope slides.

Clinical Analyses and Histology

Plasma levels of aminotransferases (ALT and AST) and hepatic levels of triglycerides were determined using standard kits (Thermotrace, Melbourne, Australia). Paraffin-embedded sections were stained for hematoxylin & eosin (H&E); pathology was scored in a blinded manner by a trained pathologist. Oil Red O staining, chloroacetate esterase staining and neutrophil accumulation in the livers was assessed as described before. The intensity and extent of CAE staining in liver tissues were quantified by counting CAE-positive neutrophils per 1000 hepatocytes. Plasma thrombin-antithrombin (TAT) concentration was determined by enzyme-linked immunosorbent assay using a kit (Dade Behring Inc., Deerfield, Ill.). The accumulation of fibrin matrices was determined immunofluorometrically, as described previously.

RNA Isolation and Real-Time RT-PCR

RNA extraction and real-time RT-PCR was performed. PCR primers and probes were designed using Primer 3 (Whitehead Institute for Biomedical Research, Cambridge, Mass.). Primers were designed to cross introns to ensure that only cDNA and not genomic DNA was amplified. Sequences of primers used are described in the following table:

|  | Forward (3'-5') | Reverse (3'-5') | Probe (3'-5') |
| --- | --- | --- | --- |
| PAI-1 | CACCAACATTTTGGACGCTGA (SEQ ID NO: 120) | TCAGTCATGCCCAGCTTCT CC (SEQ ID NO: 123) | CCAGGCTGCCCCGCCTCCT C (SEQ ID NO: 126) |
| TNFα | CATCTTCTCAAAATTCGAGTGA CAA (SEQ ID NO: 121) | CCTCCACTTGGTGGTTTGCT (SEQ ID NO: 124) | CCTGTAGCCCACGTC (SEQ ID NO: 127) |
| B-actin | GGCTCCCAGCACCATGAA (SEQ ID NO: 122) | AGCCACCGATCCACACAGA (SEQ ID NO: 125) | AAGATCATTGCTCCTCCTG AGCGGAAGTA (SEQ ID NO: 128) |

Immunoblots

Liver samples were homogenized in RIPA buffer [20 mM Tris/Cl, pH 7.5, 150 mM NaCl, 1 mM EDTA, 1 mM EGTA, 1% (w/v) Triton X-100], containing protease and phosphatase inhibitor cocktails (Sigma, St. Louis, Mo.). Samples were loaded onto SDS-polyacrylamide gels of 10% (w/v) acrylamide followed by electrophoresis and Western blotting onto PVDF membranes (Hybond P, GE Healthcare, Piscataway, N.J.). Primary antibodies against phosphorylated and total ERK1/2 (Cell Signaling Technology; Beverly, Mass.) were used. Bands were visualized using an ECL kit (Pierce, Rockford, Ill.) and Hyperfilm (GE Healthcare, Piscataway, N.J.). Densitometric analysis was performed using ImageQuant (GE Healthcare, Piscataway, N.J.) software.

Statistical Analyses

ANOVA with Bonferroni's post-hoc test or the Mann-Whitney Rank Sum test was used for the determination of statistical significance among treatment groups, as appropriate. Results are reported as means±SEM (n=4-6). $^a$, $p<0.05$ compared to the absence of LPS; $^b$, $p<0.05$ compared to the absence of ethanol; $^c$, $p<0.05$ compared to EtOH+LPS in wild type mice.

Results

Effect of Ethanol on Hepatic Lipid Accumulation and Triglycerides

FIG. 18 shows a schedule of induction of livery injury (FIG. 18A), representative photomicrographs depicting lipid accumulation in the liver (Oil Red O stain, Figures) and a time course (FIG. 18F) of hepatic triglycerides in the model. As has been observed previously, lipid staining and triglyceride levels in livers from maltose-dextrin treated animals were minimal and did not differ from staining in livers from naïve control mice. In contrast, ethanol treatment caused significant accumulation of lipid droplets and triglycerides in livers of wild-type animals increased up to 12 h after administration (FIG. 18D, time point –12 h). By the time of LPS injection (t=0; 24 h after ethanol exposure), lipid levels had almost returned to basal levels (FIG. 18E).

Effect of Ethanol on Liver Damage Caused by LPS

Plasma levels of indices of liver damage (AST, ALT) were within normal ranges in mice exposed to maltose-dextrin in the absence of LPS (FIG. 19); ethanol alone did not significantly alter AST and ALT levels compared to these control animals. LPS injection alone significantly increased the level of ALT and AST released into the plasma 24 h after injection (FIG. 19). As has been observed previously, pretreatment with ethanol significantly enhanced the increase in plasma ALT and AST caused by LPS at the 24 h time point by a factor of ~3 (FIG. 19).

FIG. 19 shows representative photomicrographs depicting liver pathology (H&E stain, left column) and neutrophil accumulation (chloroacetate esterase stain, right column) 24 h after injection with LPS. The pathology score was determined: no pathological changes were observed in liver tissue after maltose-dextrin or ethanol exposure alone (FIG. 21A). Photomicrographs of livers from maltose-dextrin-injected mice are shown to represent both of the groups ("Control"; FIG. 19A). LPS at this dose caused no gross morphological changes to liver (FIG. 19B), but increased the inflammatory and necrosis scores (FIG. 21A) as well as the number of infiltrating neutrophils (FIG. 19E; FIG. 21B). The combination of ethanol and LPS increased hepatic damage, with necroinflammatory foci detectable macroscopically (FIG. 20C), which lead to increased pathology scores (FIG. 21A). Ethanol also enhanced the effect of LPS (~2.5 fold) on the recruitment of neutrophils to the liver (FIG. 20F; FIG. 21B). The pathologic changes caused by the combination of ethanol and LPS were attenuated when mice were injected with PAI-1 inactivating antibodies, reducing the size and frequency of necroinflammatory foci.

Effect of LPS and Ethanol on Hepatic Fibrin Deposition and Circulating Tat Levels LPS is known to activate of the coagulation system, which can lead to fibrin deposition and subsequent hemostasis. The effect of LPS and ethanol on hepatic fibrin deposition was therefore determined. FIG. 21 illustrates representative confocal photomicrographs depicting immunofluorescent detection of fibrin deposition. LPS caused fibrin deposition in sinusoidal spaces of the liver lobule (data not shown). Ethanol alone did not cause a visible increase in fibrin deposition.

However, ethanol treatment exacerbated accumulation of fibrin caused by LPS (data not shown).

To determine whether enhanced fibrin deposition was a consequence of exaggerated thrombin generation, plasma thrombin-antithrombin (TAT) levels were determined (data not shown) as an index of thrombin activation. Plasma TAT levels were significantly increased by LPS alone (data not shown). However, ethanol pretreatment did not alter the increase in plasma TAT concentrations caused by LPS. Despite the lack of difference between indices of coagulation, selective inhibition of thrombin with the specific thrombin inhibitor hirudin completely prevented the increase in fibrin accumulation (data not shown) and liver damage (FIGS. 19 and 21B) caused by ethanol after LPS injection, with values for the latter variables similar to that of LPS alone.

Effect of Ethanol on the Induction of Gene Expression Caused by LPS

Fibrin accumulation may be enhanced not only by increasing deposition via the coagulation cascade, but also by impairing degradation via fibrinolysis. Since thrombin activation (TAT levels, FIG. 5) was not elevated, the effect of ethanol on indices of the latter pathway (i.e., fibrinolysis) was determined. Specifically, the effect of LPS and ethanol on hepatic expression of PAI-1 and TNFα (a known upstream inducer of PAI-1) was quantitated (FIG. 22). Ethanol pre-exposure alone had no effect on hepatic mRNA expression of PAI-1 or TNFα under these conditions. LPS alone induced hepatic expression of PAI-1 and TNFα as early as 1 h after LPS and was still induced after 48 h. Exposure to ethanol prior to LPS enhanced the increase in PAI-1 mRNA expression caused by LPS at the 4 and 24 h time points. In contrast, TNFα mRNA expression was not enhanced by ethanol at the 4 h time point, and was significantly decreased at the 24 h time point.

Effect of LPS and Ethanol on the Activation of ERK1/2

Both, inflammation and cell death were enhanced by ethanol in response to LPS. It is known that MAPK signaling cascades are involved in both processes. Furthermore, MAPK (i.e., ERK1/2) is a known upstream mediator of PAI-1 induction. Furthermore, previous studies by others have shown that ERK1/2 activation in response to LPS is enhanced by alcohol pre-exposure in rodent liver. The effect of LPS and ethanol exposure on the phosphorylation (activation) status of ERK1/2 was therefore performed; representative blots (FIG. 23A) and densitometric analysis (FIG. 23B) are shown. LPS alone caused an increase in ERK1/2 activation at the 4 h time point. Whereas ethanol administration alone did not significantly alter ERK1/2 phosphorylation at any time point, it enhanced LPS-induced ERK1/2 protein phosphorylation (~2 fold). Treatment with the upstream MAPK inhibitor U0126 significantly blocked the induction of ERK1/2 protein phosphorylation (FIG. 23). Hirudin co-administration did not significantly attenuate the increase in ERK phosphorylation caused by the combination of LPS and ethanol, with an average value 3.7-fold higher than control. Analogous to the effect of hirudin on fibrin accumulation (data not shown), U0126 treatment not only blunted the accumulation of fibrin (data now shown), but also blunted the increase in LPS-induced liver damage caused by ethanol (FIGS. 19 and 21, bottom). While U0126 had no effect on TNFα mRNA expression, it prevented the increase in PAI-1 expression caused by ethanol in the presence of LPS at the peak time point (4 h). U0126 values were similar to LPS alone (FIG. 22).

Effect of LPS and Ethanol in TNFR1' Mice and Mice Treated with PAI-1 Antibody

The data presented above support a mechanism by which TNFα (via ERK1/2) induces PAI-1; this induction inhibits fibrinolysis, causing fibrin to accumulate (data now shown). The effect of ethanol and LPS on liver damage and fibrin accumulation in TNFR1$^{-/-}$ mice or in mice injected with PAI-1 antibodies was determined (FIG. 24) to directly test this hypothesis. Analogous to findings with hirudin and U0126 (FIG. 21), the enhancement of LPS-induced liver damage caused by ethanol was almost completely abrogated in TNFR1 knockout mice or mice treated with PAI-1 antibody (FIG. 24). Specifically, the increase in the pathology scores caused by ethanol/LPS (see FIG. 21A) and transaminases were blunted (FIG. 24). Furthermore, the accumulation of fibrin caused by ethanol/LPS under these conditions (data not shown) was also completely abrogated in these 2 groups (data not shown).

Ethanol Enhances Inflammatory Damage in Mouse Liver.

Exposure of the liver to low levels of LPS is common and occurs through multiple means. For example, both acute and chronic alcohol consumption increase circulating LPS levels in human subjects. Whereas inflammatory responses triggered by small doses of LPS are typically non-injurious, physiological/biochemical stresses can synergistically enhance the hepatotoxic response to LPS. Indeed, in addition to increasing circulating LPS, ethanol also enhances inflammation and liver damage caused by acute LPS, injected>20 h after ethanol exposure. This response to acute LPS is hypothesized to be mechanistically similar to chronic alcoholic liver disease, and it is the rationale for employing this model. Enhancement of LPS-induced inflammation and liver damage caused by ethanol was shown to correlate with a robust increase in fibrin accumulation (FIGS. 19-21, and data not shown). Furthermore, this effect of ethanol was nearly completely abrogated by blocking the initiation of the coagulation cascade with hirudin (FIGS. 19-21 and data not shown). Taken together, the study indicates that ethanol enhances inflammation and liver injury owing to a bolus injection of LPS via thrombin-dependent fibrin deposition.

LPS-Induced PAI-1 Expression and Liver Damage Caused by Ethanol Preexposure is Mediated Via ERK Signaling Previous studies have shown that pretreatment of rats with thrombin inhibitors, such as heparin or hirudin, prevented the activation of the coagulation cascade and subsequent liver injury induced by large doses of LPS. The coagulation cascade can contribute to liver injury, in part, through the generation of occlusive fibrin clots in the hepatic sinusoids which can cause hemostasis, microregional hypoxia and subsequent hepatocellular death. Ethanol pretreatment enhanced LPS-induced fibrin accumulation and liver injury in LPS-treated mice, both of which were prevented by hirudin (FIGS. 19-21 and data not shown). However, the exaggerated fibrin accumulation induced by ethanol was not associated with an enhancement of LPS-induced coagulation, per se, as thrombin-antithrombin levels were similar in LPS and ethanol/LPS groups (data not shown).

In addition to deposition by coagulation, the level of fibrin ECM is also regulated by degradation of the existing matrix (i.e., fibrinolysis). Specifically, inhibition of fibrinolysis can cause this ECM to accumulate, even in the absence of enhanced deposition by the thrombin cascade. A major inhibitor of fibrinolysis is PAI-1, via blocking the activation of plasmin by plasminogen activators (uPA and tPA). In the current study, ethanol enhanced the increase in PAI-1 expression caused by LPS as early as 4 h after injection of LPS (FIG. 22). Elevated PAI-1 and hepatic fibrin have correlated with enhanced LPS-induced liver damage in other models, such as idiosyncratic drug toxicity, surgical resection, or adipocytokine administration. The 'classic' role of PAI-1 in impairing fibrinolysis can contribute to inflammation. For example, fibrin matrices have been shown to be permissive to chemotaxis and activation of monocytes and leukocytes. In addition to altering fibrin metabolism, PAI-1 can alter the profile of other inflammatory mediators via inhibition of plasminogen activators. For example, the inhibition of plasmin activation by PAI-1 prevents the conversion of secreted latent TGFβ to its active form, which may mediate anti-inflammatory effects, especially on monocytes/macrophages. These mechanisms are not mutually exclusive and can occur in tandem. Blocking active PAI-1 with an anti-PAI-1 antibody (CT140) prevented the recruitment of neutrophils to the liver caused by the combination of LPS and ethanol (FIG. 24).

Regulation of the expression of PAI-1 is multifaceted in the cell; the increase in PAI-1 expression caused by LPS after ethanol (FIG. 22) was coupled with enhanced activation of ERK1/2 (FIG. 23). The ERK1/2 MAPK signaling pathway is known to play a role in the expression of PAI-1 in response to TNFα. In agreement with these studies, the increase in PAI-1 expression caused by LPS after ethanol was significantly attenuated (~4 fold) by U0126 administration (FIG. 22). The inhibition of PAI-1 induction by U0126 was also mirrored by prevention of fibrin accumulation (FIG. 21) and liver damage (FIG. 19) under these conditions, showing that exacerbated LPS-induced liver damage caused by ethanol is linked to increased fibrin accumulation and increased PAI-1. Lastly, the accumulation of fibrin, neutrophils and liver injury was attenuated in TNFR1$^{-/-}$ mice. Taken together, these results show that the increased activation of ERK1/2 by TNFα enhances LPS-induced PAI-1 expression and fibrin deposition that contribute to liver injury. Additionally, the increase in expression of TNFα caused by LPS was not detectably enhanced in liver by ethanol pre-exposure (FIG. 22), however there was an increase in the activation of ERK1/2 activation by this pre-exposure (FIG. 23).

One would recognize that the data provided herein demonstrates that humanized anti-PAI-1 antibodies described herein are effective in treating liver fibrosis. Fibrosis is associated with all of the conditions/diseases described herein. Therefore, one would recognize that the data presented illustrates anti-fibrotic therapeutic regiments to treat fibrosis regardless of the disease.

Aspects of this invention may be embodied in other forms or carried out in other ways without departing from the spirit or essential characteristics thereof. The present disclosure is therefore to be considered as in all aspects illustrated and not restrictive, and all changes which come within the meaning and range of equivalency are intended to be embraced therein.

What is claimed is:

1. A method of treating a fibrotic condition in a subject, comprising administering to the subject an antibody or antigen-binding fragment thereof that binds plasminogen activator inhibitor-1 (PAI-1), wherein the fibrotic condition is a liver fibrosis, and wherein the antibody or antigen-binding fragment thereof comprises a heavy chain variable region and a light chain variable region, wherein said heavy chain variable region comprises:
(i) a CDR1 of SEQ ID NO: 93, a CDR2 of SEQ ID NO: 94, and a CDR3 of SEQ ID NO: 95;
(ii) a heavy chain FR1 having the amino acid sequence of SEQ ID NO: 78 or the amino acid sequence of SEQ ID NO: 78 except for one or more substitutions selected from the group consisting of:
  (a) a substitution of tyrosine (Y) by phenylalanine (F) at position 27;
  (b) a substitution of threonine (T) by asparagine (N) at position 28;
  (c) a substitution of phenylalanine (F) by isoleucine (I) at position 29; and
  (d) a substitution of threonine (T) by lysine (K) at position 30 utilizing the Kabat numbering system;
(iii) a heavy chain FR2 having the amino acid sequence of SEQ ID NO: 84 or the amino acid sequence of SEQ ID NO: 84 except for one or more substitutions selected from the group consisting of:
  (a) a substitution of glutamine (Q) by lysine (K) at position 38, and
  (b) a substitution of methionine (M) by isoleucine (I) at position 48 utilizing the Kabat numbering system;
(iv) a heavy chain FR3 having the amino acid sequence of SEQ ID NO: 88 or the amino acid sequence of SEQ ID NO: 88 except for one or more substitutions selected from the group consisting of:
  (a) a substitution of arginine (R) by lysine (K) at position 66;
  (b) a substitution of valine (V) by alanine (A) at position 67;
  (c) a substitution of alanine (A) by threonine (T) at position 93; and
  (d) a substitution of threonine (T) by arginine (R) at position 94 utilizing the Kabat numbering system; and (v) a heavy chain FR4 having the amino acid sequence of SEQ ID NO: 92 or the amino acid sequence of SEQ ID NO: 92 except for one or more conservative substitutions;

and said light chain variable region comprises:
(i) a CDR1 of SEQ ID NO: 96, a CDR2 of SEQ ID NO: 97, and a CDR3 of SEQ ID NO: 98;
(ii) a light chain FR1 having the amino acid sequence of SEQ ID NO: 68 or the amino acid sequence of SEQ ID NO: 68 except for one or more conservative substitutions;
(iii) a light chain FR2 having the amino acid sequence of SEQ ID NO: 69 or the amino acid sequence of SEQ ID NO: 69 except for one or more substitutions selected from the group consisting of:
  (a) a substitution of alanine (A) by threonine (T) at position 43; and
  (b) a substitution of proline (P) by valine (V) at position 44 utilizing the Kabat numbering system;
(iv) a light chain FR3 having the amino acid sequence of SEQ ID NO: 73 or the amino acid sequence of SEQ ID NO: 73 except for one or more substitutions selected from the group consisting of:
  (a) a substitution of phenylalanine (F) by tyrosine (Y) at position 71; and
  (b) a substitution of tyrosine (Y) by phenylalanine (F) at position 87 utilizing the Kabat numbering system; and
(v) a light chain FR4 having the amino acid sequence of SEQ ID NO: 77 or the amino acid sequence of SEQ ID NO: 77 except for one or more conservative substitutions.

2. The method of claim 1, wherein said antibody, or antigen-binding fragment thereof, comprises a heavy chain variable region having an amino acid sequence set forth as SEQ ID NO: 64, 65, 66 or 67; and a light chain variable region having an amino acid sequence set forth as SEQ ID NO: 62 or 63.

3. The method of claim 1, wherein said liver fibrosis is selected from cirrhosis, hepatitis C viral (HCV) infection, hepatitis B viral (HBV) infection, non-alcoholic steatohepatitis (NASH), Alcoholic liver disease (ALD), Primary sclerosing cholangitis, Autoimmune hepatitis, Hereditary hemochromatosis, and Wilson's disease.

4. The method of claim 1, wherein said antibody or antigen-binding fragment thereof is labeled with a therapeutic label, a detectable label or both.

5. The method of claim 1, further comprising administering one or more anti-fibrotic therapeutic regimens.

6. The method of claim 5, wherein said one or more anti-fibrotic therapeutic regimens is a second anti-PAI-1 antibody or antigen-binding fragment thereof.

* * * * *

SEQUENCE LISTING

<160> NUMBER OF SEQ ID NOS: 128

<210> SEQ ID NO 1
<211> LENGTH: 113
<212> TYPE: PRT
<213> ORGANISM: Mus sp.

<400> SEQUENCE: 1

Asp Ile Val Met Thr Gln Ser Pro Ser Ser Leu Ala Val Ser Val Gly
1               5                   10                  15

Glu Lys Val Thr Met Ser Cys Lys Ser Ser Gln Ser Leu Leu Asn Ile
            20                  25                  30

Ile Lys Gln Lys Asn Cys Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys

<210> SEQ ID NO 2
<211> LENGTH: 113
<212> TYPE: PRT
<213> ORGANISM: Homo sapiens -continued

```
<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
                100                 105                 110

Lys

<210> SEQ ID NO 3
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ile
            20                  25                  30

Ile Lys Gln Lys Asn Cys Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gln Gly Thr Lys Leu Glu Ile
                100                 105                 110

Lys

<210> SEQ ID NO 4
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ile
            20                  25                  30

Ile Lys Gln Lys Asn Cys Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
```

```
                50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Tyr Pro Tyr Thr Phe Gly Gln Gly Thr Lys Leu Glu Ile
            100                 105                 110

Lys

<210> SEQ ID NO 5
<211> LENGTH: 23
<212> TYPE: PRT
<213> ORGANISM: Homo sapiens

<400> SEQUENCE: 5

Asp Ile Val Met Thr Gln Ser Pro Asp Ser Leu Ala Val Ser Leu Gly
 1               5                  10                  15

Glu Arg Ala Thr Ile Asn Cys
             20

<210> SEQ ID NO 6
<211> LENGTH: 23
<212> TYPE: PRT
<213> ORGANISM: Homo sapiens

<400> SEQUENCE: 6

Asp Ile Val Met Thr Gln Ser Pro Asp Ser Leu Ala Val Ser Leu Gly
 1               5                  10                  15

Glu Arg Ala Thr Ile Ser Cys
             20

<210> SEQ ID NO 7
<211> LENGTH: 15
<212> TYPE: PRT
<213> ORGANISM: Homo sapiens

<400> SEQUENCE: 7

Trp Tyr Gln Gln Lys Pro Gly Gln Pro Pro Lys Leu Leu Ile Tyr
 1               5                  10                  15

<210> SEQ ID NO 8
<211> LENGTH: 32
<212> TYPE: PRT
<213> ORGANISM: Homo sapiens

<400> SEQUENCE: 8

Gly Val Pro Asp Arg Phe Ser Gly Ser Gly Ser Gly Thr Asp Phe Thr
 1               5                  10                  15

Leu Thr Ile Ser Ser Leu Gln Ala Glu Asp Val Ala Val Tyr Tyr Cys
             20                  25                  30

<210> SEQ ID NO 9
<211> LENGTH: 10
<212> TYPE: PRT
<213> ORGANISM: Homo sapiens

<400> SEQUENCE: 9

Phe Gly Gln Gly Thr Lys Leu Glu Ile Lys
 1               5                  10

<210> SEQ ID NO 10
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Ser Ser Gln Ser Leu Leu Asn Ile Ile Lys Gln Lys Asn Cys Leu
1               5                   10                  15
Ala

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Ser Ser Gln Ser Leu Leu Asn Ile Ile Lys Gln Lys Asn Leu Leu
1               5                   10                  15
Ala

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Ala Ser Thr Arg Glu Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Gln Tyr Tyr Ser Tyr Pro Tyr Thr
1               5

<210> SEQ ID NO 14
<211> LENGTH: 113
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 15
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ile Gln Leu Val Gln Ser Gly Pro Glu Leu Lys Lys Pro Gly Lys
1               5                   10                  15

Thr Val Thr Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Thr Asp Asp Phe
        50                  55                  60

Lys Gly Arg Phe Ala Phe Ser Leu Asp Thr Ser Ala Ser Thr Ala Tyr
65                  70                  75                  80

Leu Gln Ile Ser Asn Leu Lys Asn Glu Asp Thr Ala Thr Tyr Phe Cys
                85                  90                  95

Ala Lys Asp Val Ser Gly Phe Val Phe Asp Tyr Trp Gly Gln Gly Thr
            100                 105                 110

Thr Val Thr Val Ser Ser
        115

<210> SEQ ID NO 16
<211> LENGTH: 118
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Thr Asp Asp Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Val Ser Gly Phe Val Phe Asp Tyr Trp Gly Gln Gly Thr
            100                 105                 110

Leu Val Thr Val Ser Ser
        115

<210> SEQ ID NO 17
<211> LENGTH: 118
<212> TYPE: PRT
<213> ORGANISM: Artificial Sequence
```

<220> FEATURE:
<223> OTHER INFORMATION: Description of Artificial Sequence: Synthetic
    polypeptide

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Thr Asp Asp Phe
    50                  55                  60

Lys Gly Arg Phe Thr Met Thr Leu Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Asp Val Ser Gly Phe Val Phe Asp Tyr Trp Gly Gln Gly Thr
            100                 105                 110

Leu Val Thr Val Ser Ser
        115

<210> SEQ ID NO 18
<211> LENGTH: 118
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Thr Phe Thr Leu Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Asp Val Ser Gly Phe Val Phe Asp Tyr Trp Gly Gln Gly Thr
            100                 105                 110

Leu Val Thr Val Ser Ser
        115

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Trp Val Arg Gln Ala Pro Gly Gln Gly Leu Glu Trp Met Gly
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Trp Val Lys Gln Ala Pro Gly Gln Gly Leu Glu Trp Met Gly
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Trp Val Arg Gln Ala Pro Gly Gln Gly Leu Lys Trp Met Gly
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Trp Val Arg Gln Ala Pro Gly Gln Gly Leu Val Trp Met Gly
1               5                   10

<210> SEQ ID NO 25
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 25

Trp Val Lys Gln Ala Pro Gly Gln Gly Leu Lys Trp Met Gly
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Val Lys Gln Ala Pro Gly Gln Gly Leu Val Trp Met Gly
1               5                   10

<210> SEQ ID NO 27
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Phe Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Phe Thr Phe Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 30
<211> LENGTH: 32
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 30

Arg Phe Thr Ile Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Phe Thr Phe Thr Leu Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Phe Thr Ile Thr Leu Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Phe Thr Phe Thr Leu Asp Thr Ser Ile Ser Thr Ala Tyr Met Glu
1               5                   10                  15

Leu Ser Arg Leu Arg Ser Asp Asp Thr Ala Val Tyr Tyr Cys Ala Lys
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Phe Thr Ile Thr Leu Asp Thr Ser Ile Ser Thr Ala Tyr Met Glu
1               5                   10                  15

Leu Ser Arg Leu Arg Ser Asp Asp Thr Ala Val Tyr Tyr Cys Ala Lys
            20                  25                  30

```
<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Phe Thr Met Thr Leu Asp Thr Ser Ile Ser Thr Ala Tyr Met Glu
1               5                   10                  15

Leu Ser Arg Leu Arg Ser Asp Asp Thr Ala Val Tyr Tyr Cys Ala Lys
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Phe Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Lys
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Val Thr Phe Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Val Thr Ile Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Val Thr Phe Thr Leu Asp Thr Ser Ile Ser Thr Ala Tyr Met Glu
1               5                   10                  15
```

-continued

Leu Ser Arg Leu Arg Ser Asp Asp Thr Ala Val Tyr Tyr Cys Ala Arg
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Val Thr Ile Thr Leu Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Val Thr Phe Thr Leu Asp Thr Ser Ile Ser Thr Ala Tyr Met Glu
1               5                   10                  15

Leu Ser Arg Leu Arg Ser Asp Asp Thr Ala Val Tyr Tyr Cys Ala Lys
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Val Thr Ile Thr Leu Asp Thr Ser Ile Ser Thr Ala Tyr Met Glu
1               5                   10                  15

Leu Ser Arg Leu Arg Ser Asp Asp Thr Ala Val Tyr Tyr Cys Ala Lys
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Val Thr Phe Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Lys
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 44

Arg Val Thr Ile Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Lys
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Phe Thr Phe Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Lys
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Phe Thr Ile Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Lys
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Val Thr Met Thr Leu Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Val Thr Met Thr Leu Asp Thr Ser Ile Ser Thr Ala Tyr Met Glu
1               5                   10                  15

Leu Ser Arg Leu Arg Ser Asp Asp Thr Ala Val Tyr Tyr Cys Ala Lys
            20                  25                  30

<210> SEQ ID NO 49
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Phe Thr Met Thr Leu Asp Thr Ser Ile Ser Thr Ala Tyr Met Glu
1               5                   10                  15
Leu Ser Arg Leu Arg Ser Asp Asp Thr Ala Val Tyr Tyr Cys Ala Arg
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Val Thr Met Thr Arg Asp Thr Ser Ile Ser Thr Ala Tyr Met Glu
1               5                   10                  15
Leu Ser Arg Leu Arg Ser Asp Asp Thr Ala Val Tyr Tyr Cys Ala Lys
            20                  25                  30

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Gly Gln Gly Thr Leu Val Thr Val Ser Ser
1               5                   10

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asn Tyr Gly Met Asn
1               5

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Trp Ile Asn Thr Tyr Thr Gly Glu Pro Thr Tyr Thr Asp Asp Phe Lys
1               5                   10                  15
Gly

<210> SEQ ID NO 54
<211> LENGTH: 9
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 54

Asp Val Ser Gly Phe Val Phe Asp Tyr
1               5

<210> SEQ ID NO 55
<211> LENGTH: 23
<212> TYPE: PRT
<213> ORGANISM: Homo sapiens

<400> SEQUENCE: 55

Asp Ile Val Met Thr Gln Ser Pro Asp Ser Leu Ala Val Ser Leu Gly
1               5                   10                  15

Glu Arg Ala Thr Ile Thr Cys
            20

<210> SEQ ID NO 56
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Leu Leu Asn Ile
            20                  25                  30

Ile Lys Gln Lys Asn Cys Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gln Gly Thr Lys Leu Glu Ile
            100                 105                 110

Lys

<210> SEQ ID NO 57
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Leu Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 58
<211> LENGTH: 107
<212> TYPE: PRT
<213> ORGANISM: Mus sp.

-continued

```
<400> SEQUENCE: 58

Asp Ile Gln Met Thr Gln Ser Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu His Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Lys Gln
65                  70                  75                  80

Glu Asp Phe Ala Thr Tyr Phe Cys Gln Gln Gly Asp Thr Leu Pro Pro
                85                  90                  95

Thr Phe Gly Gly Gly Thr Lys Leu Glu Ile Lys
            100                 105

<210> SEQ ID NO 59
<211> LENGTH: 120
<212> TYPE: PRT
<213> ORGANISM: Mus sp.

<400> SEQUENCE: 59

Gln Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Ile
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Thr Glu Phe Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Ser Leu Tyr Gly Ser Ser Pro Trp Tyr Phe Asp Val Trp Gly
            100                 105                 110

Gln Gly Thr Thr Val Thr Val Ser
        115                 120

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

```
Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105

<210> SEQ ID NO 61
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ile
            20                  25                  30

Tyr Met Tyr Trp Val Gln Gln Ala Pro Gly Lys Gly Leu Glu Trp Met
        35                  40                  45

Gly Arg Ile Asp Pro Ala Asn Gly Asn Thr Glu Phe Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Leu Tyr Gly Ser Ser Pro Trp Tyr Phe Asp Val Trp Gly
            100                 105                 110

Gln Gly Thr Leu Val Thr Val Ser
        115                 120

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu His Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Thr Leu Pro Pro
                85                  90                  95

Thr Phe Gly Gly Gly Thr Lys Val Glu Ile Lys
            100                 105

<210> SEQ ID NO 63
<211> LENGTH: 107
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu His Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asp Thr Leu Pro Pro
                85                  90                  95

Thr Phe Gly Gly Gly Thr Lys Val Glu Ile Lys
            100                 105

<210> SEQ ID NO 64
<211> LENGTH: 120
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 64

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ile
            20                  25                  30

Tyr Met Tyr Trp Val Gln Gln Ala Pro Gly Lys Gly Leu Glu Trp Met
        35                  40                  45

Gly Arg Ile Asp Pro Ala Asn Gly Asn Thr Glu Phe Asp Pro Lys Phe
50                  55                  60

Gln Asp Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Leu Tyr Gly Ser Ser Pro Trp Tyr Phe Asp Val Trp Gly
            100                 105                 110

Gln Gly Thr Leu Val Thr Val Ser
        115                 120

<210> SEQ ID NO 65
<211> LENGTH: 120
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 65

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Ile
            20                  25                  30

Tyr Met Tyr Trp Val Gln Gln Ala Pro Gly Lys Gly Leu Glu Trp Met
        35                  40                  45

```
Gly Arg Ile Asp Pro Ala Asn Gly Asn Thr Glu Phe Asp Pro Lys Phe
            50                  55                  60

Gln Asp Arg Ala Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Leu Tyr Gly Ser Ser Pro Trp Tyr Phe Asp Val Trp Gly
            100                 105                 110

Gln Gly Thr Leu Val Thr Val Ser
            115                 120

<210> SEQ ID NO 66
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Val Gln Ser Gly Ala Glu Val Lys Lys Pro Gly Ala
 1               5                  10                  15

Thr Val Lys Ile Ser Cys Lys Val Ser Gly Phe Asn Ile Lys Asp Ile
             20                  25                  30

Tyr Met Tyr Trp Val Gln Gln Ala Pro Gly Lys Gly Leu Glu Trp Met
         35                  40                  45

Gly Arg Ile Asp Pro Ala Asn Gly Asn Thr Glu Phe Asp Pro Lys Phe
     50                  55                  60

Gln Asp Arg Ala Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Thr Arg Ser Leu Tyr Gly Ser Ser Pro Trp Tyr Phe Asp Val Trp Gly
            100                 105                 110

Gln Gly Thr Leu Val Thr Val Ser
            115                 120

<210> SEQ ID NO 67
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Gln Ser Gly Ala Glu Val Lys Lys Pro Gly Ala
 1               5                  10                  15

Thr Val Lys Ile Ser Cys Lys Val Ser Gly Phe Asn Ile Lys Asp Ile
             20                  25                  30

Tyr Met Tyr Trp Val Gln Gln Ala Pro Gly Lys Gly Leu Glu Trp Ile
         35                  40                  45

Gly Arg Ile Asp Pro Ala Asn Gly Asn Thr Glu Phe Asp Pro Lys Phe
     50                  55                  60

Gln Asp Lys Ala Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95
```

```
Ala Arg Ser Leu Tyr Gly Ser Ser Pro Trp Tyr Phe Asp Val Trp Gly
                100                 105                 110

Gln Gly Thr Leu Val Thr Val Ser
        115                 120

<210> SEQ ID NO 68
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Trp Tyr Gln Gln Lys Pro Gly Lys Ala Pro Lys Leu Leu Ile Tyr
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Trp Tyr Gln Gln Lys Pro Gly Lys Thr Pro Lys Leu Leu Ile Tyr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Trp Tyr Gln Gln Lys Pro Gly Lys Ala Val Lys Leu Leu Ile Tyr
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Tyr Gln Gln Lys Pro Gly Lys Thr Val Lys Leu Leu Ile Tyr
1               5                   10                  15
```

```
<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Val Pro Ser Arg Phe Ser Gly Ser Gly Ser Gly Thr Asp Tyr Thr
1               5                   10                  15

Phe Thr Ile Ser Ser Leu Gln Pro Glu Asp Ile Ala Thr Tyr Tyr Cys
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Phe Cys
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Val Pro Ser Arg Phe Ser Gly Ser Gly Ser Gly Thr Asp Tyr Thr
1               5                   10                  15

Phe Thr Ile Ser Ser Leu Gln Pro Glu Asp Ile Ala Thr Tyr Phe Cys
            20                  25                  30

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Phe Gly Gly Gly Thr Lys Val Glu Ile Lys
1               5                   10
```

```
<210> SEQ ID NO 78
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30

<210> SEQ ID NO 79
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys
            20                  25                  30

<210> SEQ ID NO 80
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Phe Thr
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Asn Phe Thr
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82
```

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Ile Thr
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Lys
            20                  25                  30

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Val Gln Gln Ala Pro Gly Lys Gly Leu Glu Trp Met Gly
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Trp Val Gln Gln Ala Pro Gly Lys Gly Leu Glu Trp Ile Gly
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Trp Val Lys Gln Ala Pro Gly Lys Gly Leu Glu Trp Met Gly
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Trp Val Lys Gln Ala Pro Gly Lys Gly Leu Glu Trp Ile Gly
1               5                   10

```
<210> SEQ ID NO 88
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ala Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Ala Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Thr Arg
            20                  25                  30

<210> SEQ ID NO 91
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Lys Ala Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Trp Gly Gln Gly Thr Leu Val Thr Val Ser
1               5                   10
```

```
<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asp Ile Tyr Met Tyr
1               5

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Ile Asp Pro Ala Asn Gly Asn Thr Glu Phe Asp Pro Lys Phe Gln
1               5                   10                  15

Asp

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Leu Tyr Gly Ser Ser Pro Trp Tyr Phe Asp Val
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ala Ser Gln Asp Ile Ser Asn Tyr Leu His
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Tyr Thr Ser Arg Leu His Ser
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                                    peptide

<400> SEQUENCE: 98

Gln Gln Gly Asp Thr Leu Pro Pro Thr
1               5

<210> SEQ ID NO 99
<211> LENGTH: 467
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 99

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Thr
65                  70                  75                  80

Asp Asp Phe Lys Gly Arg Phe Thr Met Thr Leu Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Lys Asp Val Ser Gly Phe Val Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335
```

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 100
<211> LENGTH: 467
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 100

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Asn Tyr Gly Met Asn Trp Val Arg Gln Ala Pro Gly Gln Gly Leu
            50                  55                  60

Glu Trp Met Gly Trp Ile Asn Thr Tyr Thr Gly Glu Pro Thr Tyr Thr
65                  70                  75                  80

Asp Asp Phe Lys Gly Arg Phe Thr Met Thr Leu Asp Thr Ser Ile Ser
            85                  90                  95

Thr Ala Tyr Met Glu Leu Ser Arg Leu Arg Ser Asp Asp Thr Ala Val
            100                 105                 110

Tyr Tyr Cys Ala Lys Asp Val Ser Gly Phe Val Phe Asp Tyr Trp Gly
            115                 120                 125

Gln Gly Thr Leu Val Thr Val Ser Ser Ala Ser Thr Lys Gly Pro Ser
            130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
            210                 215                 220

```
Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser Gln
            275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
    355                 360                 365

Tyr Thr Leu Pro Pro Ser Pro Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
    435                 440                 445

His Glu Ala Leu His Asn His Tyr Thr Gln Lys Ser Leu Ser Leu Ser
450                 455                 460

Leu Gly Lys
465

<210> SEQ ID NO 101
<211> LENGTH: 240
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 101

Met Arg Leu Pro Ala Gln Leu Leu Gly Leu Leu Met Leu Trp Val Ser
1               5                   10                  15

Gly Ser Ser Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Leu Leu Asn Ile Ile Lys Gln Lys Asn Cys Leu Ala Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110
```

```
Tyr Cys Gln Gln Tyr Tyr Ser Tyr Pro Tyr Thr Phe Gly Gln Gly Thr
            115                 120                 125

Lys Leu Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
            165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
            210                 215                 220

Gln Gly Leu Ser Ser Pro Val Thr Lys Ser Phe Asn Arg Gly Glu Cys
225                 230                 235                 240

<210> SEQ ID NO 102
<211> LENGTH: 546
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 102
atatataagc ttgccaccat ggactggact tggcgcatcc tcttttttggt ggccgccgct      60 actggagctc attctcaggt ccagcttgtc cagtctggag ctgaagtgaa aaaacctgga     120
gcttctgtga agtatcttg taaggcaagc ggatatactt tcacaaacta cggcatgaat      180
tgggttcgcc aggcccctgg ccagggactg gagtggatgg gatggattaa tacttcacc      240 ggagagccta cctacaccga tgactttaag ggtcgtttta caatgaccct cgacacaagc     300
atttccactg cctacatgga gctgtcccga ctcagaagcg atgacaccgc cgtatactac     360
tgtgctaagg atgtttctgg attcgtgttc gattactggg gccagggtac actggtgacc     420
gtatctagcg cctcaaccaa aggcccatct gtttttcccct tggcccctag ctccaagtct     480
acatccgggg gcacagcagc tctgggctgt cttgtgaagg attactttcc agaaccggtg     540
actgtg                                                                546

<210> SEQ ID NO 103
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Thr
```

```
                65                  70                  75                  80
Asp Asp Phe Lys Gly Arg Phe Thr Met Thr Leu Asp Thr Ser Ile Ser
                        85                  90                  95
Thr Ala Tyr Met Glu Leu Ser Arg Leu Arg Ser Asp Thr Ala Val
                100                 105                 110
Tyr Tyr Cys Ala Lys Asp Val Ser Gly Phe Val Phe Asp Tyr Trp Gly
                115                 120                 125
Gln Gly Thr Leu Val Thr Val Ser Ser Ala Ser Thr Lys Gly Pro Ser
        130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
atatataagc ttgccaccat ggac                                              24

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Glu Pro Val Thr Val
1               5

<210> SEQ ID NO 106
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
ctatatataa gcttgccacc atgaggttgc cagctcagct cctcggtctg ctgatgctct       60
gggtaagcgg cagcagcggt gacatcgtga tgacccagtc ccctgatagt ttggctgtga      120
gtctcggcga gcgggccaca attaattgta gagcagtca aagtctgttg aatatcatta       180
agcagaaaaa ttgtcttgcc tggtatcaac aaaagcctgg ccagccacct aagctgctga      240
tatactgggc tagtactcgt gaatccggtg tgcccgatcg gttttccgga agcggttccg      300
ggactgactt cactctgaca atttctagcc tgcaggccga ggacgttgcc gtttactact      360
gccagcagta ttacagttac ccctacacat tcggacaggg aaccaaactg gaaatcaaac      420
gcactgtcgc cgctccatct gtcttcatct tc                                    452

<210> SEQ ID NO 107
<211> LENGTH: 144
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 107

Met Arg Leu Pro Ala Gln Leu Gly Leu Leu Met Leu Trp Val Ser
1               5                   10                  15

Gly Ser Ser Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Leu Leu Asn Ile Ile Lys Gln Lys Asn Cys Leu Ala Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Tyr Pro Tyr Thr Phe Gly Gln Gly Thr
        115                 120                 125

Lys Leu Glu Ile Lys Arg Thr Val Ala Ala Pro Ser Val Phe Ile Phe
    130                 135                 140

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
atatataagc ttgccaccat g                                              21

<210> SEQ ID NO 109
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ccatctgtct tc                                                        12

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Pro Ser Val Phe Ile Phe
1               5

<210> SEQ ID NO 111
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
atatagatct ttaattaatg ccaccatgga ctggac            36

<210> SEQ ID NO 112
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
atatgctagc ggccggcctc atcatttacc cagagacagg            40

<210> SEQ ID NO 113
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
atatgctagc ggccggcctc atcatttacc cggagacagg            40

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
atatggatcc gcggccgcct actaacactc tcccctgttg            40

<210> SEQ ID NO 115
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
atattccgga atttaaattc ccaccatgag gttgccag            38

<210> SEQ ID NO 116
<211> LENGTH: 118
<212> TYPE: PRT
<213> ORGANISM: Homo sapiens

<400> SEQUENCE: 116

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Thr Phe Thr Leu Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Lys Asp Val Ser Gly Phe Val Phe Asp Tyr Trp Gly Gln Gly Thr
            100                 105                 110

Leu Val Thr Val Ser Ser
            115

<210> SEQ ID NO 117
<211> LENGTH: 118
<212> TYPE: PRT
<213> ORGANISM: Homo sapiens

<400> SEQUENCE: 117

Gln Leu Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Val Trp Met
        35                  40                  45

Gly Trp Ile Asn Thr Tyr Thr Gly Glu Pro Thr Tyr Thr Asp Asp Phe
50                  55                  60

Lys Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Asp Val Ser Gly Phe Val Phe Asp Tyr Trp Gly Gln Gly Thr
            100                 105                 110

Leu Val Thr Val Ser Ser
            115

<210> SEQ ID NO 118
<211> LENGTH: 120
<212> TYPE: PRT
<213> ORGANISM: Homo sapiens

<400> SEQUENCE: 118

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Ile
            20                  25                  30

Tyr Met Tyr Trp Val Lys Gln Ala Pro Gly Lys Gly Leu Glu Trp Ile
        35                  40                  45

Gly Arg Ile Asp Pro Ala Asn Gly Asn Thr Glu Phe Ala Glu Lys Phe
50                  55                  60

Gln Gly Lys Ala Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Thr Arg Ser Leu Tyr Gly Ser Ser Pro Trp Tyr Phe Asp Val Trp Gly
            100                 105                 110

Gln Gly Thr Leu Val Thr Val Ser
            115                 120

<210> SEQ ID NO 119
<211> LENGTH: 107
<212> TYPE: PRT
<213> ORGANISM: Homo sapiens

<400> SEQUENCE: 119

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu His Trp Tyr Gln Gln Lys Pro Gly Lys Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65              70                  75                  80

Glu Asp Ile Ala Thr Tyr Phe Cys Gln Gln Tyr Ser Tyr Pro Tyr
                85                  90                  95

Thr Phe Gly Gly Gly Thr Lys Val Glu Ile Lys
            100                 105
```

<210> SEQ ID NO 120
<211> LENGTH: 21
<212> TYPE: DNA
<213> ORGANISM: artificial sequence
<220> FEATURE:
<223> OTHER INFORMATION: PAI-1 forward primer

<400> SEQUENCE: 120
caccaacatt ttggacgctg a                                              21

<210> SEQ ID NO 121
<211> LENGTH: 25
<212> TYPE: DNA
<213> ORGANISM: artificial sequence
<220> FEATURE:
<223> OTHER INFORMATION: TNF-alpha forward primer

<400> SEQUENCE: 121
catcttctca aaattcgagt gacaa                                          25

<210> SEQ ID NO 122
<211> LENGTH: 18
<212> TYPE: DNA
<213> ORGANISM: artificial sequence
<220> FEATURE:
<223> OTHER INFORMATION: Beta actin forward primer

<400> SEQUENCE: 122
ggctcccagc accatgaa                                                  18

<210> SEQ ID NO 123
<211> LENGTH: 21
<212> TYPE: DNA
<213> ORGANISM: artificial sequence
<220> FEATURE:
<223> OTHER INFORMATION: PAI-1 reverse primer

<400> SEQUENCE: 123
tcagtcatgc ccagcttctc c                                              21

<210> SEQ ID NO 124
<211> LENGTH: 20
<212> TYPE: DNA
<213> ORGANISM: artificial sequence
<220> FEATURE:
<223> OTHER INFORMATION: TNF-alphas reverse primer

<400> SEQUENCE: 124

```
cctccacttg gtggtttgct                                                20

<210> SEQ ID NO 125
<211> LENGTH: 19
<212> TYPE: DNA
<213> ORGANISM: artificial sequence
<220> FEATURE:
<223> OTHER INFORMATION: Beta actin reverse primer

<400> SEQUENCE: 125
agccaccgat ccacacaga                                                 19

<210> SEQ ID NO 126
<211> LENGTH: 20
<212> TYPE: DNA
<213> ORGANISM: artificial sequence
<220> FEATURE:
<223> OTHER INFORMATION: PAI-1 probe

<400> SEQUENCE: 126
ccaggctgcc ccgcctcctc                                                20

<210> SEQ ID NO 127
<211> LENGTH: 15
<212> TYPE: DNA
<213> ORGANISM: artificial sequence
<220> FEATURE:
<223> OTHER INFORMATION: TNF-alpha probe

<400> SEQUENCE: 127
cctgtagccc acgtc                                                     15

<210> SEQ ID NO 128
<211> LENGTH: 29
<212> TYPE: DNA
<213> ORGANISM: artificial sequence
<220> FEATURE:
<223> OTHER INFORMATION: Beta actin probe

<400> SEQUENCE: 128
aagatcattg ctcctcctga gcgcaagta                                      29
```